US008118822B2

(12) United States Patent
Schaller et al.

(10) Patent No.: US 8,118,822 B2
(45) Date of Patent: *Feb. 21, 2012

(54) BRIDGE CLIP TISSUE CONNECTOR APPARATUS AND METHODS

(75) Inventors: Laurent Schaller, Los Altos, CA (US); John D. Nguyen, San Jose, CA (US); Liem Ho, Mountain View, CA (US); Nga Doan, San Jose, CA (US); Cong Thach, San Jose, CA (US)

(73) Assignee: Medtronic, Inc., Minneapolis, MN (US)

( * ) Notice: Subject to any disclaimer, the term of this patent is extended or adjusted under 35 U.S.C. 154(b) by 747 days.

This patent is subject to a terminal disclaimer.

(21) Appl. No.: 09/828,322

(22) Filed: Apr. 5, 2001

(65) Prior Publication Data

US 2001/0018592 A1 Aug. 30, 2001

Related U.S. Application Data

(63) Continuation-in-part of application No. 09/260,623, filed on Mar. 1, 1999, now Pat. No. 6,613,059.

(51) Int. Cl.
*A61B 17/10* (2006.01)
*A61B 17/08* (2006.01)
*A61B 17/04* (2006.01)
*A61B 17/06* (2006.01)
*A61M 29/00* (2006.01)

(52) U.S. Cl. ........ 606/157; 606/228; 606/222; 606/224; 606/232; 606/151; 606/191; 606/198; 606/200; 606/139; 606/144; 606/148; 606/152; 606/158

(58) Field of Classification Search .................. 606/157, 606/228, 222, 223, 224, 232, 151, 191, 198, 606/200, 139, 144, 148, 152, 158
See application file for complete search history.

(56) References Cited

U.S. PATENT DOCUMENTS

| 43,098 A | 6/1864 | Cooper |
| 636,728 A | 11/1899 | Kindel |
| 655,190 A | 8/1900 | Bramson |
| 1,087,186 A | 2/1914 | Scholfield |
| 1,167,014 A | 1/1916 | O'Brien |
| 1,539,221 A | 5/1925 | John |
| 1,583,271 A | 5/1926 | Biro |
| 1,625,602 A | 4/1927 | Gould et al. |
| 1,867,624 A | 7/1932 | Hoffman |
| 2,201,610 A | 5/1940 | Dawson |

(Continued)

FOREIGN PATENT DOCUMENTS

DE 21 99 99 3/1910

(Continued)

OTHER PUBLICATIONS

International Preliminary Examination Report PCT/US02/10866 dated Oct. 1, 2003.

(Continued)

*Primary Examiner* — Patricia Bianco
*Assistant Examiner* — Nihir Patel

(57) ABSTRACT

A novel bridge clip tissue connector includes two clips separated by a bridge portion. The clips allow for the connecting of tissue at two positions that are maintained by the bridge portion. The connector can be used for performing a wide variety of surgical procedures, including anastomosis and a horizontal mattress suture-like connection.

25 Claims, 24 Drawing Sheets

U.S. PATENT DOCUMENTS

| | | |
|---|---|---|
| 2,240,330 A | 4/1941 | Flagg et al. |
| 2,256,382 A | 9/1941 | Dole |
| 2,264,679 A | 12/1941 | Ravel |
| 2,413,142 A | 12/1946 | Jones et al. |
| 2,430,293 A | 11/1947 | Howells |
| 2,505,358 A | 4/1950 | Gusberg et al. |
| 2,516,710 A | 7/1950 | Mascolo |
| 2,715,486 A | 8/1955 | Marcoff-Moghadam et al. |
| 2,890,519 A | 6/1959 | Storz, Jr. |
| 2,940,452 A | 6/1960 | Smialowski |
| 3,055,689 A | 9/1962 | Jorgensen |
| 3,057,355 A | 10/1962 | Smialowski |
| 3,082,426 A | 3/1963 | Miles |
| 3,143,742 A | 8/1964 | Cromie |
| 3,150,379 A | 9/1964 | Brown |
| 3,180,337 A | 4/1965 | Smialowski |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| 3,656,185 A | 4/1972 | Carpentier |
| RE27,391 E | 6/1972 | Merser |
| 3,753,438 A | 8/1973 | Wood et al. |
| 3,762,418 A | 10/1973 | Wasson |
| 3,776,237 A | 12/1973 | Hill et al. |
| 3,802,438 A | 4/1974 | Wolvek |
| 3,825,009 A | 7/1974 | Williams |
| 3,837,345 A | 9/1974 | Matar |
| 3,874,388 A | 4/1975 | King et al. ............. 606/232 |
| 3,875,648 A | 4/1975 | Bone |
| 3,905,403 A | 9/1975 | Smith et al. |
| 3,908,662 A | 9/1975 | Razgulov et al. |
| 3,910,281 A | 10/1975 | Kletschka et al. |
| 3,958,576 A | 5/1976 | Komiya |
| 3,976,079 A | 8/1976 | Samuels |
| 3,995,619 A | 12/1976 | Glatzer |
| 4,006,747 A | 2/1977 | Kronenthal et al. |
| 4,018,228 A | 4/1977 | Goosen |
| 4,038,725 A | 8/1977 | Keefe |
| 4,042,979 A | 8/1977 | Angell |
| 4,073,179 A | 2/1978 | Hickey et al. |
| 4,103,690 A | 8/1978 | Harris |
| 4,111,206 A | 9/1978 | Vishnevsky et al. |
| 4,129,059 A | 12/1978 | Van Eck |
| 4,140,125 A | 2/1979 | Smith |
| 4,170,990 A | 10/1979 | Baumgart et al. |
| 4,185,636 A | 1/1980 | Gabbay et al. |
| 4,192,315 A | 3/1980 | Hilzinger et al. |
| 4,214,587 A | 7/1980 | Sakura, Jr. |
| 4,217,902 A | 8/1980 | March |
| 4,243,048 A | 1/1981 | Griffin |
| 4,324,248 A | 4/1982 | Perlin |
| 4,345,601 A | 8/1982 | Fukuda |
| 4,352,358 A | 10/1982 | Angelchik |
| 4,366,819 A | 1/1983 | Kaster |
| 4,396,139 A | 8/1983 | Hall et al. |
| 4,416,266 A | 11/1983 | Baucom |
| 4,456,017 A | 6/1984 | Miles |
| 4,465,071 A | 8/1984 | Samuels et al. |
| 4,470,415 A | 9/1984 | Wozniak |
| 4,470,533 A | 9/1984 | Schuler |
| 4,474,181 A | 10/1984 | Schenck |
| 4,485,816 A | 12/1984 | Krumme |
| 4,492,229 A | 1/1985 | Grunwald |
| 4,522,207 A | 6/1985 | Klieman et al. |
| 4,523,592 A | 6/1985 | Daniel |
| 4,532,927 A | 8/1985 | Miksza |
| 4,535,764 A | 8/1985 | Ebert |
| 4,549,545 A | 10/1985 | Levy |
| 4,553,542 A | 11/1985 | Schenck et al. |
| 4,576,605 A | 3/1986 | Kaidash et al. |
| 4,586,502 A | 5/1986 | Bedi et al. |
| 4,586,503 A | 5/1986 | Kirsch et al. |
| 4,593,693 A | 6/1986 | Schenck |
| 4,595,007 A | 6/1986 | Mericle |
| 4,612,932 A | 9/1986 | Caspar et al. |
| 4,622,970 A | 11/1986 | Wozniak |
| 4,624,255 A | 11/1986 | Schenck et al. |
| 4,637,380 A | 1/1987 | Orejola |
| 4,641,652 A | 2/1987 | Hutterer et al. |
| 4,653,496 A | 3/1987 | Bundy et al. |
| 4,665,906 A | 5/1987 | Jervis |
| 4,665,917 A | 5/1987 | Clanton et al. |
| 4,683,895 A | 8/1987 | Pohndorf |
| 4,706,362 A | 11/1987 | Strausburg |
| 4,719,917 A | 1/1988 | Barrows et al. |
| 4,719,924 A | 1/1988 | Crittenden et al. |
| 4,730,615 A | 3/1988 | Sutherland et al. |
| 4,732,151 A | 3/1988 | Jones |
| 4,809,695 A | 3/1989 | Gwathmey et al. |
| 4,820,298 A | 4/1989 | Leveen et al. |
| 4,844,318 A | 7/1989 | Kunreuther |
| 4,873,975 A | 10/1989 | Walsh et al. |
| 4,890,615 A | 1/1990 | Caspari et al. |
| 4,896,668 A | 1/1990 | Popoff et al. |
| 4,899,744 A | 2/1990 | Fujitsuka et al. |
| 4,901,721 A | 2/1990 | Hakki |
| 4,923,461 A | 5/1990 | Caspari et al. |
| 4,924,866 A | 5/1990 | Yoon |
| 4,926,860 A | 5/1990 | Stice et al. |
| 4,929,240 A | 5/1990 | Kirsch et al. |
| 4,930,674 A | 6/1990 | Barak |
| 4,932,955 A | 6/1990 | Merz et al. |
| 4,935,027 A | 6/1990 | Yoon |
| 4,950,015 A | 8/1990 | Nejib et al. |
| 4,950,283 A | 8/1990 | Dzubow et al. |
| 4,950,285 A | 8/1990 | Wilk |
| 4,957,498 A | 9/1990 | Caspari et al. |
| 4,983,176 A | 1/1991 | Cushman et al. |
| 4,990,152 A | 2/1991 | Yoon |
| 4,991,567 A | 2/1991 | McCuen et al. |
| 4,994,069 A * | 2/1991 | Ritchart et al. ............. 606/191 |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,007,920 A | 4/1991 | Torre |
| 5,011,481 A | 4/1991 | Myers et al. |
| 5,020,713 A | 6/1991 | Kunreuther |
| 5,026,379 A | 6/1991 | Yoon |
| 5,032,127 A | 7/1991 | Frazee et al. |
| 5,035,692 A | 7/1991 | Lyon et al. |
| 5,035,702 A | 7/1991 | Taheri |
| 5,042,707 A | 8/1991 | Taheri |
| 5,047,047 A | 9/1991 | Yoon |
| 5,053,047 A | 10/1991 | Yoon |
| 5,064,431 A | 11/1991 | Gilbertson et al. |
| 5,074,874 A | 12/1991 | Yoon et al. |
| 5,088,692 A | 2/1992 | Weiler |
| 5,100,418 A | 3/1992 | Yoon |
| 5,100,421 A | 3/1992 | Christoudias |
| 5,104,407 A | 4/1992 | Lam et al. |
| 5,119,983 A | 6/1992 | Green et al. |
| 5,123,913 A | 6/1992 | Wilk et al. |
| 5,127,413 A | 7/1992 | Ebert |
| 5,129,913 A | 7/1992 | Ruppert |
| 5,152,769 A | 10/1992 | Baber |
| 5,154,189 A | 10/1992 | Oberlander |
| 5,158,566 A | 10/1992 | Pianetti |
| 5,171,250 A | 12/1992 | Yoon |
| 5,171,252 A | 12/1992 | Friedland |
| 5,174,087 A | 12/1992 | Bruno |
| 5,178,634 A | 1/1993 | Ramos Martinez |
| 5,192,294 A | 3/1993 | Blake |
| 5,196,022 A | 3/1993 | Bilweis |
| 5,201,880 A | 4/1993 | Wright et al. |
| 5,207,694 A | 5/1993 | Broome |
| 5,217,027 A | 6/1993 | Hermens |
| 5,219,358 A | 6/1993 | Bendel et al. |
| 5,221,259 A | 6/1993 | Weldon et al. |
| 5,222,961 A | 6/1993 | Nakao et al. |
| 5,222,976 A | 6/1993 | Yoon |

| Patent No. | Date | Inventor |
|---|---|---|
| 5,234,447 A | 8/1993 | Kaster et al. |
| 5,236,440 A | 8/1993 | Hlavacek |
| 5,242,456 A | 9/1993 | Nash et al. |
| 5,242,457 A | 9/1993 | Akopov et al. |
| 5,246,443 A | 9/1993 | Mai |
| 5,250,053 A | 10/1993 | Snyder |
| 5,258,011 A | 11/1993 | Drews |
| 5,261,917 A | 11/1993 | Hasson et al. |
| 5,269,783 A | 12/1993 | Sander |
| 5,269,809 A | 12/1993 | Hayhurst et al. |
| 5,282,825 A | 2/1994 | Muck et al. |
| 5,290,289 A | 3/1994 | Sanders et al. |
| 5,304,117 A | 4/1994 | Wilk |
| 5,304,204 A | 4/1994 | Bregen et al. |
| 5,306,296 A | 4/1994 | Wright et al. |
| 5,312,436 A | 5/1994 | Coffey et al. |
| 5,314,468 A | 5/1994 | Ramos Martinez |
| 5,330,503 A | 7/1994 | Yoon |
| 5,334,196 A | 8/1994 | Scott et al. |
| 5,336,233 A | 8/1994 | Chen |
| 5,336,239 A | 8/1994 | Gimpelson |
| 5,346,459 A | 9/1994 | Allen |
| 5,350,420 A | 9/1994 | Cosgrove et al. |
| 5,353,804 A | 10/1994 | Kornberg et al. |
| 5,355,897 A | 10/1994 | Pietrafitta et al. |
| 5,356,424 A | 10/1994 | Buzerak et al. |
| 5,364,406 A | 11/1994 | Sewell |
| 5,366,459 A | 11/1994 | Yoon |
| 5,366,462 A | 11/1994 | Kaster et al. |
| 5,366,479 A | 11/1994 | McGarry et al. |
| 5,374,268 A * | 12/1994 | Sander ............ 606/72 |
| 5,376,096 A | 12/1994 | Foster |
| 5,382,259 A | 1/1995 | Phelps et al. |
| 5,383,904 A | 1/1995 | Totakura et al. |
| 5,387,227 A | 2/1995 | Grice |
| 5,403,331 A | 4/1995 | Chesterfield et al. |
| 5,403,333 A | 4/1995 | Kaster et al. |
| 5,403,338 A | 4/1995 | Milo |
| 5,403,346 A | 4/1995 | Loeser |
| 5,413,584 A | 5/1995 | Schulze |
| 5,417,684 A | 5/1995 | Jackson et al. |
| 5,417,700 A | 5/1995 | Egan |
| 5,423,821 A | 6/1995 | Pasque |
| 5,431,666 A | 7/1995 | Sauer et al. |
| 5,437,680 A | 8/1995 | Yoon |
| 5,437,681 A | 8/1995 | Meade et al. |
| 5,437,685 A | 8/1995 | Blasnik |
| 5,439,479 A | 8/1995 | Shichman et al. |
| 5,445,167 A | 8/1995 | Yoon et al. |
| 5,445,644 A | 8/1995 | Pietrafitta et al. |
| 5,450,860 A | 9/1995 | O'Connor |
| 5,451,231 A | 9/1995 | Rabenau et al. |
| 5,452,733 A | 9/1995 | Sterman et al. |
| 5,454,834 A * | 10/1995 | Boebel et al. ............ 606/228 |
| 5,456,246 A | 10/1995 | Schmieding et al. |
| 5,462,561 A | 10/1995 | Voda |
| 5,474,557 A | 12/1995 | Mai |
| 5,480,405 A | 1/1996 | Yoon |
| 5,486,187 A | 1/1996 | Schenck |
| 5,486,197 A | 1/1996 | Le et al. |
| 5,488,958 A | 2/1996 | Topel et al. |
| 5,496,334 A | 3/1996 | Klundt et al. |
| 5,499,990 A | 3/1996 | Schulken et al. |
| 5,500,000 A | 3/1996 | Feagin et al. |
| 5,522,884 A | 6/1996 | Wright |
| 5,527,342 A | 6/1996 | Pietrzak et al. |
| 5,533,236 A | 7/1996 | Tseng |
| 5,538,509 A | 7/1996 | Dunlap et al. |
| 5,545,214 A | 8/1996 | Stevens |
| 5,549,619 A | 8/1996 | Peters et al. |
| 5,556,411 A | 9/1996 | Taoda et al. |
| 5,562,685 A | 10/1996 | Mollenauer et al. |
| 5,569,205 A | 10/1996 | Hart et al. |
| 5,569,274 A | 10/1996 | Rapacki et al. |
| 5,569,301 A | 10/1996 | Granger et al. |
| 5,571,119 A | 11/1996 | Atala |
| 5,571,175 A | 11/1996 | Vanney et al. |
| 5,582,616 A | 12/1996 | Bolduc et al. |
| 5,582,619 A | 12/1996 | Ken |
| 5,584,879 A | 12/1996 | Reimold et al. |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,597,378 A | 1/1997 | Jervis |
| 5,601,571 A | 2/1997 | Moss |
| 5,601,572 A | 2/1997 | Middleman et al. |
| 5,601,600 A | 2/1997 | Ton |
| 5,603,718 A | 2/1997 | Xu |
| 5,609,608 A | 3/1997 | Benett et al. |
| 5,618,311 A | 4/1997 | Gryskiewicz |
| 5,628,757 A | 5/1997 | Hasson |
| 5,630,540 A | 5/1997 | Blewett |
| 5,632,752 A | 5/1997 | Buelna |
| 5,632,753 A | 5/1997 | Loeser |
| 5,643,295 A | 7/1997 | Yoon |
| 5,643,305 A | 7/1997 | Al-Tameem |
| 5,645,568 A * | 7/1997 | Chervitz et al. ............ 606/228 |
| 5,653,716 A | 8/1997 | Malo et al. |
| 5,653,718 A | 8/1997 | Yoon |
| 5,658,312 A | 8/1997 | Green et al. |
| 5,660,186 A | 8/1997 | Bachir |
| 5,665,109 A | 9/1997 | Yoon |
| 5,669,918 A | 9/1997 | Balazs et al. |
| 5,676,670 A | 10/1997 | Kim |
| 5,683,417 A | 11/1997 | Cooper |
| 5,690,662 A | 11/1997 | Chiu et al. |
| 5,695,504 A | 12/1997 | Gifford, III et al. |
| 5,695,505 A | 12/1997 | Yoon |
| 5,697,913 A | 12/1997 | Sierocuk et al. |
| 5,697,943 A | 12/1997 | Sauer et al. |
| 5,700,270 A | 12/1997 | Peyser et al. |
| 5,700,271 A | 12/1997 | Whitfield et al. |
| 5,702,412 A | 12/1997 | Popov et al. |
| 5,707,362 A | 1/1998 | Yoon |
| 5,707,380 A | 1/1998 | Hinchliffe et al. |
| 5,709,693 A | 1/1998 | Taylor |
| 5,709,695 A | 1/1998 | Northrup, III |
| 5,715,987 A | 2/1998 | Kelley et al. |
| 5,716,370 A | 2/1998 | Williamson, IV et al. |
| 5,720,755 A | 2/1998 | Dakov |
| 5,725,539 A | 3/1998 | Matern |
| 5,725,542 A | 3/1998 | Yoon |
| 5,725,554 A | 3/1998 | Simon et al. |
| 5,728,135 A | 3/1998 | Bregen et al. |
| 5,732,872 A | 3/1998 | Bolduc et al. |
| 5,735,290 A | 4/1998 | Sterman et al. |
| 5,746,753 A | 5/1998 | Sullivan et al. |
| 5,755,778 A | 5/1998 | Kleshinski |
| 5,766,189 A | 6/1998 | Matsumo |
| 5,769,870 A | 6/1998 | Salahieh et al. |
| 5,779,718 A | 7/1998 | Green et al. |
| 5,782,397 A | 7/1998 | Koukline |
| 5,782,844 A | 7/1998 | Yoon et al. |
| 5,797,920 A | 8/1998 | Kim |
| 5,797,933 A | 8/1998 | Snow et al. |
| 5,797,934 A | 8/1998 | Rygaard |
| 5,797,960 A | 8/1998 | Stevens et al. |
| 5,799,661 A | 9/1998 | Boyd et al. |
| 5,799,857 A | 9/1998 | Robertson et al. |
| 5,810,848 A | 9/1998 | Hayhurst |
| 5,810,851 A | 9/1998 | Yoon |
| 5,810,853 A | 9/1998 | Yoon |
| 5,810,882 A | 9/1998 | Bolduc et al. |
| 5,817,113 A | 10/1998 | Gifford, III et al. |
| 5,820,631 A | 10/1998 | Nobles |
| 5,824,002 A | 10/1998 | Gentelia et al. |
| 5,824,008 A | 10/1998 | Bolduc et al. |
| 5,827,265 A | 10/1998 | Glinsky et al. |
| 5,827,316 A | 10/1998 | Young et al. |
| 5,830,221 A | 11/1998 | Stein et al. |
| 5,830,222 A | 11/1998 | Makower |
| 5,833,698 A | 11/1998 | Hinchliffe |
| 5,849,019 A | 12/1998 | Yoon |
| 5,851,216 A | 12/1998 | Allen |
| 5,855,614 A | 1/1999 | Stevens et al. |
| 5,868,702 A | 2/1999 | Stevens et al. |
| 5,868,763 A | 2/1999 | Spence et al. |

| | | |
|---|---|---|
| 5,871,528 A | 2/1999 | Camps et al. |
| 5,879,371 A | 3/1999 | Gardiner et al. |
| 5,881,943 A | 3/1999 | Heck et al. |
| 5,882,340 A | 3/1999 | Yoon |
| 5,891,130 A | 4/1999 | Palermo et al. |
| 5,891,160 A | 4/1999 | Williamson, IV et al. |
| 5,893,369 A | 4/1999 | LeMole |
| 5,893,856 A | 4/1999 | Jacob et al. |
| 5,893,865 A | 4/1999 | Swindle et al. |
| 5,893,886 A | 4/1999 | Zegdi et al. |
| 5,895,394 A | 4/1999 | Kienzle et al. |
| 5,904,697 A | 5/1999 | Gifford, III et al. |
| 5,908,428 A | 6/1999 | Scirica et al. |
| 5,911,352 A | 6/1999 | Racenet et al. |
| 5,919,207 A | 7/1999 | Taheri |
| 5,931,842 A | 8/1999 | Goldsteen et al. |
| 5,941,434 A | 8/1999 | Green |
| 5,941,442 A | 8/1999 | Geiste et al. |
| 5,941,888 A * | 8/1999 | Wallace et al. .............. 606/108 |
| 5,941,908 A | 8/1999 | Goldsteen et al. |
| 5,944,730 A | 8/1999 | Nobles et al. |
| 5,951,576 A | 9/1999 | Wakabayashi |
| 5,951,600 A | 9/1999 | Lemelson |
| 5,954,732 A | 9/1999 | Hart et al. |
| 5,954,735 A | 9/1999 | Rygaard |
| 5,957,363 A | 9/1999 | Heck |
| 5,957,938 A | 9/1999 | Zhu et al. |
| 5,957,940 A | 9/1999 | Tanner et al. |
| 5,961,481 A | 10/1999 | Sterman et al. |
| 5,961,539 A | 10/1999 | Northrup, III et al. |
| 5,964,772 A | 10/1999 | Bolduc et al. |
| 5,964,782 A | 10/1999 | Lafontaine et al. |
| 5,972,004 A | 10/1999 | Williamson, IV et al. |
| 5,972,024 A | 10/1999 | Northrup, III et al. |
| 5,976,159 A | 11/1999 | Bolduc et al. |
| 5,976,161 A | 11/1999 | Kirsch et al. |
| 5,976,164 A | 11/1999 | Bencini et al. |
| 5,976,178 A | 11/1999 | Goldsteen et al. |
| 5,984,917 A | 11/1999 | Fleischman et al. |
| 5,984,959 A | 11/1999 | Robertson et al. |
| 5,989,242 A | 11/1999 | Saadat et al. |
| 5,989,268 A | 11/1999 | Pugsley, Jr. et al. |
| 5,989,276 A | 11/1999 | Houser et al. |
| 5,989,278 A | 11/1999 | Mueller |
| 5,993,465 A | 11/1999 | Shipp et al. |
| 5,993,468 A | 11/1999 | Rygaard |
| 5,997,556 A | 12/1999 | Tanner |
| 6,001,110 A | 12/1999 | Adams |
| 6,007,544 A | 12/1999 | Kim |
| 6,010,531 A | 1/2000 | Donlon et al. |
| 6,013,084 A | 1/2000 | Ken et al. |
| 6,022,367 A | 2/2000 | Sherts |
| 6,024,748 A | 2/2000 | Manzo et al. |
| 6,032,849 A | 3/2000 | Mastri et al. |
| 6,033,419 A | 3/2000 | Hamblin, Jr. et al. |
| 6,036,699 A | 3/2000 | Andreas et al. |
| 6,036,703 A | 3/2000 | Evans et al. |
| 6,036,710 A | 3/2000 | McGarry et al. |
| 6,042,607 A | 3/2000 | Williamson et al. |
| 6,047,607 A | 4/2000 | Weber et al. |
| 6,056,751 A | 5/2000 | Fenton |
| 6,063,070 A | 5/2000 | Eder |
| 6,066,148 A | 5/2000 | Rygaard |
| 6,074,401 A | 6/2000 | Gardiner et al. |
| 6,074,418 A | 6/2000 | Buchanan et al. |
| 6,077,291 A | 6/2000 | Das |
| 6,080,114 A | 6/2000 | Russin |
| 6,083,237 A | 7/2000 | Huitema et al. |
| 6,106,538 A | 8/2000 | Shiber |
| 6,110,188 A | 8/2000 | Narciso |
| 6,113,611 A | 9/2000 | Allen et al. |
| 6,113,612 A | 9/2000 | Swanson et al. |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,149,658 A | 11/2000 | Gardiner et al. |
| 6,152,935 A | 11/2000 | Kammerer et al. |
| 6,152,937 A | 11/2000 | Peterson et al. .............. 606/153 |
| 6,159,165 A | 12/2000 | Ferrera et al. |
| 6,159,225 A | 12/2000 | Makower |
| 6,162,233 A | 12/2000 | Williamson, IV et al. |
| 6,165,183 A | 12/2000 | Kuehn et al. |
| 6,165,185 A | 12/2000 | Shennib et al. |
| 6,171,320 B1 | 1/2001 | Monassevitch |
| 6,171,321 B1 | 1/2001 | Gifford, III et al. |
| 6,176,413 B1 | 1/2001 | Heck et al. |
| 6,176,864 B1 | 1/2001 | Chapman |
| 6,179,840 B1 | 1/2001 | Bowman |
| 6,179,848 B1 | 1/2001 | Solem |
| 6,179,849 B1 | 1/2001 | Yencho et al. |
| 6,183,512 B1 | 2/2001 | Howanec et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,197,037 B1 | 3/2001 | Hair |
| 6,217,611 B1 | 4/2001 | Klostermeyer .............. 623/2.38 |
| 6,221,083 B1 | 4/2001 | Mayer |
| 6,241,738 B1 | 6/2001 | Dereume |
| 6,241,741 B1 | 6/2001 | Duhaylongsod et al. |
| 6,248,117 B1 | 6/2001 | Blatter |
| 6,250,308 B1 | 6/2001 | Cox |
| 6,254,615 B1 * | 7/2001 | Bolduc et al. .............. 606/142 |
| 6,269,819 B1 | 8/2001 | Oz et al. |
| 6,280,460 B1 | 8/2001 | Bolduc et al. |
| 6,283,979 B1 | 9/2001 | Mers Kelly et al. |
| 6,283,993 B1 | 9/2001 | Cosgrove et al. |
| 6,296,622 B1 | 10/2001 | Kurz et al. |
| 6,296,656 B1 | 10/2001 | Bolduc et al. |
| 6,306,141 B1 | 10/2001 | Jervis |
| 6,332,893 B1 | 12/2001 | Mortier et al. |
| 6,346,074 B1 | 2/2002 | Roth |
| 6,346,112 B2 | 2/2002 | Adams |
| 6,350,269 B1 | 2/2002 | Shipp et al. |
| 6,352,543 B1 | 3/2002 | Cole |
| 6,358,258 B1 | 3/2002 | Arcia et al. |
| 6,361,559 B1 | 3/2002 | Houser et al. |
| 6,368,348 B1 | 4/2002 | Gabbay |
| 6,371,964 B1 | 4/2002 | Vargas et al. |
| 6,387,105 B1 | 5/2002 | Gifford, III et al. |
| 6,391,038 B2 | 5/2002 | Vargas et al. |
| 6,402,764 B1 | 6/2002 | Hendricksen et al. |
| 6,406,492 B1 | 6/2002 | Lytle |
| 6,406,493 B1 | 6/2002 | Tu et al. |
| 6,409,739 B1 | 6/2002 | Nobles et al. |
| 6,409,758 B2 | 6/2002 | Stobie et al. |
| 6,416,527 B1 | 7/2002 | Berg et al. |
| 6,418,597 B1 | 7/2002 | Deschenes et al. |
| 6,419,658 B1 | 7/2002 | Restelli et al. |
| 6,419,681 B1 | 7/2002 | Vargas et al. |
| 6,419,695 B1 | 7/2002 | Gabbay |
| 6,425,900 B1 | 7/2002 | Knodel et al. |
| 6,428,550 B1 | 8/2002 | Vargas et al. |
| 6,428,555 B1 | 8/2002 | Koster, Jr. |
| 6,451,048 B1 | 9/2002 | Berg et al. .............. 623/1.13 |
| 6,461,320 B1 | 10/2002 | Yencho et al. |
| 6,475,222 B1 | 11/2002 | Berg et al. |
| 6,478,804 B2 | 11/2002 | Vargas et al. |
| 6,485,496 B1 | 11/2002 | Suyker et al. |
| 6,491,707 B2 | 12/2002 | Makower et al. |
| 6,497,671 B2 | 12/2002 | Ferrera et al. |
| 6,497,710 B2 | 12/2002 | Yencho et al. |
| 6,514,265 B2 * | 2/2003 | Ho et al. .............. 606/157 |
| 6,517,558 B2 | 2/2003 | Gittings et al. |
| 6,524,338 B1 | 2/2003 | Gundry |
| 6,533,812 B2 | 3/2003 | Swanson et al. |
| 6,537,248 B2 | 3/2003 | Mulier et al. |
| 6,537,288 B2 | 3/2003 | Vargas et al. |
| 6,547,799 B2 | 4/2003 | Hess et al. |
| 6,551,332 B1 * | 4/2003 | Nguyen et al. .............. 606/151 |
| 6,562,053 B2 | 5/2003 | Schulze |
| 6,575,985 B2 | 6/2003 | Knight et al. |
| 6,589,255 B2 | 7/2003 | Schulze et al. |
| 6,607,541 B1 * | 8/2003 | Gardiner et al. .............. 606/151 |
| 6,607,542 B1 | 8/2003 | Wild et al. |
| 6,613,059 B2 | 9/2003 | Schaller et al. |
| 6,629,988 B2 | 10/2003 | Weadock |
| 6,635,214 B2 | 10/2003 | Rapacki et al. |

| | | |
|---|---|---|
| 6,641,593 B1 | 11/2003 | Schaller et al. |
| 6,648,900 B2 | 11/2003 | Fleischman et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,541 B1 | 11/2003 | Vargas et al. |
| 6,660,015 B1 | 12/2003 | Berg et al. ............... 606/153 |
| 6,682,540 B1 | 1/2004 | Sancoff et al. |
| 6,695,859 B1 | 2/2004 | Golden et al. |
| 6,702,826 B2 | 3/2004 | Liddicoat et al. ........... 606/151 |
| 6,709,442 B2 | 3/2004 | Miller et al. |
| 6,712,829 B2 | 3/2004 | Schulze |
| 6,719,768 B1 | 4/2004 | Cole et al. |
| 6,743,243 B1 | 6/2004 | Roy et al. |
| 6,749,622 B2 | 6/2004 | McGuckin et al. |
| 6,776,782 B2 | 8/2004 | Schulze |
| 6,776,784 B2 | 8/2004 | Ginn |
| 6,776,785 B1 | 8/2004 | Yencho et al. ................ 606/153 |
| 6,802,847 B1 | 10/2004 | Carson et al. |
| 6,821,286 B1 | 11/2004 | Carranza et al. |
| 6,869,444 B2 | 3/2005 | Gabbay |
| 6,913,607 B2 | 7/2005 | Ainsworth |
| 6,918,917 B1 | 7/2005 | Nguyen |
| 6,921,407 B2 | 7/2005 | Nguyen et al. |
| 6,926,730 B1 | 8/2005 | Nguyen |
| 6,945,980 B2 | 9/2005 | Nguyen |
| 6,955,679 B1 | 10/2005 | Hendricksen et al. |
| 6,960,221 B2 | 11/2005 | Ho et al. |
| 6,979,337 B2 | 12/2005 | Kato |
| 6,979,338 B1 | 12/2005 | Loshakove et al. |
| 7,022,131 B1 | 4/2006 | Derowe et al. |
| 7,056,330 B2 | 6/2006 | Gayton |
| 7,063,711 B1 | 6/2006 | Loshakove et al. |
| 7,070,618 B2 | 7/2006 | Streeter |
| 7,104,949 B2 | 9/2006 | Anderson et al. |
| 7,182,769 B2 | 2/2007 | Ainsworth et al. |
| 7,220,265 B2 | 5/2007 | Chanduszko et al. |
| 7,220,268 B2 | 5/2007 | Blatter |
| 7,335,212 B2 | 2/2008 | Edoga et al. |
| RE40,377 E | 6/2008 | Williamson, IV et al. |
| 7,547,313 B2 | 6/2009 | Gardiner et al. |
| 7,556,647 B2 | 7/2009 | Drews et al. |
| 7,722,643 B2 | 5/2010 | Schaller et al. |
| 7,744,611 B2 | 6/2010 | Nguyen et al. |
| 7,763,040 B2 | 7/2010 | Schaller et al. |
| 2001/0018592 A1 | 8/2001 | Schaller et al. |
| 2001/0018593 A1 | 8/2001 | Schaller et al. |
| 2001/0018611 A1 | 8/2001 | Solem et al. |
| 2001/0021856 A1 | 9/2001 | Bolduc et al. |
| 2001/0047181 A1 | 11/2001 | Ho et al. |
| 2002/0010490 A1 | 1/2002 | Schaller et al. |
| 2002/0042623 A1 | 4/2002 | Blatter et al. |
| 2002/0082614 A1 | 6/2002 | Logan et al. |
| 2002/0099395 A1 | 7/2002 | Acampora et al. |
| 2002/0151916 A1 | 10/2002 | Muramatsu et al. |
| 2002/0165561 A1 | 11/2002 | Ainsworth et al. |
| 2002/0173803 A1 | 11/2002 | Ainsworth |
| 2003/0074012 A1 | 4/2003 | Nguyen et al. |
| 2003/0078603 A1 | 4/2003 | Schaller et al. |
| 2003/0083742 A1 | 5/2003 | Spence et al. |
| 2003/0093118 A1 | 5/2003 | Ho et al. |
| 2003/0125755 A1 | 7/2003 | Schaller et al. |
| 2003/0191481 A1 | 10/2003 | Nguyen |
| 2003/0195531 A1 | 10/2003 | Gardiner et al. |
| 2003/0199974 A1 | 10/2003 | Lee |
| 2004/0044406 A1 | 3/2004 | Woolfson et al. |
| 2004/0050393 A1 | 3/2004 | Golden |
| 2004/0068276 A1 | 4/2004 | Golden |
| 2004/0093024 A1 | 5/2004 | Lousararian et al. |
| 2004/0102797 A1 | 5/2004 | Golden et al. |
| 2004/0111099 A1 | 6/2004 | Nguyen |
| 2004/0138685 A1 | 7/2004 | Clague et al. |
| 2004/0167573 A1 | 8/2004 | Williamson et al. |
| 2004/0176663 A1 | 9/2004 | Edoga |
| 2004/0193259 A1 | 9/2004 | Gabbay |
| 2005/0004582 A1 | 1/2005 | Edoga |
| 2005/0021054 A1 | 1/2005 | Ainsworth et al. |
| 2005/0043749 A1 | 2/2005 | Breton et al. |
| 2005/0065601 A1 | 3/2005 | Lee et al. |
| 2005/0070924 A1 | 3/2005 | Schaller |
| 2005/0075659 A1 | 4/2005 | Realyvasquez |
| 2005/0075667 A1 | 4/2005 | Schaller et al. |
| 2005/0080454 A1 | 4/2005 | Drews |
| 2005/0101975 A1 | 5/2005 | Nguyen et al. |
| 2005/0107871 A1 | 5/2005 | Realyvasquez |
| 2005/0131429 A1 | 6/2005 | Ho |
| 2005/0267572 A1 | 12/2005 | Schoon et al. |
| 2006/0004389 A1 | 1/2006 | Nguyen et al. |
| 2006/0122634 A1 | 6/2006 | Ino et al. |
| 2006/0253143 A1 | 11/2006 | Edoga |
| 2006/0271081 A1 | 11/2006 | Realyvasquez |
| 2006/0293701 A1 | 12/2006 | Ainsworth et al. |
| 2007/0010835 A1 | 1/2007 | Breton et al. |
| 2007/0027461 A1 | 2/2007 | Gardiner et al. |
| 2007/0106313 A1 | 5/2007 | Golden et al. |
| 2007/0142848 A1 | 6/2007 | Ainsworth et al. |
| 2008/0119875 A1 | 5/2008 | Ino et al. |
| 2009/0036903 A1 | 2/2009 | Ino et al. |
| 2009/0112233 A1 | 4/2009 | Xiao |
| 2009/0264903 A1 | 10/2009 | Lee et al. |
| 2010/0044410 A1 | 2/2010 | Argentine et al. |

FOREIGN PATENT DOCUMENTS

| | | |
|---|---|---|
| DE | 0219999 | 3/1910 |
| DE | 0377052 | 6/1923 |
| DE | 27 03 529 | 1/1977 |
| DE | 2703529 | 1/1977 |
| DE | 32 03 410 A1 | 5/1981 |
| DE | 3203410 | 5/1981 |
| DE | 32 27 984 A1 | 2/1984 |
| DE | 3227984 | 2/1984 |
| DE | 3504202 | 8/1985 |
| DE | 41 33 800 C1 | 10/1991 |
| DE | 4133800 | 10/1991 |
| DE | 44 02 058 C1 | 4/1995 |
| DE | 4402058 | 4/1995 |
| DE | 195 47 617 C1 | 9/1997 |
| DE | 19547617 | 9/1997 |
| DE | 197 11 288 | 10/1998 |
| DE | 19732234 | 1/1999 |
| EP | 0072232 | 2/1983 |
| EP | 0122046 | 3/1983 |
| EP | 0129441 | 12/1984 |
| EP | 0130037 | 1/1985 |
| EP | 0 140 557 A2 | 5/1985 |
| EP | 0140557 | 5/1985 |
| EP | 0 121 362 B1 | 9/1987 |
| EP | 0121362 | 9/1987 |
| EP | 0409569 | 1/1991 |
| EP | 0 432 692 A1 | 6/1991 |
| EP | 0432692 | 6/1991 |
| EP | 0 478 949 B1 | 8/1991 |
| EP | 0478949 | 8/1991 |
| EP | 0 494 636 A1 | 7/1992 |
| EP | 0494636 | 7/1992 |
| EP | 0 537 955 B1 | 4/1993 |
| EP | 0537955 | 4/1993 |
| EP | 0 559 429 A1 | 9/1993 |
| EP | 0559429 | 9/1993 |
| EP | 0598529 | 5/1994 |
| EP | 0 326 426 B1 | 12/1994 |
| EP | 0 419 597 B1 | 12/1994 |
| EP | 0326426 | 12/1994 |
| EP | 0419597 | 12/1994 |
| EP | 0632999 | 1/1995 |
| EP | 0 641 546 A1 | 3/1995 |
| EP | 0641546 | 3/1995 |
| EP | 0656191 | 6/1995 |
| EP | 0687446 | 12/1995 |
| EP | 0705568 | 4/1996 |
| EP | 0 711 532 A1 | 5/1996 |
| EP | 0711532 | 5/1996 |
| EP | 0 734 697 A2 | 10/1996 |
| EP | 0705569 | 10/1996 |
| EP | 0734697 | 10/1996 |
| EP | 0 778 005 A1 | 6/1997 |
| EP | 0778005 | 6/1997 |
| EP | 0 815 795 A1 | 1/1998 |

| | | |
|---|---|---|
| EP | 0815795 | 1/1998 |
| EP | 0 826 340 | 3/1998 |
| FR | 320 731 | 12/1902 |
| GB | 2 223 410 A | 4/1990 |
| GB | 2223410 | 4/1990 |
| JP | 07308322 | 11/1995 |
| JP | 08336544 | 12/1996 |
| JP | 10337291 | 12/1998 |
| RU | 2110222 | 5/1998 |
| RU | 2110222 C1 | 5/1998 |
| SU | 577022 | 10/1977 |
| SU | 1186199 | 10/1985 |
| SU | 1186199 A | 10/1985 |
| SU | 1456109 | 2/1989 |
| SU | 1456109 A1 | 2/1989 |
| SU | 1560133 | 4/1990 |
| SU | 1560133 A1 | 4/1990 |
| WO | 90/06725 | 6/1990 |
| WO | WO 90/06725 A1 | 6/1990 |
| WO | 90/09149 | 8/1990 |
| WO | WO 90/09149 A1 | 8/1990 |
| WO | 90/14795 | 12/1990 |
| WO | WO 90/14795 A1 | 12/1990 |
| WO | 91/07916 | 6/1991 |
| WO | 91/08708 | 6/1991 |
| WO | WO 91/07916 A1 | 6/1991 |
| WO | 91/17712 | 11/1991 |
| WO | WO 91/17712 A1 | 11/1991 |
| WO | 92/05828 | 4/1992 |
| WO | WO 92/05828 A1 | 4/1992 |
| WO | 92/12676 | 8/1992 |
| WO | 92/22041 | 12/1992 |
| WO | 93/01750 | 2/1993 |
| WO | 94/15535 | 7/1994 |
| WO | 94/15537 | 7/1994 |
| WO | WO 94/15535 A1 | 7/1994 |
| WO | WO 94/15537 A1 | 7/1994 |
| WO | 96/00035 | 1/1996 |
| WO | WO 96/00035 A1 | 1/1996 |
| WO | 96/06565 | 3/1996 |
| WO | WO 96/06565 A1 | 3/1996 |
| WO | 96/38090 | 12/1996 |
| WO | WO 96/38090 A1 | 12/1996 |
| WO | 97/12555 | 4/1997 |
| WO | 97/16122 | 5/1997 |
| WO | 97/27898 | 8/1997 |
| WO | 97/28744 | 8/1997 |
| WO | WO 97/28744 A1 | 8/1997 |
| WO | 97/31575 | 9/1997 |
| WO | 97/32526 | 9/1997 |
| WO | WO 97/32526 A1 | 9/1997 |
| WO | 97/40754 | 11/1997 |
| WO | 97/42881 | 11/1997 |
| WO | WO 97/42881 A1 | 11/1997 |
| WO | 98/19636 | 5/1998 |
| WO | 98/30153 | 7/1998 |
| WO | WO 98/30153 A1 | 7/1998 |
| WO | 98/42262 | 10/1998 |
| WO | WO 98/42262 A1 | 10/1998 |
| WO | 98/48707 | 11/1998 |
| WO | 98/52475 | 11/1998 |
| WO | 99/07294 | 2/1999 |
| WO | 99/12484 | 3/1999 |
| WO | 99/15088 | 4/1999 |
| WO | 99/37218 | 7/1999 |
| WO | 99/62406 | 12/1999 |
| WO | 99/62408 | 12/1999 |
| WO | 99/62409 | 12/1999 |
| WO | 99/62415 | 12/1999 |
| WO | 99/63910 | 12/1999 |
| WO | 99/65409 | 12/1999 |
| WO | 00/03759 | 1/2000 |
| WO | 00/15144 | 3/2000 |
| WO | 00/44311 | 8/2000 |
| WO | 00/59380 | 10/2000 |
| WO | 00/60995 | 10/2000 |
| WO | 00/64381 | 11/2000 |
| WO | 00/74603 | 12/2000 |
| WO | 01/10310 | 2/2001 |
| WO | 01/19292 | 3/2001 |
| WO | 01/26557 | 4/2001 |
| WO | 01/26586 | 4/2001 |
| WO | 01/28432 | 4/2001 |
| WO | 01/54618 | 8/2001 |
| WO | 01/74254 | 10/2001 |
| WO | 01/82840 | 11/2001 |
| WO | 02/13701 | 2/2002 |
| WO | 02/13702 | 2/2002 |
| WO | WO 02/13702 A1 | 2/2002 |
| WO | 02/30295 | 4/2002 |
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/053289 | 7/2003 |
| WO | 03/088875 | 10/2003 |
| WO | 2005/011468 | 2/2005 |
| WO | 2005/041784 | 5/2005 |
| WO | 2005/058170 | 6/2005 |
| WO | 2006/060594 | 6/2006 |
| WO | 2007/067942 | 2/2007 |
| WO | 2009/137517 | 11/2009 |

OTHER PUBLICATIONS

Emery et al. "Suture Techniques for MIDCAB Surgery" Chapt. 12, pp. 87-91, 1997.
"VCS Clip Applier System, "published in 1995 by Auto Suture Company, a Division of U.S. Surgical Corporation (8 pages).
Wylie et al., Edwin J., Manual of Vascular Surgery, (Springer-Verlag New York), (1980) Table of contents only.
International Search Report PCT/US99/12563, dated Jun. 3, 1998.
Written Opinion PCT/US99/12563 dated Jun. 12, 2000.
International Search Report PCT/US99/12566, dated Mar. 6, 1998.
Written Opinion PCT/US99/12566 dated Jul. 28, 2000.
International Search Report PCT/US02/10866, dated Apr. 5, 2001.
Written Opinion PCT/US02/10866 dated Apr. 15, 2003.
US 6,503,260, Jan. 2003, Schaller, et al. (withdrawn).
"VCS Clip Applier System," published in 1995 by Auto Suture Company, a Division of U.S. Surgical Corporation.
Chitwood Jr., Mitral Valve Repair: Ischemic, Mastery of Cardiothoracic Surgery, Lippencott-Raven Publishers, 1998, Chapter 32, pp. 309-321.
Emery, et al., Suture Techniques for MIDCAB Surgery, Techniques for Minimally Invasive Direct Coronary Artery Bypass (MIDCAB) Surgery, R.W. Emery ed., Hanley & Belfus, Inc.: Philadelphia, PA, Chapter 12, 1997, pp. 87-91.
Grondin, et al., Carpentier's Annulus and De Vega's Annuloplasty: The end of the tricuspid challenge, Nov. 1975, vol. 70, pp. 852-861.
Holper, et al., Surgery for Tricuspid Insufficiency: Long Term Follow-Up After De Vega Annuloplasty, Thorac Cardiovasc Surgeon, 41, 1993.
Maisano, et al., The Double Orifice Technique as a Standardized Approach to Treat Mitral Regurgitation Due to Severe Myxomatous Disease: Surgical Technique, European Journal of Cardiothoracic Surgery, vol. 17, 2000, 201-205.
Rabago, et al., The New De Vega Technique in Tricuspid Annuloplasty: Results in 150 patients, J. Cardiovas Surg. 1980, 21 pp. 231-238.
Rivera, et al., Carpentier's Flexible Ring Versus De Vega's Annuloplasty, J Thorac Cardiovas Surg, Feb. 1985, 89 pp. 196-203.
Wei, et al., De Vega's Semicircular Annuloplasty for Tricuspid Valve Regurgitation, Ann Thorac Surg, 1993, 55: pp. 482-485.
Wylie, et al., Manual of Vascular Surgery, R. H. Egdahl ed. Spring-Verlag: New York, vol. II, 1986, Table of Contents only.
Wylie, et al., Manual of Vascular Surgery, Springer-Verlag New York, vol. I, 1980, Table of Contents only.
Yun, et al. Mitral Valve Replacement, Mastery of Cardiothoracic Surgery, Lippencott-Raven Publishers, 1998, Chapter 34, pp. 329-341.
International Search Report PCT/US98/00462 dated Jan. 9, 1997.
International Search Report PCT/US98/00795 dated Jul. 1, 1998.
International Search Report PCT/US98/14211 dated Jan. 6, 1998.

International Search Report PCT/US99/12563 dated Jun. 3, 1998.
International Search Report PCT/US99/12566 dated Jun. 3, 1998.
International Search Report PCT/US00/09092 dated Apr. 5, 1999.
International Search Report PCT/US01/10501 dated Mar. 29, 2001.
International Search Report PCT/US01/31709 dated Oct. 10, 2001.
International Search Report PCT/US01/42653 dated Oct. 10, 2001.
International Search Report PCT/US02/10865 dated Apr. 5, 2002.
International Search Report PCT/US02/10866 dated Apr. 5, 2001.
International Search Report PCT/US02/14261 dated May 1, 2002.
International Search Report PCT/US03/12073 dated Apr. 18, 2002.
International Preliminary Examination Report PCT/US98/00462, dated Jan. 9, 1997.
International Preliminary Examination Report PCT/US98/00795, dated Jan. 9, 1997.
International Preliminary Examination Report PCT/US99/12566, dated Jun. 3, 1998.
International Preliminary Examination Report PCT/US00/09092, dated Apr. 5, 2000.
International Preliminary Examination Report PCT/US01/31709, dated Oct. 10, 2003.
International Preliminary Examination Report PCT/US01/42653, dated Oct. 10, 2003.
International Preliminary Examination Report PCT/US02/14261, dated May 1, 2002.
International Preliminary Examination Report PCT/US02/10865, dated Apr. 5, 2002.
International Preliminary Examination Report PCT/US02/10866, dated May 1, 2002.
International Preliminary Examination Report PCT/US03/12073, dated May 1, 2002.
Written Opinion PCT/US99/12563, dated May 1, 2002.
Written Opinion PCT/US99/12566, dated Jun. 3, 1998.
Written Opinion PCT/US00/09092, dated Apr. 5, 1999.
Written Opinion PCT/US01/10501, dated Mar. 31, 2000.
Written Opinion PCT/US01/31709, dated Oct. 10, 2000.
Written Opinion PCT/US02/10866, dated Apr. 5, 2001.
Written Opinion PCUUS02/14261, dated May 1, 2001.
Written Opinion PCT/US03/12073, dated Apr. 18, 2002.
International Preliminary Report on Patentability PCT/Us2004/023728, dated Jul. 25, 2003.

* cited by examiner

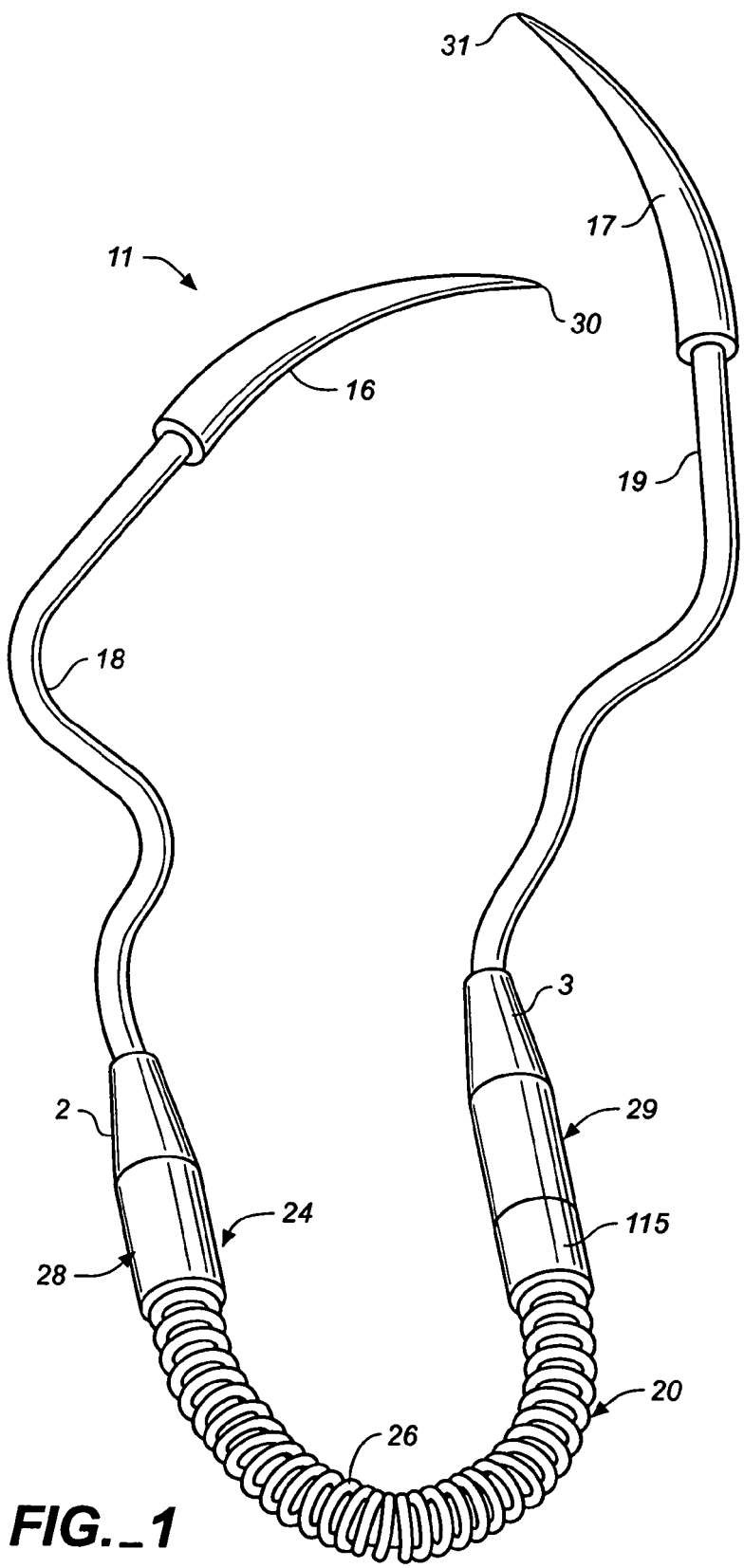
FIG._1
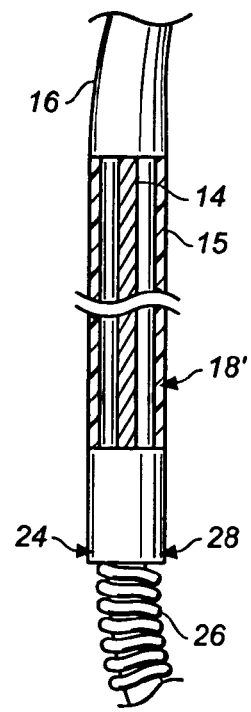
FIG._2A
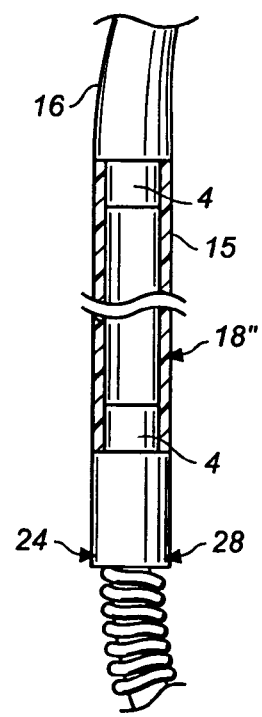
FIG._2B

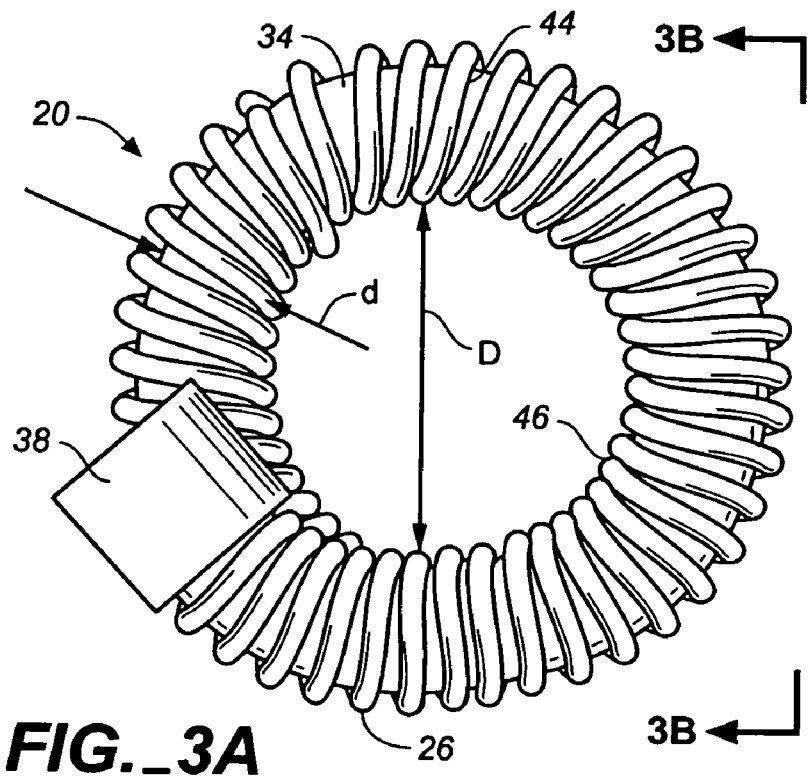
FIG._3A
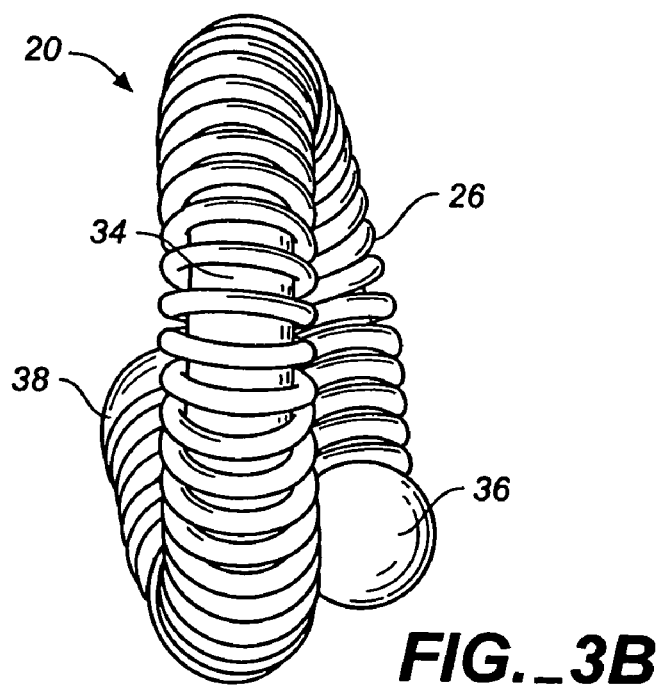
FIG._3B

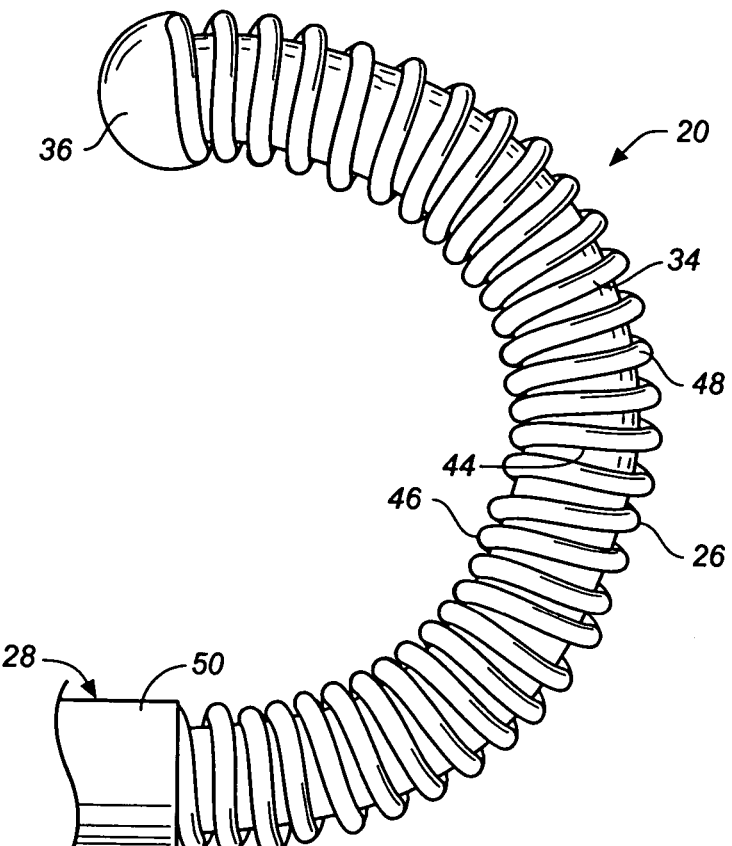
FIG._3C
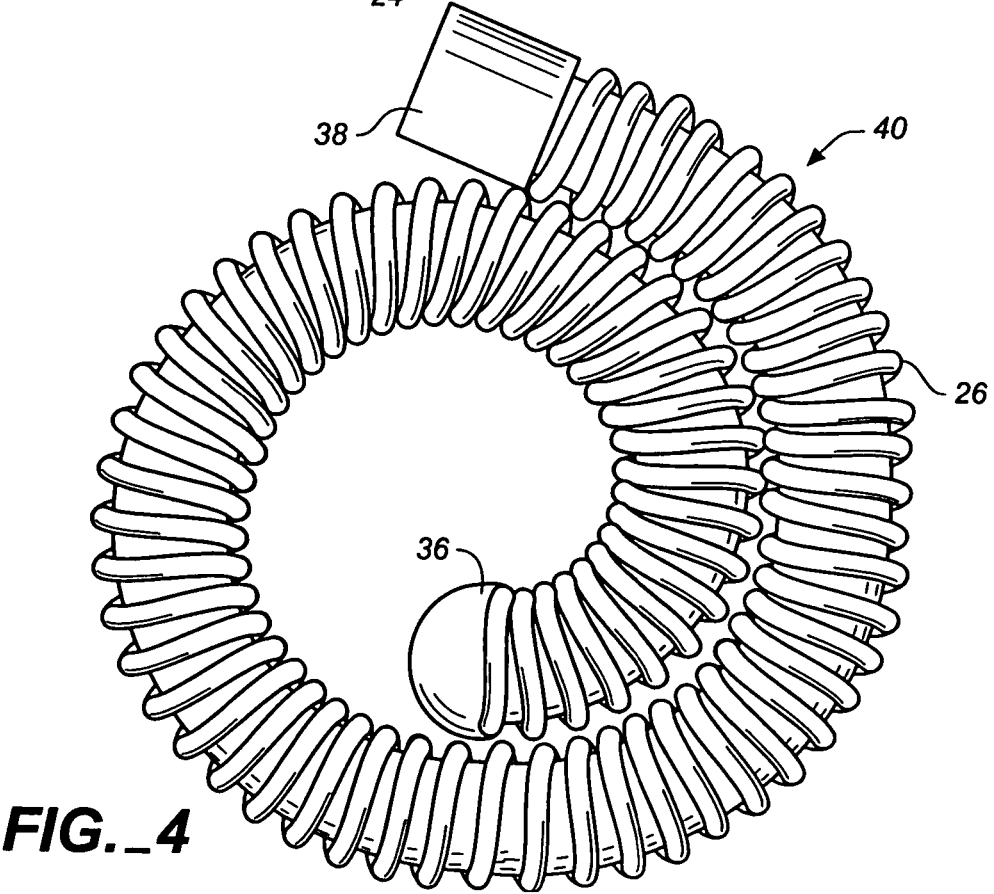
FIG._4

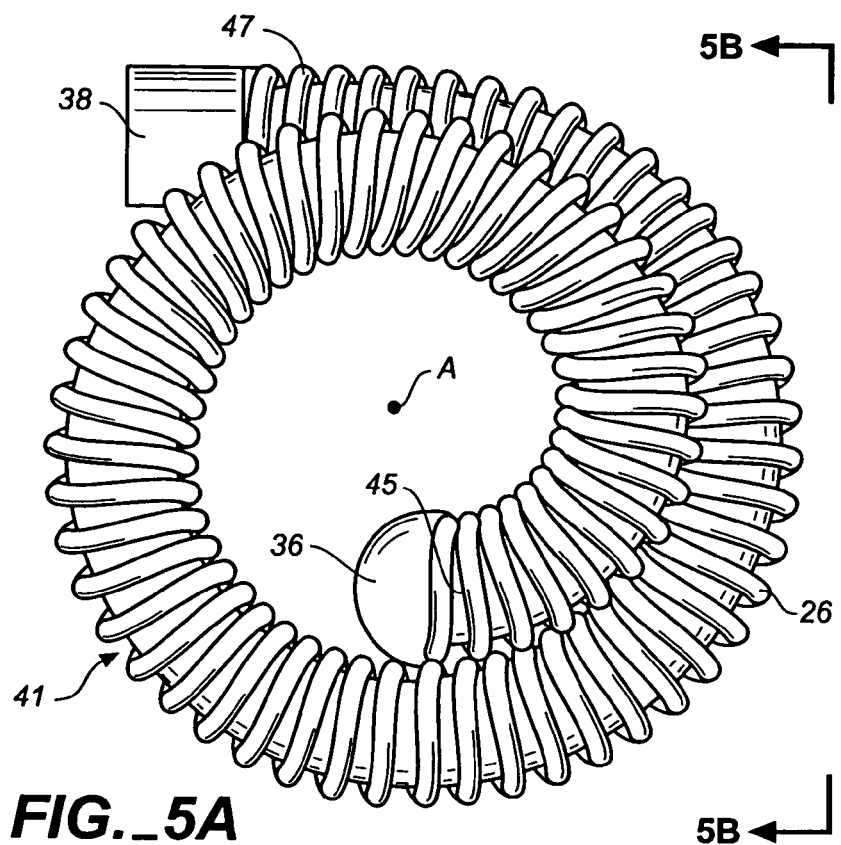
FIG._5A
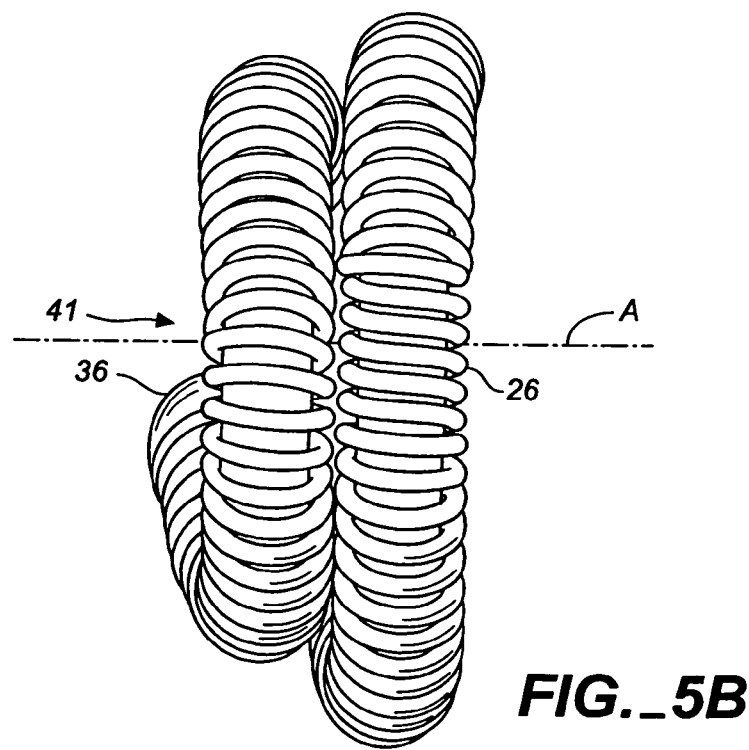
FIG._5B

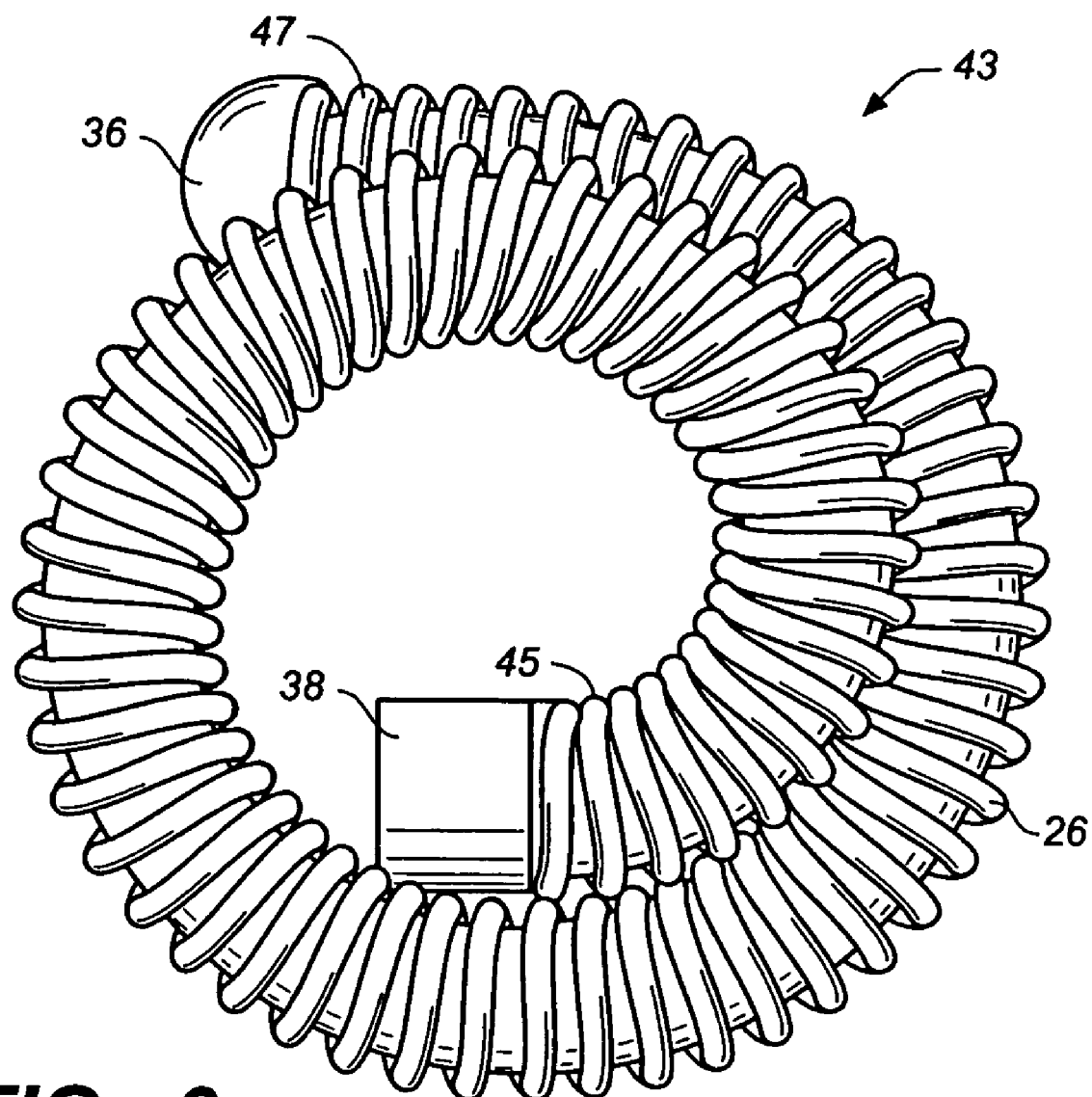
FIG._6

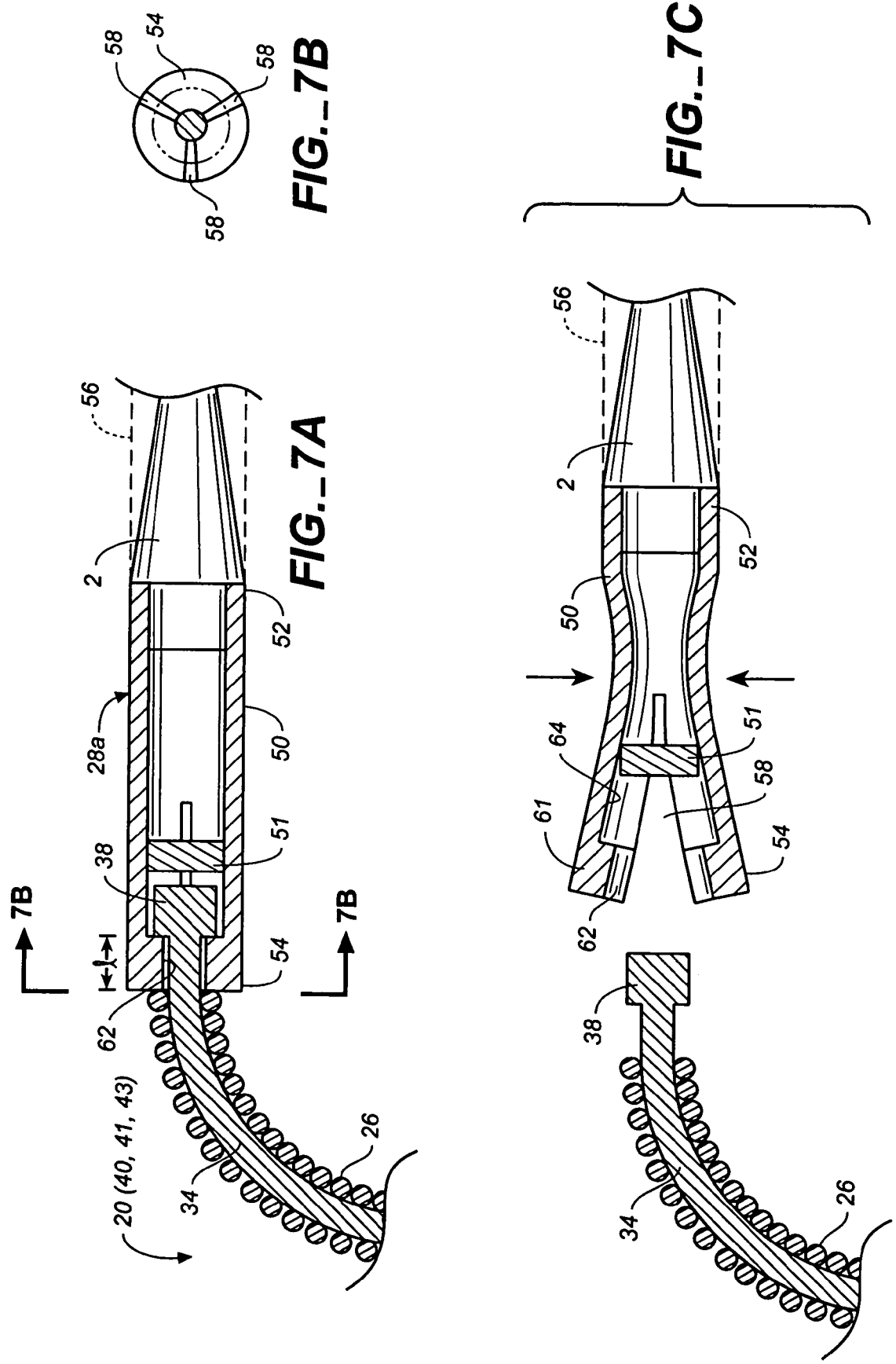

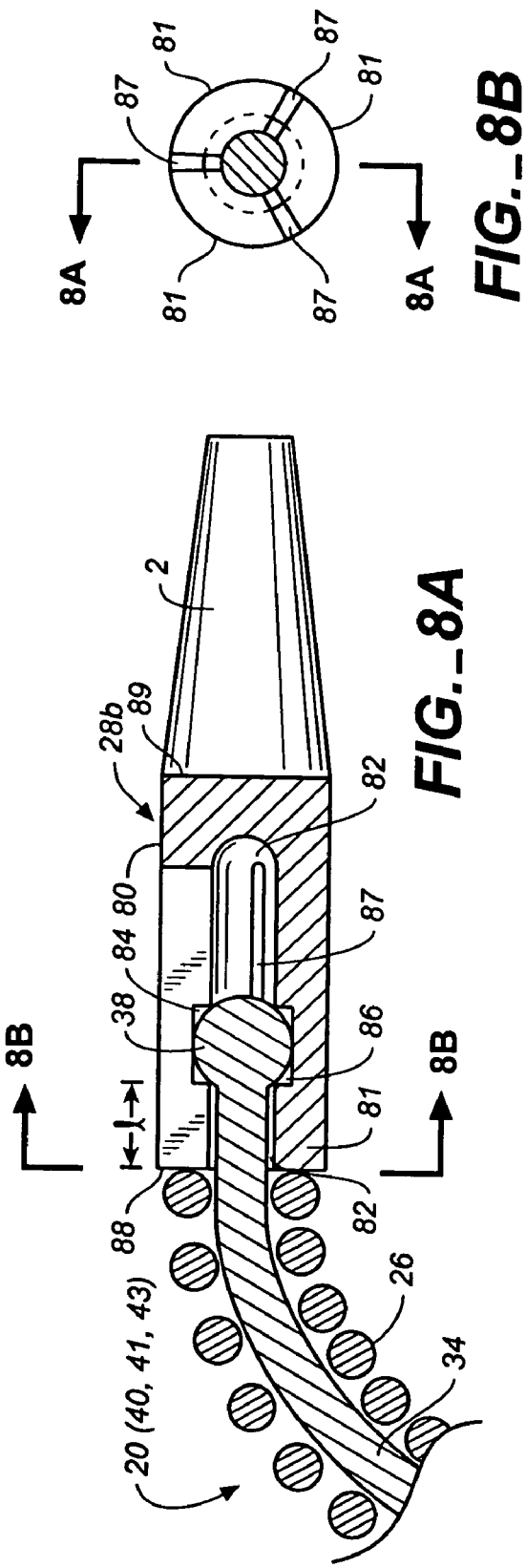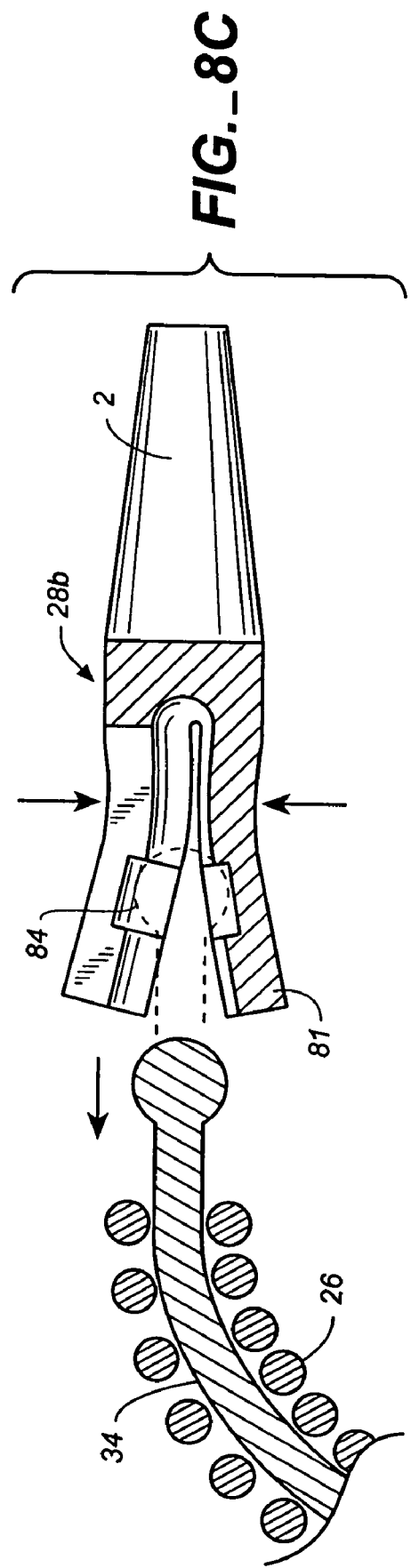

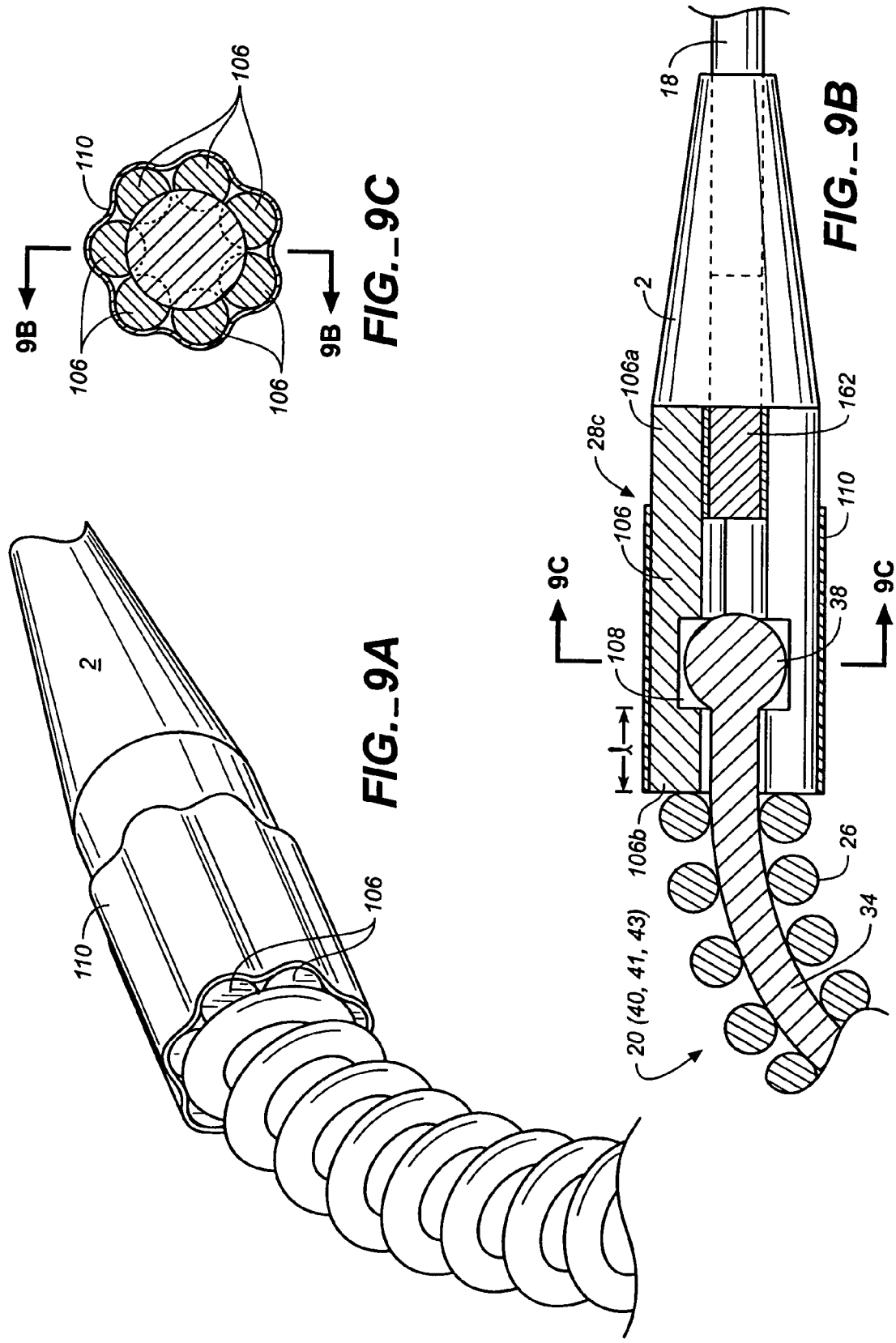

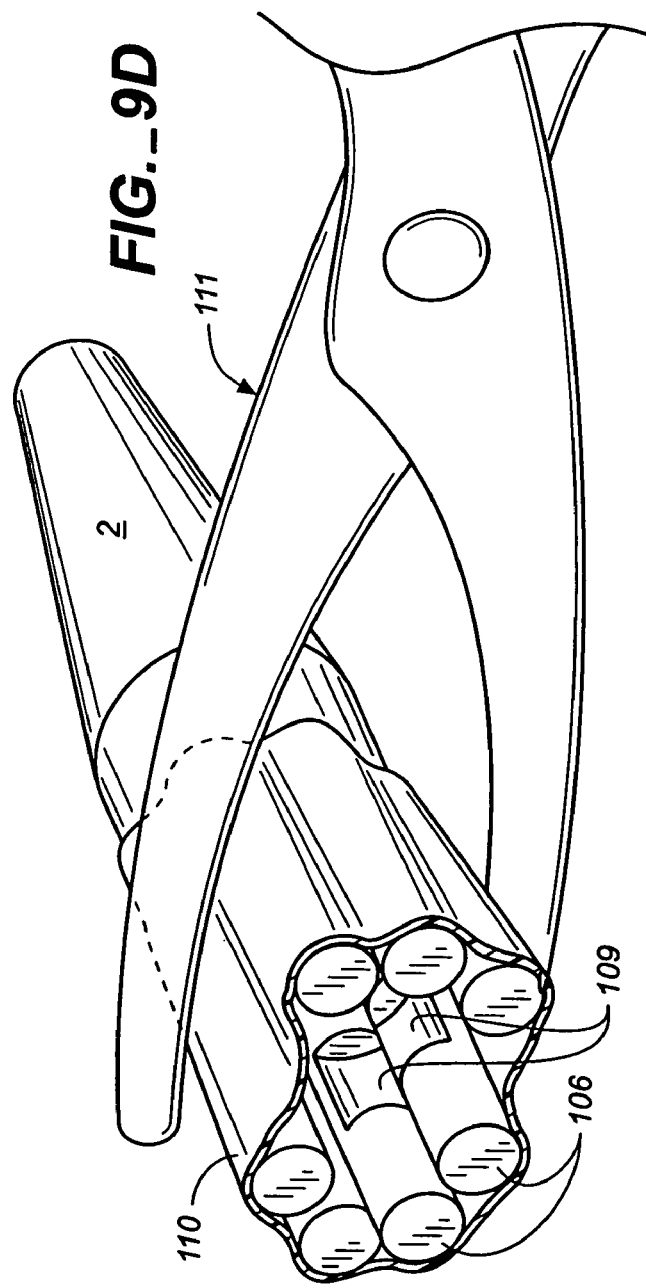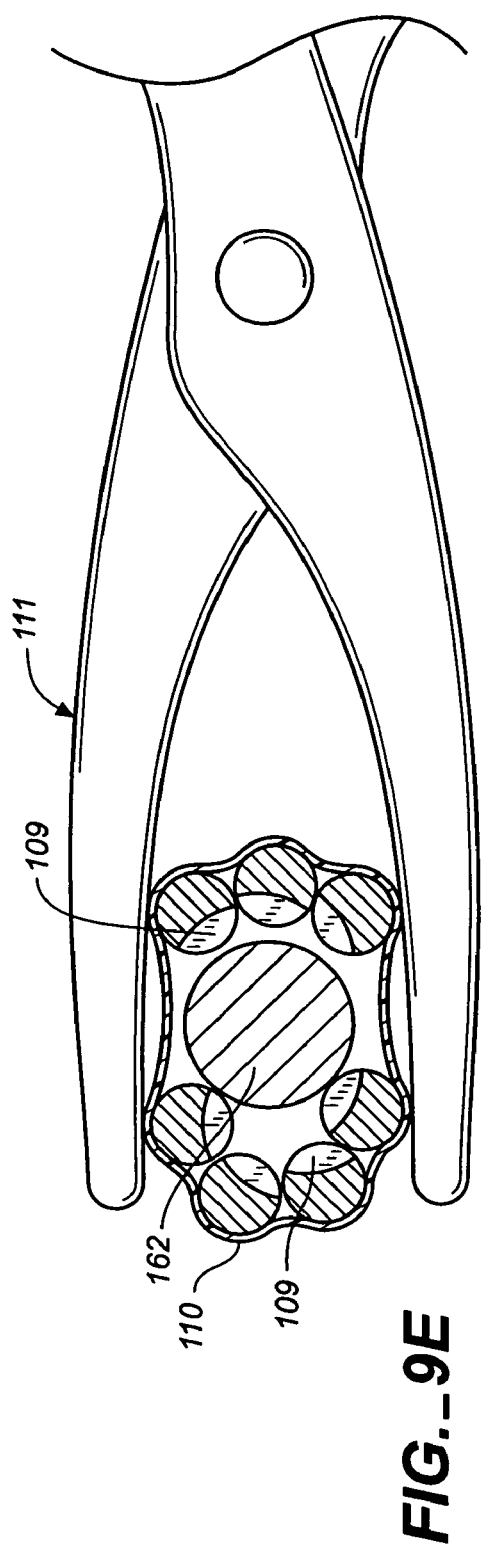

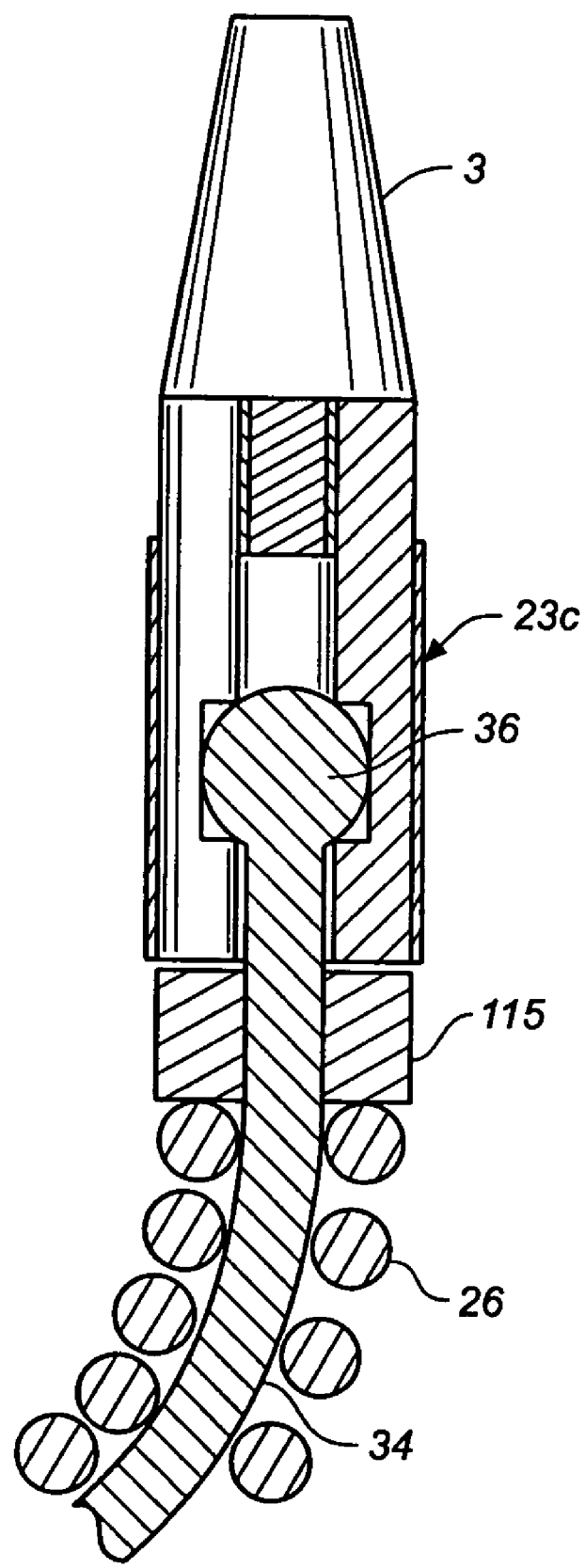
FIG._9F

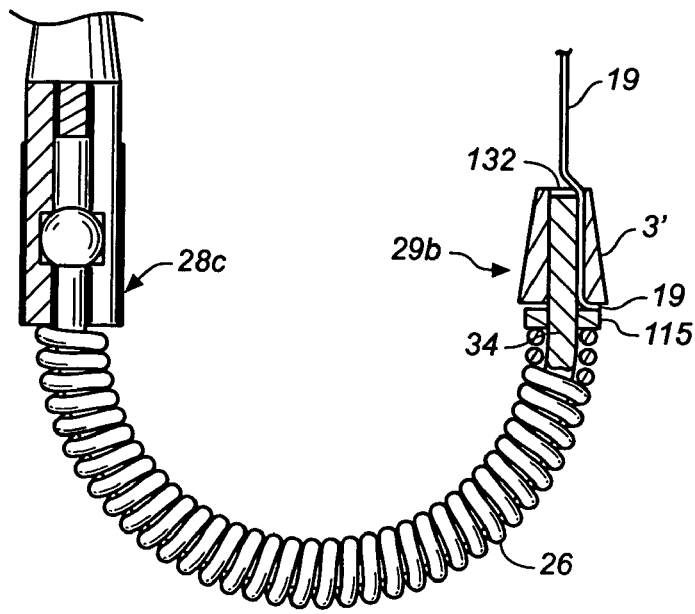
FIG._10D
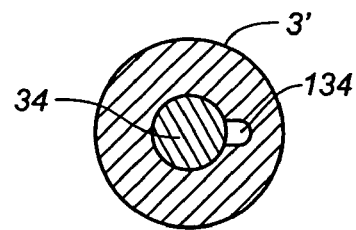
FIG._10F
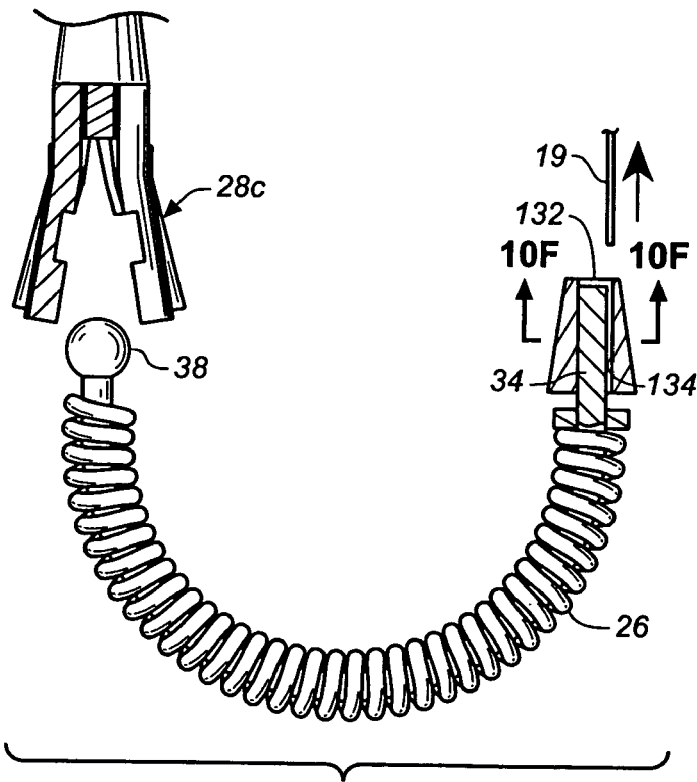
FIG._10E

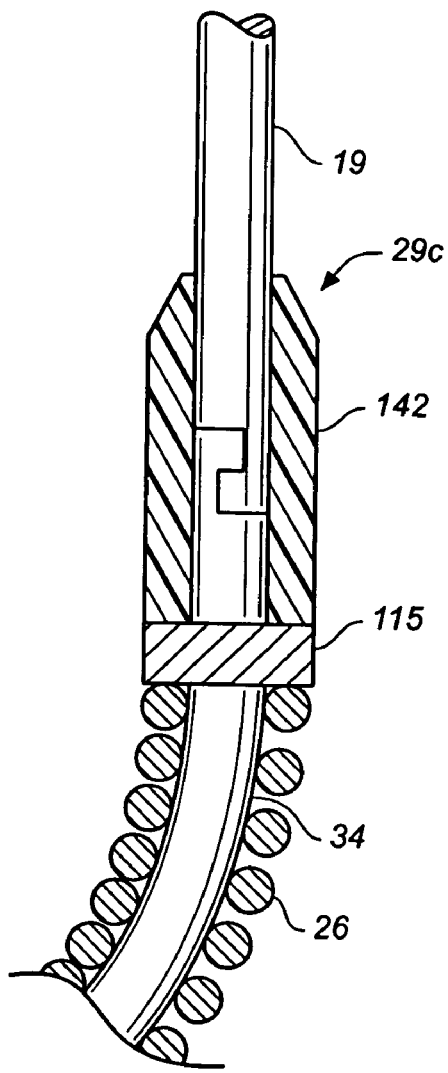
FIG._11A
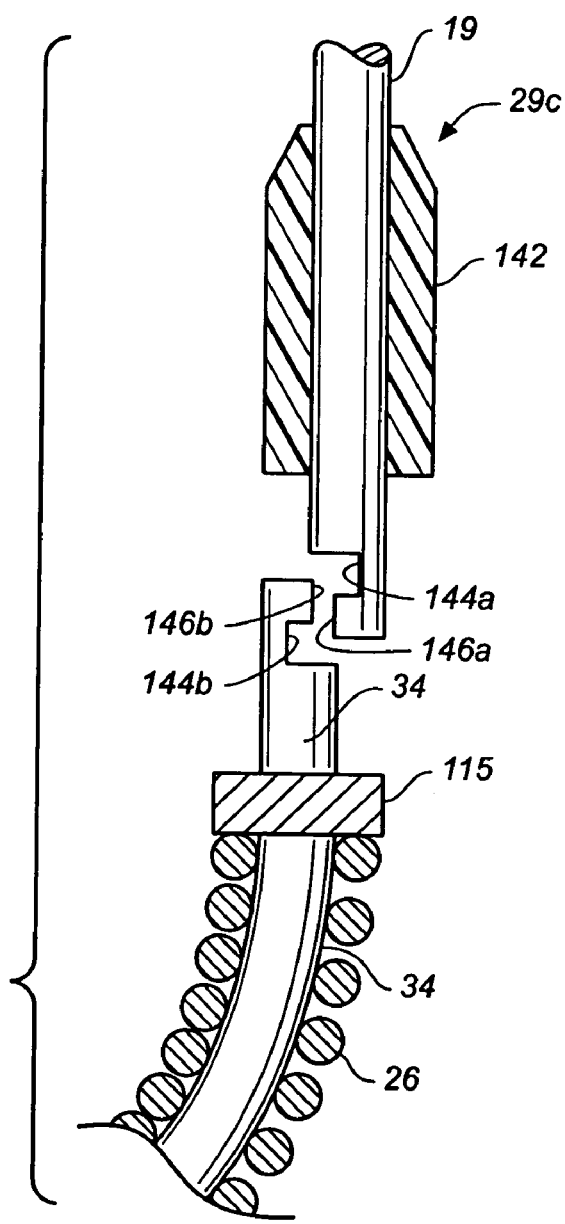
FIG._11B

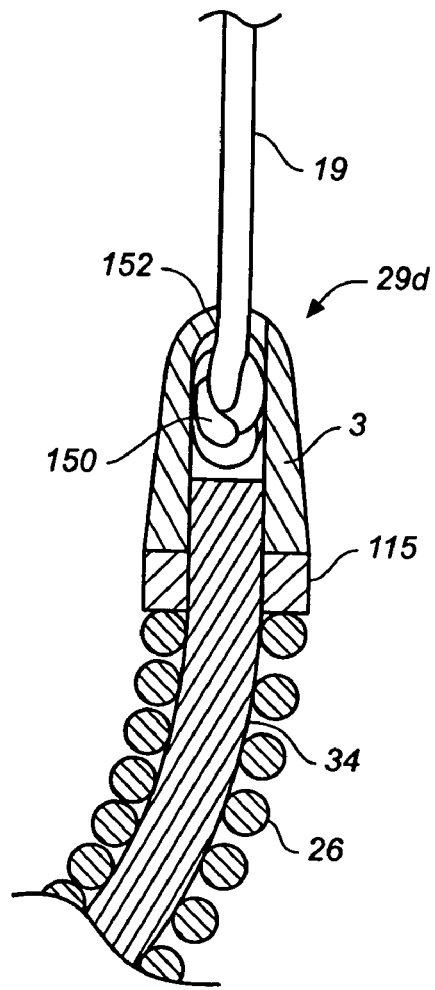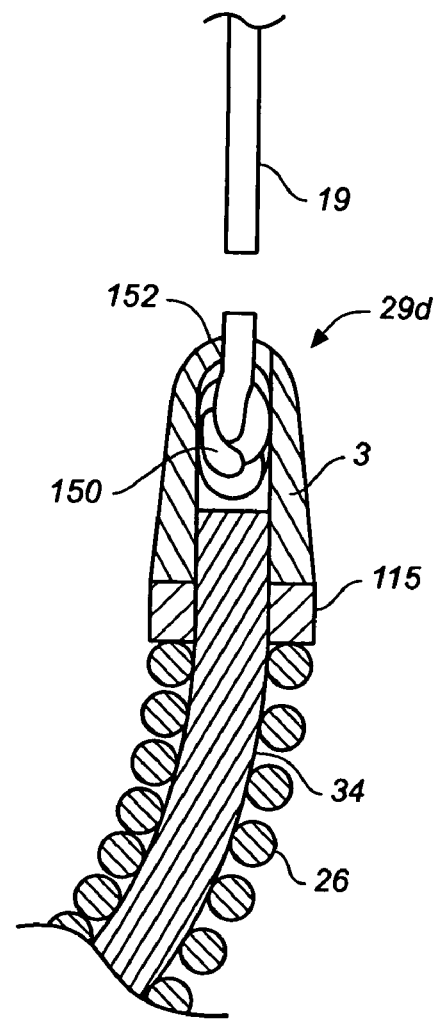
FIG._12A    FIG._12B

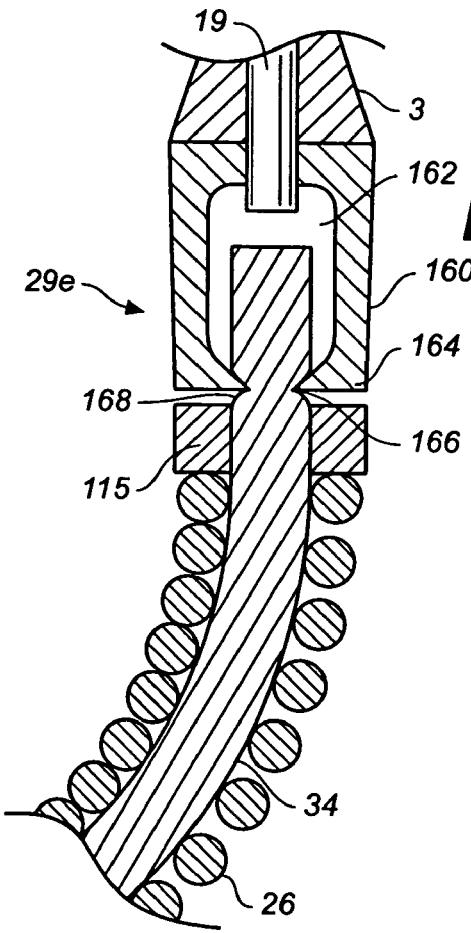
FIG._13A
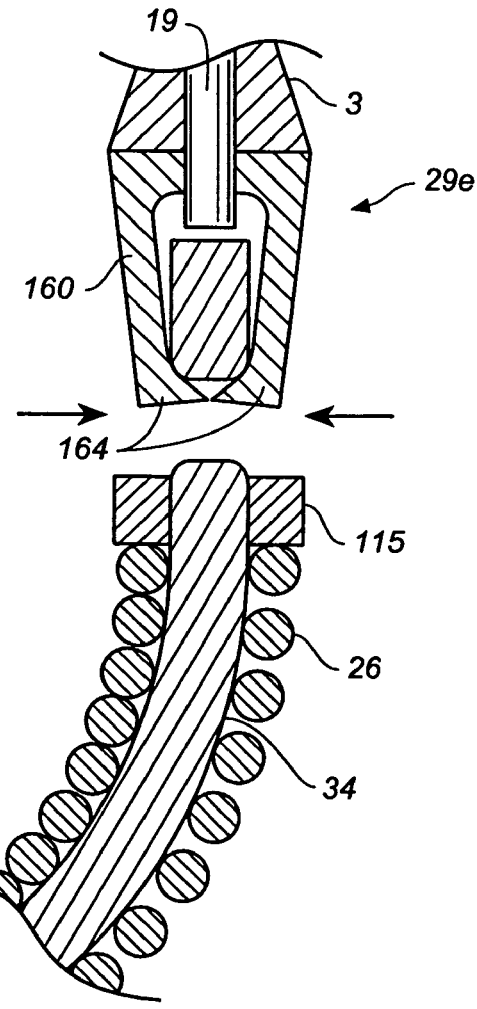
FIG._13B

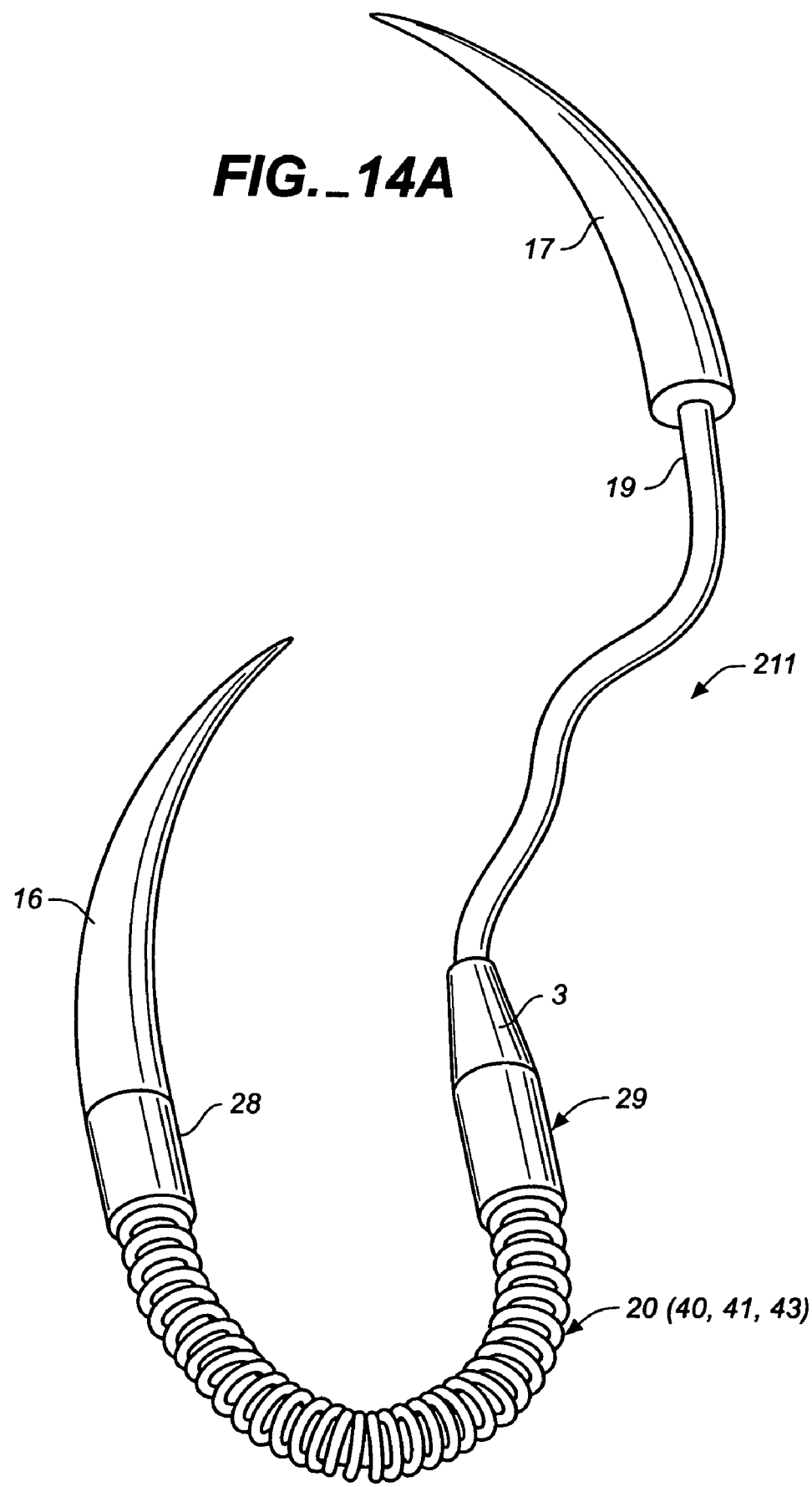
FIG._14A

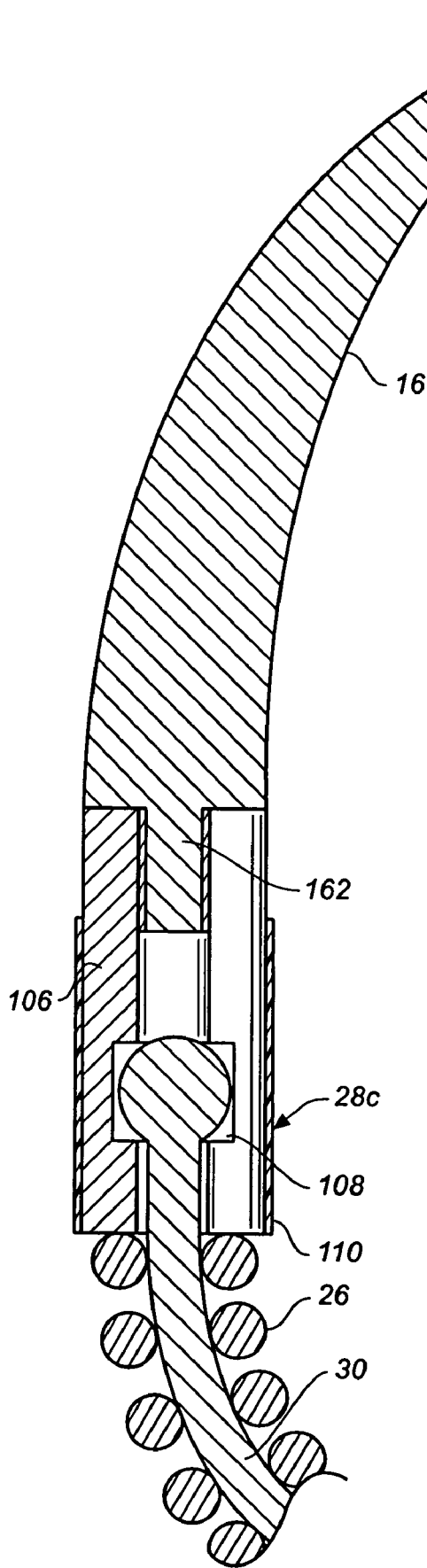
FIG._14B
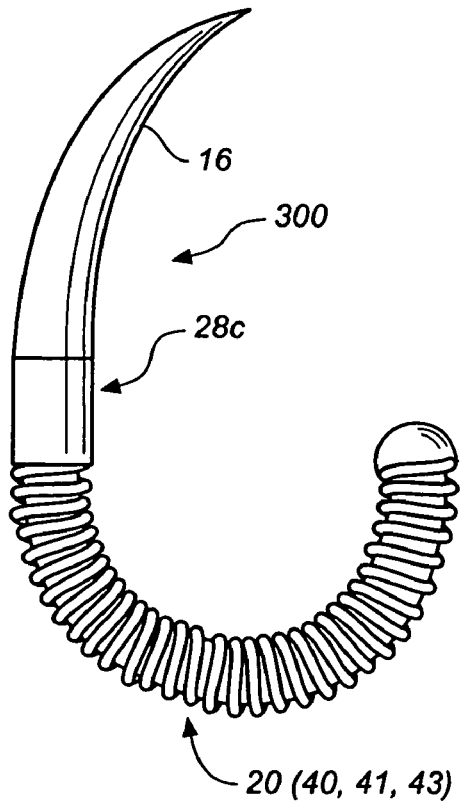
FIG._15

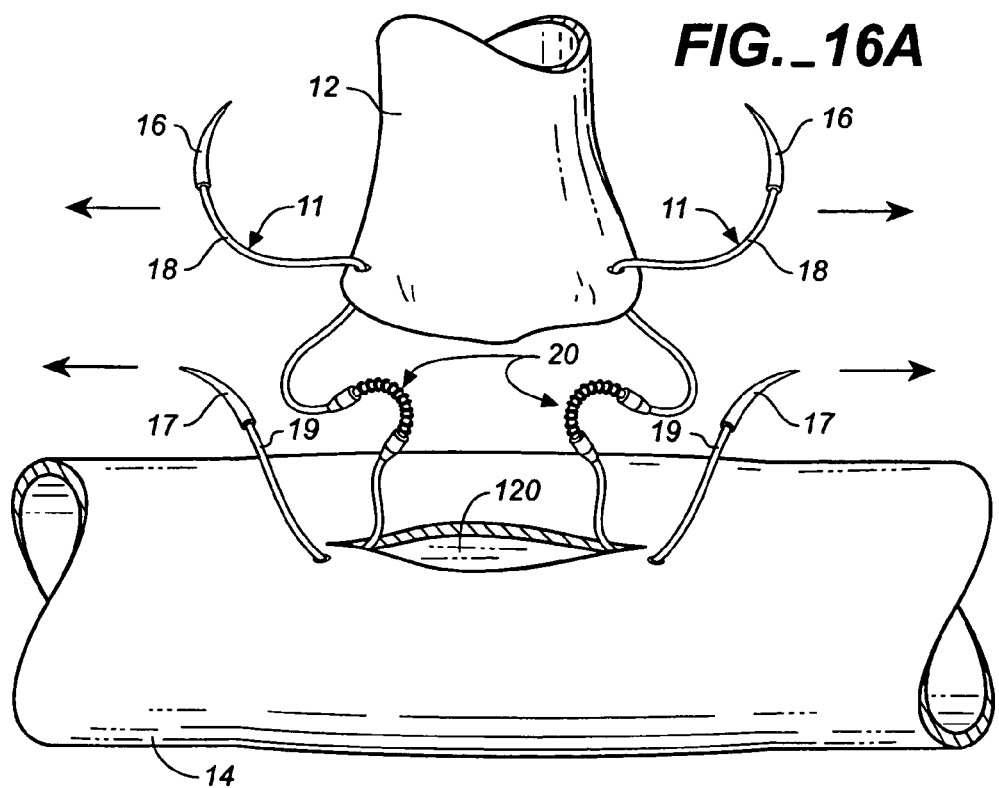
FIG._16A
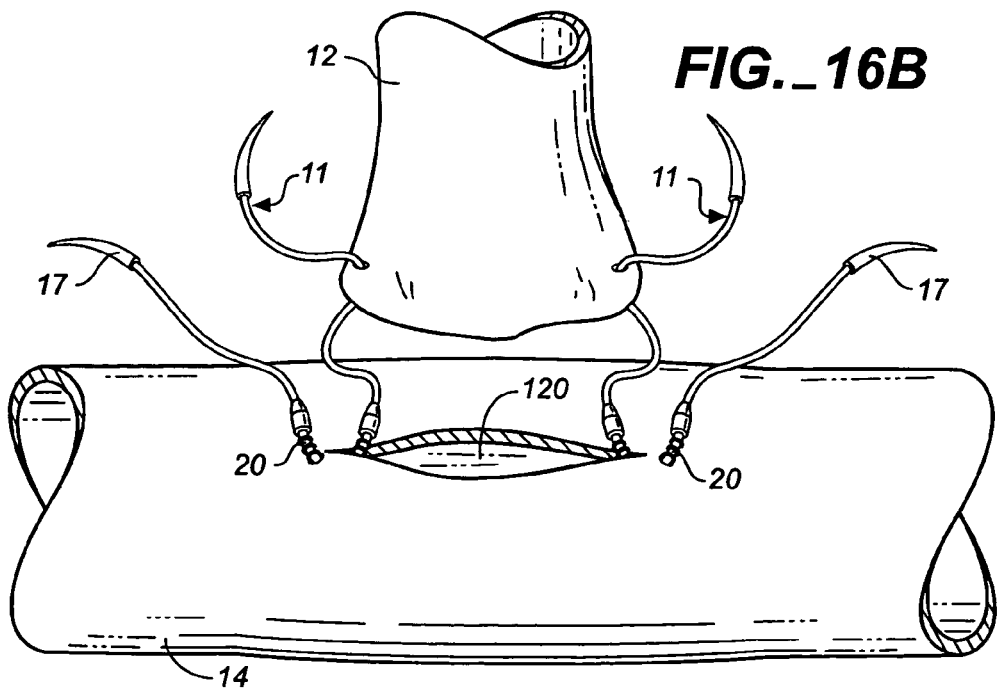
FIG._16B

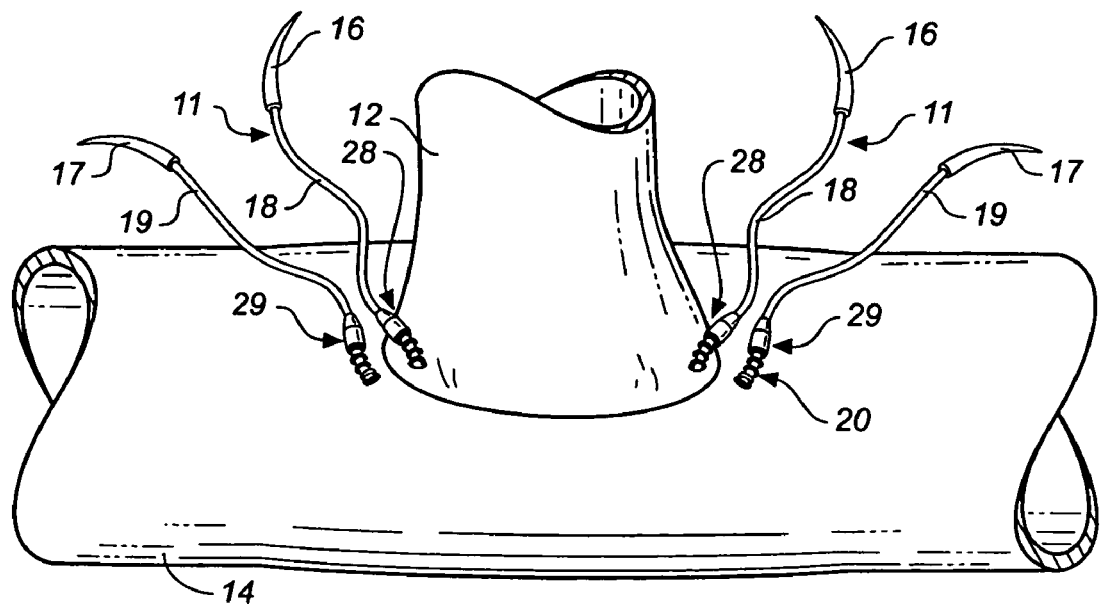
FIG._16C
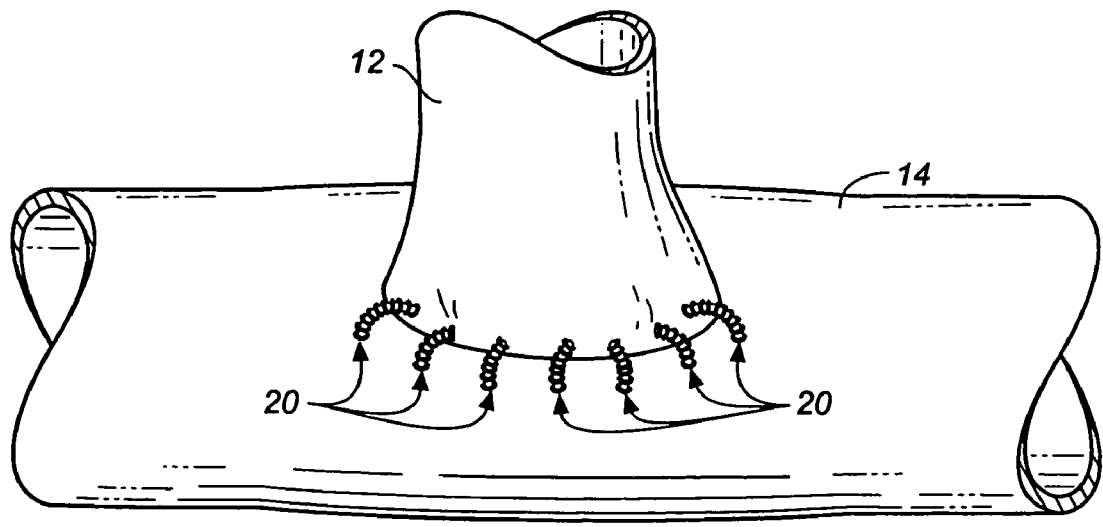
FIG._16D

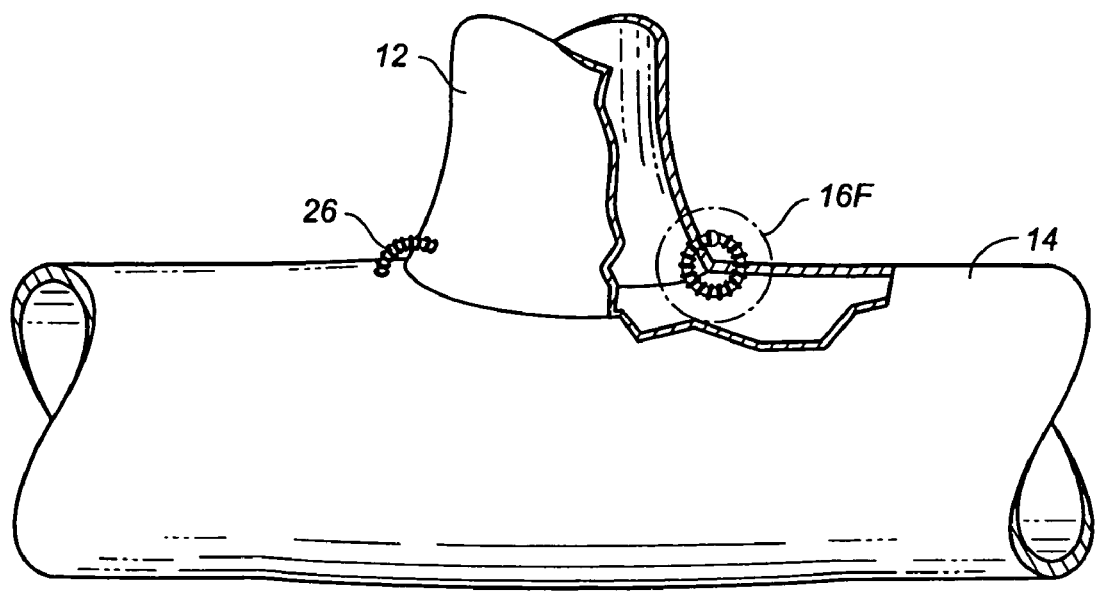
FIG._16E
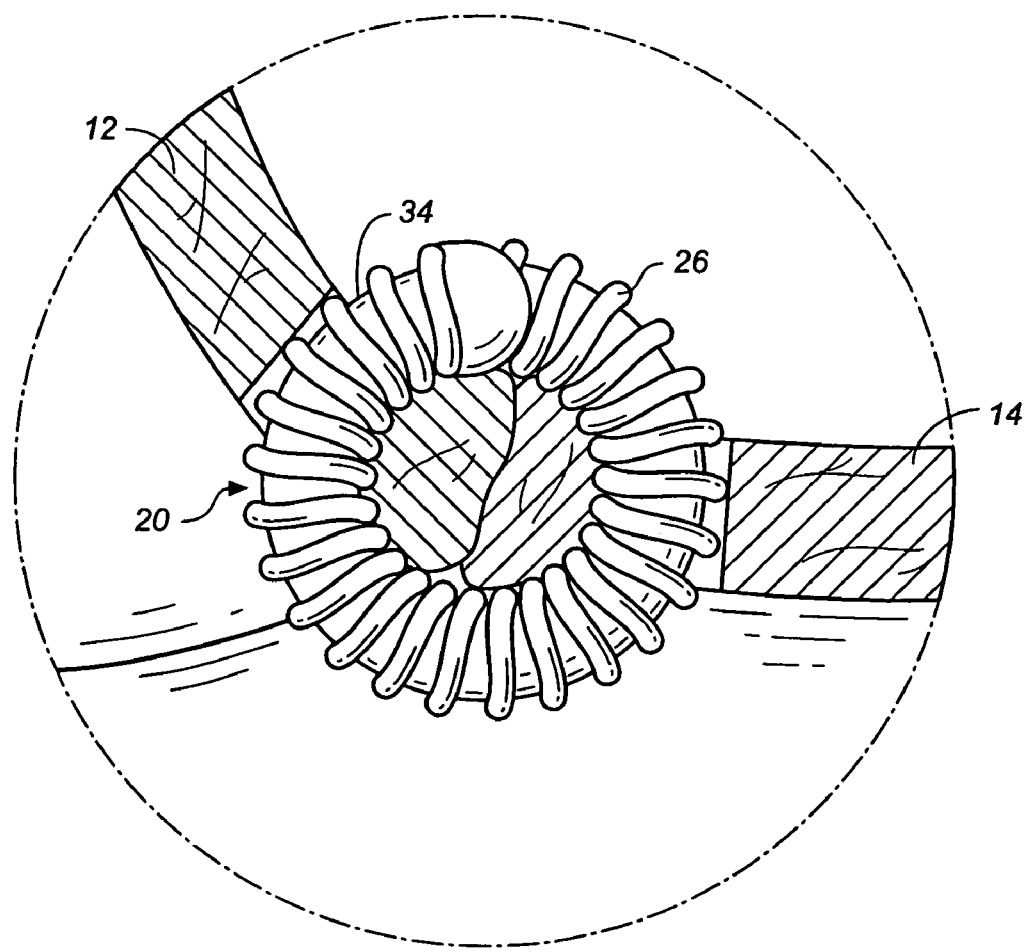
FIG._16F

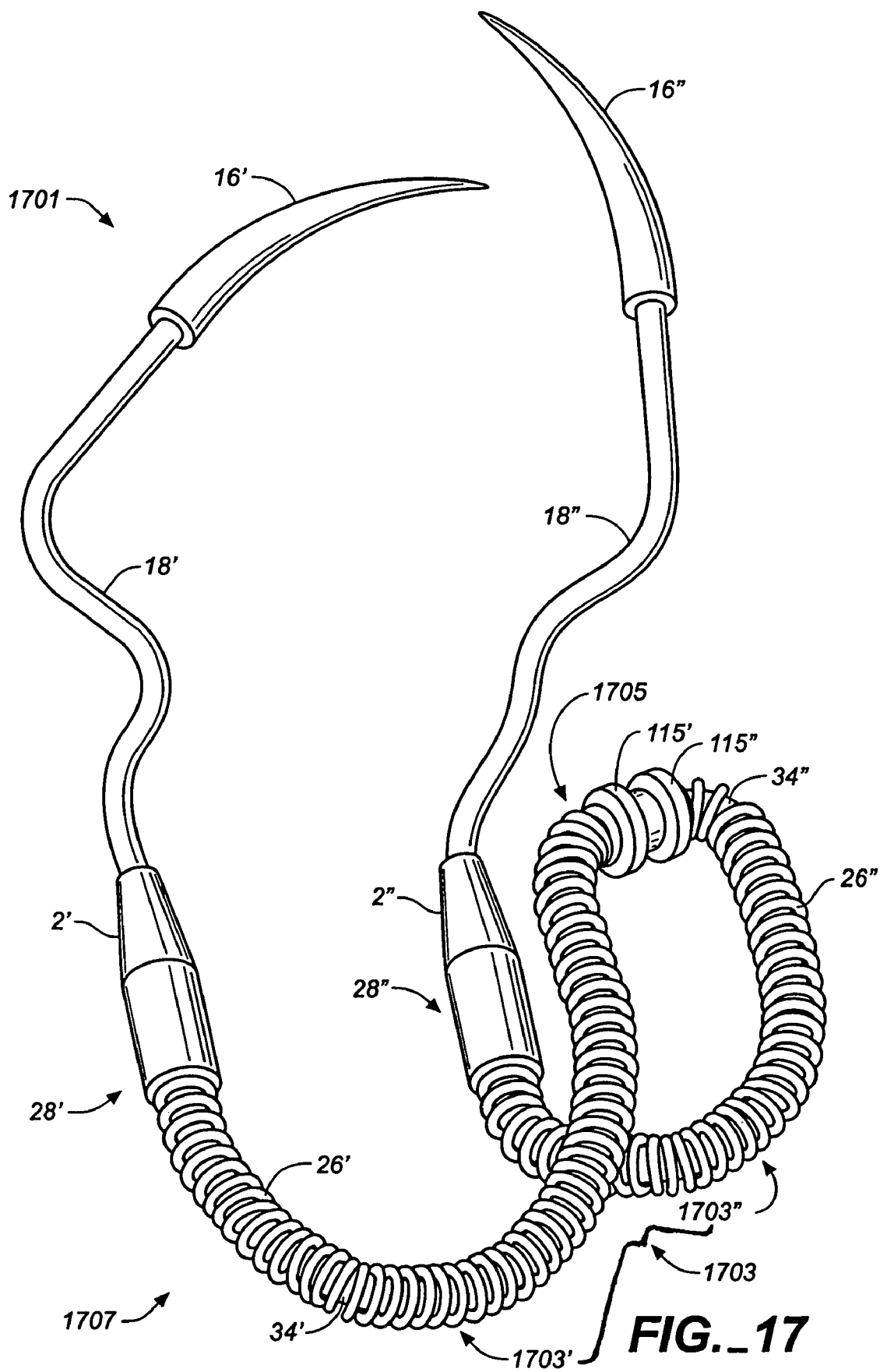
FIG._17

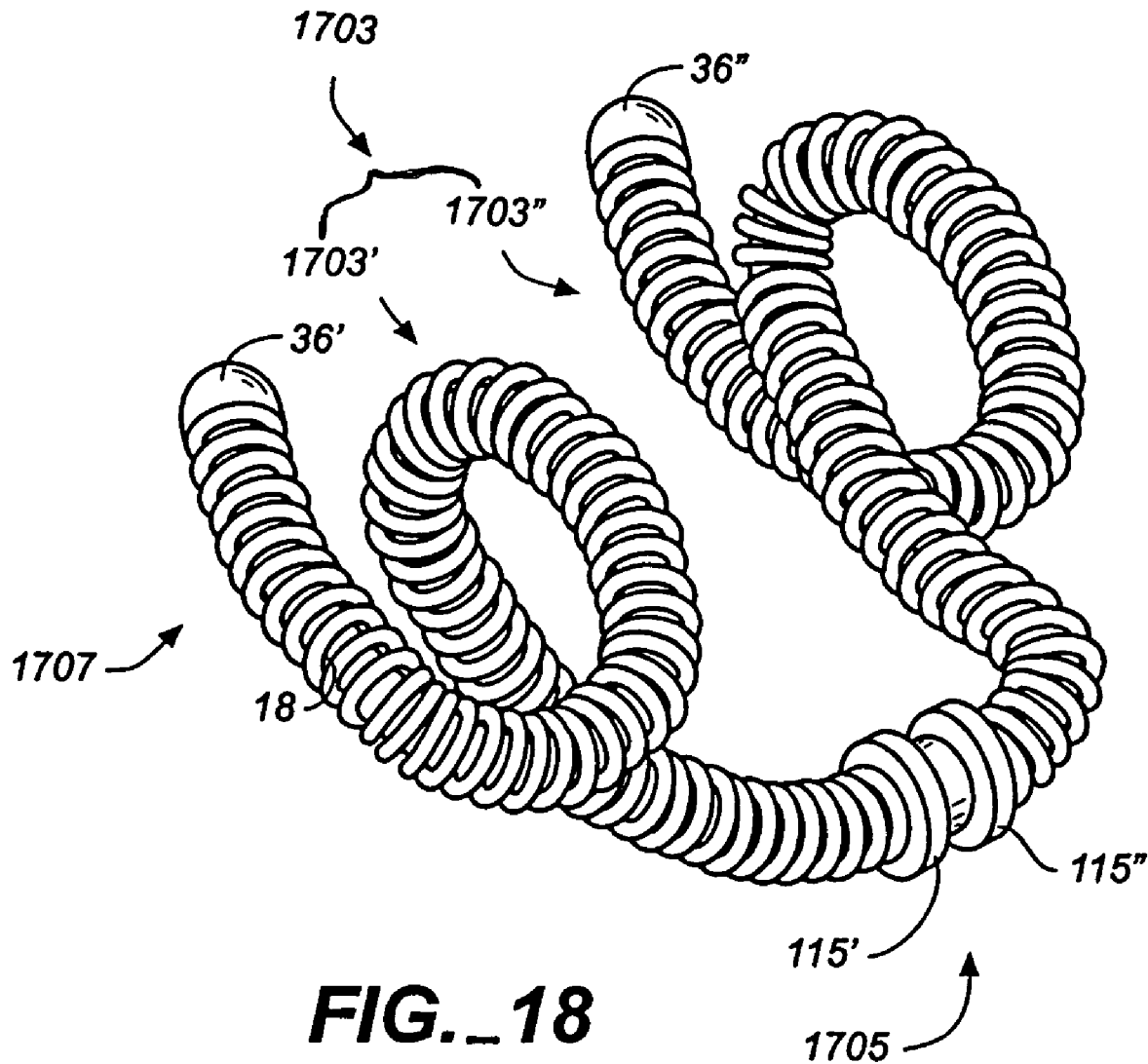
FIG._18

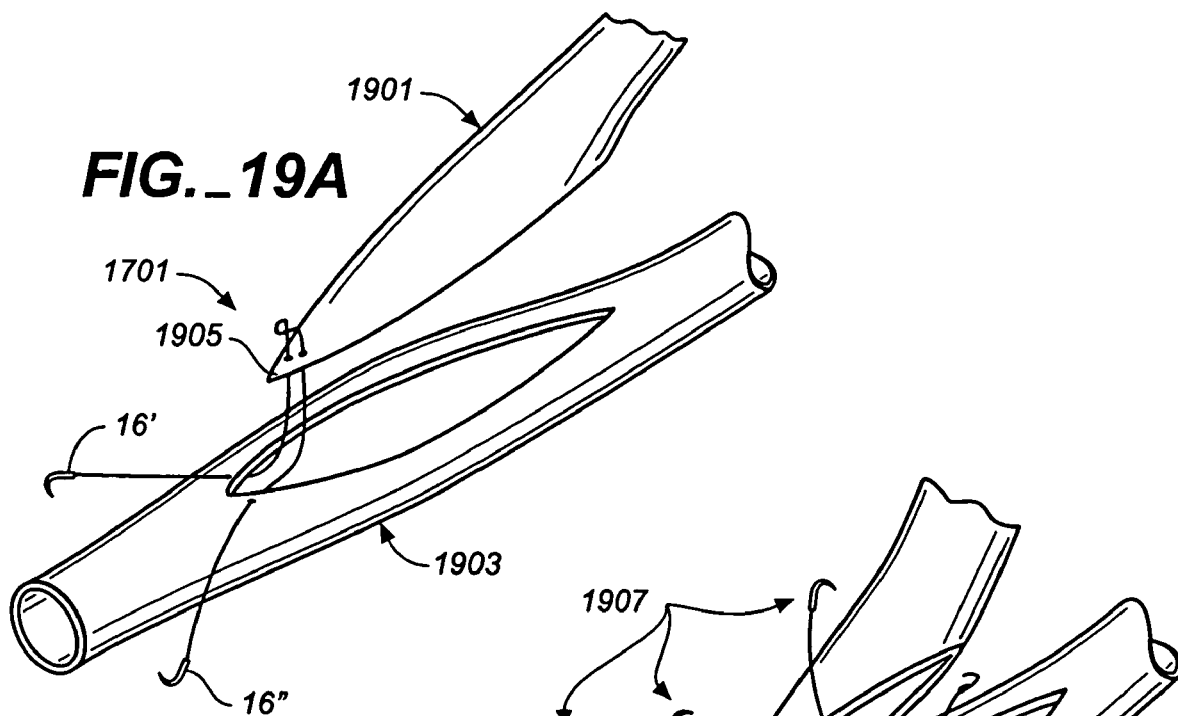
FIG._19A
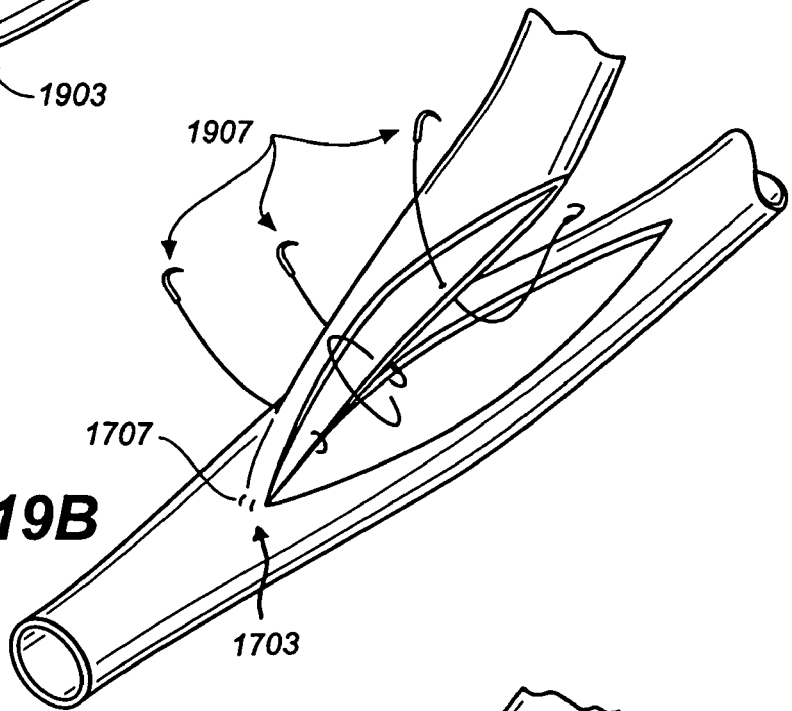
FIG._19B
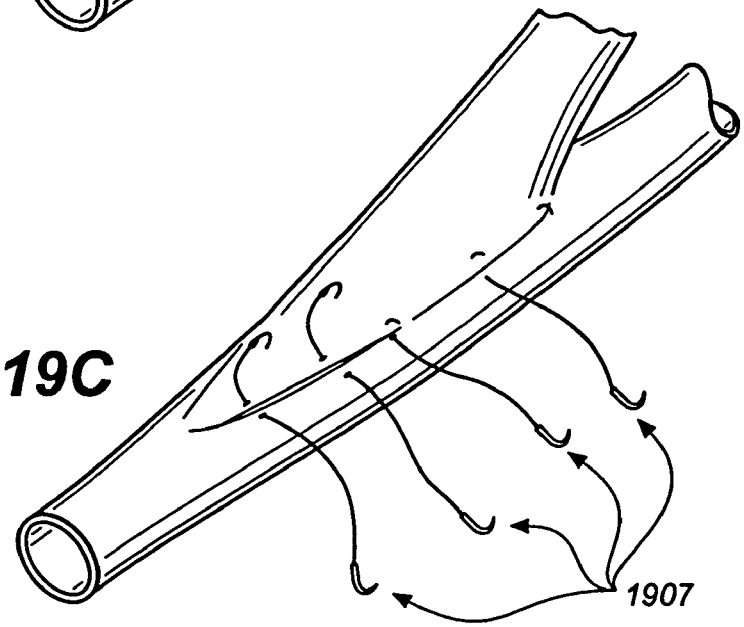
FIG._19C

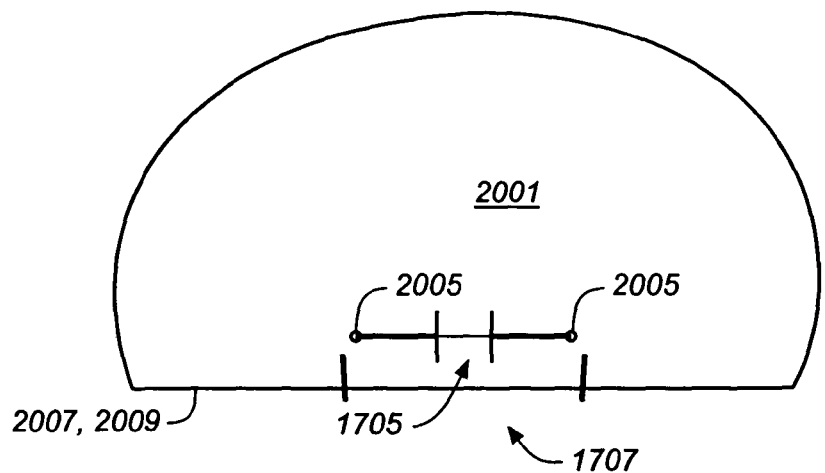
FIG._20A
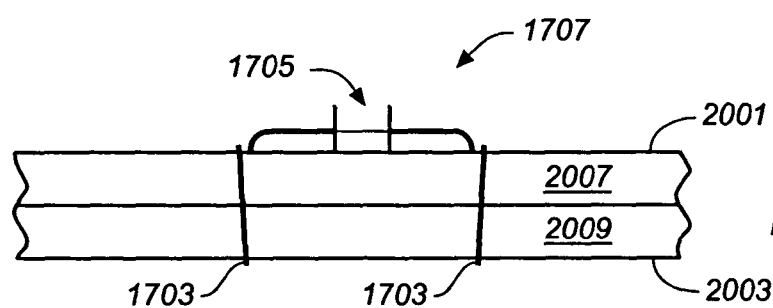
FIG._20B

BRIDGE CLIP TISSUE CONNECTOR APPARATUS AND METHODS

CROSS-REFERENCE TO RELATED DOCUMENTS

The present application is a continuation-in-part of copending patent application Ser. No. 09/260,623, filed Mar. 1, 1999 now U.S. Pat. No. 6,613,059.

FIELD OF THE INVENTION

The present invention relates to instruments and methods for connecting body tissues, tissue and prostheses, tissue and graft or any combination thereof.

BACKGROUND OF THE INVENTION

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trocar, which is a pointed, piercing device, is delivered into the body with a cannula. After the trocar pierces the abdominal or thoracic wall, it is removed and the cannula is left with one end in the body cavity, where the operation is to take place, and the other end opening to the outside. A cannula has a small inside diameter, typically 5-10 millimeters, and sometimes up to as much as 20 millimeters. A number of such cannulas are inserted for any given operation.

A viewing instrument, typically including a miniature video camera or optical telescope, is inserted through one of these cannulas and a variety of surgical instruments and refractors are inserted through others. The image provided by the viewing device may be displayed on a video screen or television monitor, affording the surgeon enhanced visual control over the instruments. Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retroperitoneal space is particularly useful for operations on the aorta and spine, or abdominal wall hernia.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded or injured artery. Arterial replacement or bypass grafting has been performed for many years using open surgical techniques and a variety of prosthetic grafts. These grafts are manufactured as fabrics (often from DACRON® (polyester fibers) or TEFLON® (fluorocarbon fibers)) or are prepared as autografts (from the patient's own tissues) or heterografts (from the tissues of animals) or a combination of tissues, semi-synthetic tissues and or alloplastic materials. A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Many factors contribute to the difficulty of performing arterial replacement or bypass grafting. See generally, Wylie, Edwin J. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as thirty minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures is also required to achieve an anastomosis with long-term patency.

Highly trained and experienced surgeons are able to perform arterial replacement and bypass grafting in open surgery using conventional sutures and suturing techniques. A suture has a suture needle that is attached or "swaged on" to a long, trailing suture material. The needle must be precisely controlled and accurately placed through both the graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

A parachuting technique may be used to align the graft with the artery in an end-to-side anastomosis procedure. One or multiple sutures are attached to the graft and artery and are used to pull or "parachute" the graft vessel into alignment with an opening formed in a sidewall of the artery. A drawback to this procedure is the difficulty in preventing the suture from tangling and the time and surgical skill required to tie individual knots when using multiple sutures. Due to space requirements, this procedure is generally limited to open surgery techniques.

The difficulty of suturing a graft to an artery using minimally invasive surgical techniques has effectively prevented the safe use of this technology in both peripheral vascular and cardiovascular surgical procedures. When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for widespread surgical use which would allow such procedures to be performed safely within the prescribed time limits.

As explained above, anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation. A clip is applied by applying an instrument about the tissue in a non-penetrating manner, i.e., the clip does not penetrate through the tissues, but rather is clamped down around the tissues. As previously explained, it is imperative in forming an anastomosis that tissues to be joined are properly aligned with respect to each other. The disclosed VCS clip applier has no means for positioning tissues. Before the clip can be applied, the tissues must first be properly positioned with respect to each other, for example by skewering the tissues with a needle as discussed above in common suturing techniques or with forceps to bring the tissues together. It is extremely difficult to perform such positioning techniques in minimally invasive procedures.

Therefore, there is currently a need for other tissue connecting systems.

SUMMARY OF THE INVENTION

The present invention involves apparatus and methods for connecting material, at least one of which is tissue. The invention may, for example, be used to secure one vessel to another, such as in a vascular anastomosis.

According to one aspect of the invention, a tissue connector assembly is provided comprising a surgical fastener, such as a surgical clip, a first tissue-piercing member and a second tissue-piercing member. The fastener may be adapted to assume a loop configuration. The fastener has a first end portion and a second end portion. The first tissue-piercing member is coupled to the first end portion and the second tissue-piercing member is coupled to the second end portion. The multiple piercing member construction facilitates threading ends of the assembly from inner to outer walls of material, such as tissue, which may eliminate or minimize the possibility of dislodging material from the inner wall of a vessel, for example.

According to another aspect of the invention, a flexible member, such as a suture, may be provided between at least one piercing member and the fastener to facilitate threading the fastener and/or "parachute" techniques, for example.

According to another aspect of the invention, synchronized piercing member release mechanisms may be provided. In one embodiment, the tissue connector assembly may include a first coupling, which couples the first tissue piercing member and first end portion of the surgical fastener, and a second coupling, which couples the surgical fastener second end portion and second piercing member. The first coupling releases the other coupling in response to releasing the first coupling. According to one aspect of this embodiment, multiple tissue piercing members may be decoupled from the surgical fastener with one release actuator. According to another aspect, the piercing members may be decoupled essentially simultaneously.

According to yet another aspect of the invention, a tissue connector assembly is provided for joining tissues as a "bridge clip" that includes a surgical fastener having two surgical clips connected by a bridge. In one embodiment the two clips are biased into an open configuration, and can close through a release mechanism. In an alternative embodiment, each clip has one release mechanism and one coil surrounding the clip to individually bias the clips in an open configuration. In yet another alternative embodiment, each clip has one release mechanism, and a single coil is connected to both release mechanisms to bias both clips. In a preferred embodiment, each clip is attached to a piercing member through a length of a flexible member.

According to another aspect of the present invention a tissue connector assembly is provided for attaching tissue. In one embodiment the assembly includes a surgical fastener having two self-closing clips separated by a bridge portion and a release mechanism to actuate the self-closing clips. Another embodiment provides a surgical fastener having two clips, at least one of which is self-closing, separated by a bridge portion and coupled to tissue piercing members.

According to another aspect of the invention, a bridge clip is provided to facilitate attaching tissue using a technique such as parachuting. With both clips in the open configuration and attached to their respective piercing member, each piercing member is used to pierce one side of a tissue, effectively positioning the bridge against the tissue. After a second set of piecings on a second tissue, the first tissue can be guided onto the second tissue. With the clips threaded through both tissues, the release mechanism is actuated, securing the two tissues at two slightly displaced locations. In yet another aspect of the invention, a bridge clip is provided to attach tissues using a technique similar to a horizontal mattress suture.

The above is a brief description of some deficiencies in the prior art and advantages of the present invention. Other features, advantages, and embodiments of the invention will be apparent to those skilled in the art from the following description, accompanying drawings, and claims.

BRIEF DESCRIPTION OF THE DRAWINGS

FIG. 1 is a perspective of a tissue connector assembly constructed in accordance with the principles of the present invention;

FIG. 2A is a partial sectional view illustrating an alternate construction of flexible member 18 of FIG. 1;

FIG. 2B is a partial sectional view illustrating yet another construction of flexible member 18 of FIG. 1;

FIGS. 3A, 3B and 3C show a fastener which can be used with the tissue connector assembly of FIG. 1, where FIG. 3A is a top view of the fastener in a closed position, FIG. 3B is a side view of the fastener of FIG. 3A, and FIG. 3C is an enlarged view of the fastener of FIG. 3A in an open position;

FIG. 4 is a top view of another fastener configuration, which can be used with the tissue connector assembly of FIG. 1;

FIGS. 5A and 5B show yet another fastener configuration which can be used with the tissue connector assembly of FIG. 1, where FIG. 5A shows the fastener in a closed position and FIG. 5B is a side view of the fastener of FIG. 5A;

FIG. 6 is top view of yet a further configuration of a fastener that can be used with the tissue connector assembly of FIG. 1 with the fastener in a closed position;

FIGS. 7A, 7B and 7C illustrate a release mechanism which can be used with any of the fasteners described above and the tissue connector assembly of FIG. 1, where FIG. 7A shows the restraining device in cross-section and in a locked position, FIG. 7B is a transverse cross-sectional view of the restraining device taken in a plane along line 7B-7B of FIG. 7A, and FIG. 7C is a cross-sectional view of the restraining device of FIG. 7A in an unlocked position;

FIGS. 8A, 8B and 8C illustrate another release mechanism which can be used with any of the fasteners described above and the tissue connector assembly of FIG. 1, where FIG. 8A shows the restraining device in cross-section and in a locked position, FIG. 8B is a transverse cross-sectional view of the restraining device taken in a plane along line 8B-8B of FIG. 8A, and FIG. 8C is a cross-sectional view of the restraining device of FIG. 8A in an unlocked position;

FIGS. 9A-9F illustrates yet another release mechanism which can be used with any of the fasteners described above, where FIG. 9A shows a perspective view of the retaining device coupled with a fastener, FIG. 9B is a sectional view of the retaining device of FIG. 9A, FIG. 9C is a transverse cross-sectional view of the restraining device taken along line 9C-9C in FIG. 9B, FIGS. 9D and 9E are perspective and end views of the restraining device, respectively, showing the device depressed for release of the fastener; and FIG. 9F shows the retaining device of FIG. 9A with an adapter for coupling to the other end of the fastener;

FIGS. 10A and 10C are partial sectional views of the system in a coupled and decoupled state, respectfully, and FIG. 10B is a sectional view taken along lines 10B-10B in FIG. 10A;

FIGS. 10D-10F show another synchronized fastener release system where FIGS. 10D and 10E are partial sectional views of the system in a coupled and decoupled state, respectfully, and FIG. 10F is a transverse cross-sectional view taken along line 10E-10F in FIG. 10E;

FIGS. 11A and 11B are partial sectional views of another piercing member and/or suture release mechanism in a coupled and decoupled state, respectfully;

FIGS. 12A and 12B are partial sectional views of a further piercing member and/or suture release mechanism in a coupled and decoupled state, respectfully;

FIGS. 13A and 13B are partial sectional views of yet another piercing member and/or suture release mechanism in a coupled and decoupled state, respectfully;

FIG. 14A is a front view of a another embodiment of a tissue connector assembly of the present invention;

FIG. 14B is a sectional view of a piercing member and release mechanism combination, which can be used in the embodiment, illustrated in FIG. 14A;

FIG. 15 is a front view of a lateral tissue connector, which can be used in conjunction with any of the assemblies described above;

FIGS. 16A-16D diagrammatically illustrate a method of aligning and connecting graft and target vessels with the tissue connector assembly of FIG. 1, where FIG. 16A shows two such tissue connector assemblies threaded through a graft and target vessel, FIG. 16B shows a further step in connecting the graft and target vessel with the tissue connector assembly fastener is positioned in the target vessel, FIG. 16C shows yet a further step where the graft has been brought into position over the opening formed in the target vessel and the tissue connector assembly fastener positioned through the walls of the graft and target vessel and FIG. 16D shows the fasteners released from the tissue connector assembly of FIG. 1 and securing the graft and target vessel together with additional laterally disposed fasteners;

FIG. 16E is a partial sectional view of the graft and target vessels with the tissue connector assembly fasteners of FIG. 1 in place prior to placement of additional lateral fasteners;

FIG. 16F is an enlarged view of the tissue connection within line 16F of FIG. 16E;

FIG. 17 is a perspective of a bridge clip tissue connector assembly of the present invention;

FIG. 18 is a perspective view of the fastener of FIG. 17, in which the fastener has been released from the tissue connector assembly and is in a closed position;

FIGS. 19A-19C diagrammatically illustrate a method of approximating graft and target vessels with the tissue connector assemblies of FIGS. 1 and 17, where FIG. 19A shows the tissue connector assembly of FIG. 17 threaded through the toe of a graft vessel and target vessel union, FIG. 19B shows a further step in connecting the graft and target vessels with the fastener of FIG. 17 connecting the toe of the graft and three connector assemblies of FIG. 1 in various states of connecting the graft and target vessels, and FIG. 19C shows yet a further step where tissue connector assemblies of FIG. 1 are shown securing the remainder of the vessel edges; and FIGS. 20A-20B are a top and side view, respectively, of a bridge clip as used as a horizontal mattress suture.

Corresponding reference characters indicate corresponding elements throughout the drawings.

DESCRIPTION OF THE INVENTION

Figure 10A:
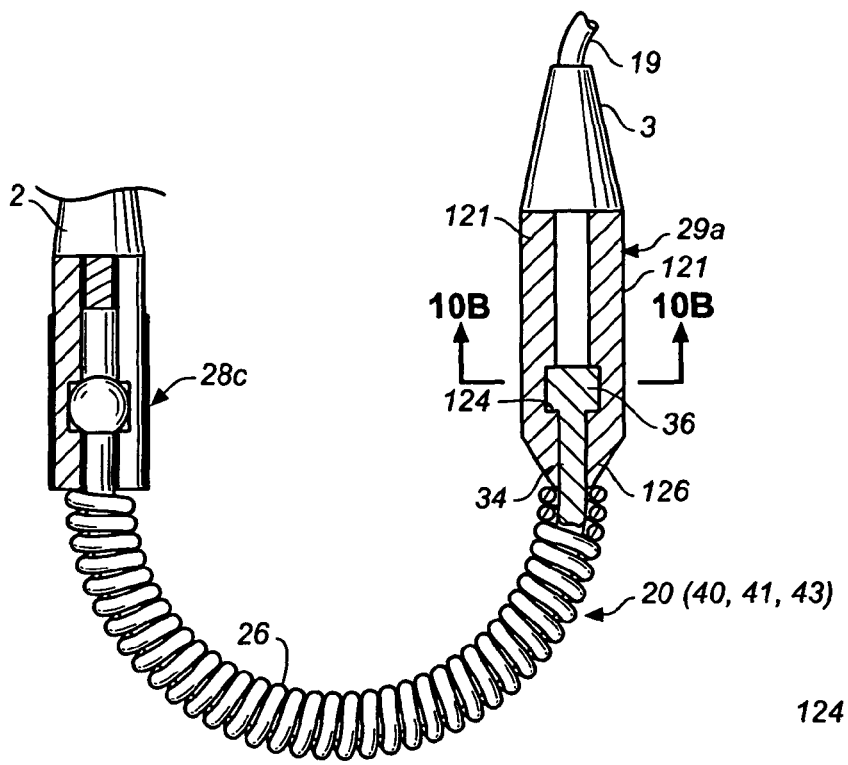
FIGS. 10A-10C show a synchronized fastener release system, where

The present invention generally involves methods and devices for manipulating, aligning and/or connecting tissues, tissue and prosthesis, tissue and graft, or any combination thereof. As used herein, the term graft includes any of the following: homografts, autologous grafts, xenografts, allografts, alloplastic materials, and combinations of the foregoing. Tissue connector assemblies are disclosed, which, for example, may be used in vascular surgery to replace or bypass a diseased, occluded, or injured artery by connecting a graft vessel to a coronary artery or vein in an anastomosis as shown in FIGS. 16A-F or in FIGS. 19A-C. Assemblies constructed in accordance with the invention may be used in open surgical procedures or in minimally invasive or endoscopic procedures for attaching tissue located in the chest, abdominal cavity, or retroperitoneal space. It should be understood, however, that these examples are provided for illustration and are not intended to limit the scope of the invention.

Tissue connecting assemblies and methods are disclosed in copending U.S. patent application Ser. Nos. 09/089,884 and 09/090,305, both entitled Tissue Connector Apparatus and Methods and having a filing date of Jun. 3, 1998. The entirety of the disclosures of the cited '884 and '305 applications is hereby incorporated herein. One aspect of the present invention is the provision of multiple tissue piercing members. More specifically, tissue connecting assemblies constructed according to the present invention generally include a plurality of tissue piercing or penetrating members coupled to a surgical fastener. The multiple piercing member construction facilitates threading ends of the assembly from inner to outer wall(s) of material, such as tissue, which may eliminate or minimize the possibly of dislodging material, such as plaque, from the inner wall of calcified arteries, for example, as will become more apparent from the description provided below. In a preferred embodiment, two piercing members, each of which may comprise a needle, are releasably coupled to a fastener. One or both of the piercing members may be attached to a flexible member, such as a suture, which in turn is releasably coupled to the fastener. Double and single flexible member embodiments are illustrated in FIGS. 1 and 14, respectively. The coupling between the flexible member (and, thus, the piercing member) and the fastener may be constructed to actuate closure of the fastener upon release of the flexible member (or piercing member). For example, the coupling may hold a compression spring (which is positioned around a fastener) in a compressed state to brace the fastener open and releasably lock or secure the fastener to the flexible member (or piercing member).

A second double flexible member embodiment, also known as a dual clip assembly or as a bridge clip assembly, is illustrated in FIG. 17. This embodiment differs from the previous embodiments in that the fastener includes two clips separated by a bridge portion. Each clip is releasably attached to one flexible member and one piercing member. The biasing of each of the clips and the releasable coupling of the clips to the flexible member is similar to that of the previous embodiments. The fastener of this embodiment is particularly useful in facilitating tissue attachments, such as in guiding and aligning one tissue for attachment to a second tissue or for performing a horizontal mattress suture.

FIG. 1 illustrates one embodiment of a tissue connector assembly in accordance with the present invention. Referring to FIG. 1, a tissue connector assembly 11, which generally comprises tissue piercing or penetrating members 16 and 17, flexible members 18 and 19, and a fastener 20 (e.g., a surgical clip) is shown. A restraining device, generally indicated at 24 and comprising a spring (or coil) 26 and a locking device (or coupling member) generally indicated at 28, is connected to fastener 20 for holding the fastener in a deformed or open configuration as will be further described below. Although a particular fastener and accompanying restraining device is shown in FIG. 1, it should be understood that any suitable fastener can be used, including but not limited to the alternate fastener configurations described below. For example, the fastener may be a plastically deformable clip or may comprise two or more parts, at least one of which is movable relative to the other part, such as with a hinged clip. Further, other piercing member release mechanisms can be used with or without restraining devices depending, on the fastener construction.

Each of penetrating or piercing members 16 and 17 may be in the form of a needle (such as a 7-0 or 8-0 needle) having a sharp pointed tip (30 or 31) at its distal end for penetrating tissue. Members 16 and 17 may be bent as shown in FIG. 1, for example. The diameter of at least a portion of each of members 16 and 17 is preferably greater than the diameter of the respective flexible members (18 and 19), coupled thereto so that the flexible members can easily be pulled through an opening formed in the tissue (or other material) by the needle. The distal ends of the members 16 and 17 are preferably rigid to facilitate penetration of tissue. The remaining length of members 16 and 17 may be rigid or flexible to facilitate movement of the needle through the tissue as further described below. Tips 30 and/or 31 may have various configurations and may, for example, be conical, tapered, or grounded to attain a three or four facet tip. Members 16 and 17 may be made from stainless steel or any other suitable material, such as a polymeric material. It is to be understood that members 16 and 17 may have a shape or radius of curvature other than the one shown, without departing from the scope of the invention. Members 16 and 17 may also be integrally formed with the flexible member 18 (e.g., both piercing member and flexible member formed of the same material).

The flexible members 18 and 19 may be in the form of a suture formed from conventional filament material, metal alloy, such as nitinol, polymeric material, or any other suitable material. The material may be non-stretchable or stretchable, solid or hollow (as shown, for example, in FIGS. 2A and 2B), and have various cross-sectional diameters. The flexible members or sutures may have a cross-sectional diameter of 0.003 inch, and lengths ranging from about 10 mm to about 300 mm, for example. The diameter and length of the suture will vary depending on the specific application. The sutures may be attached to the piercing members 16 and 17, respectively, by crimping or swaging the piercing member or needle onto the suture, gluing the suture to the piercing member or needle, or any other suitable attachment method. Flexible members 18 and 19 may have cross-sectional shapes other than the one shown herein and may have other constructions as well.

Referring to FIG. 2A, an alternate flexible member construction is shown. Flexible member 18' generally comprises a flexible filament 14, which may be in the form of a metal wire, and tube or sleeve 15, which may be in the form of a hollow suture. Tube 15 surrounds filament 14 with one end of the filament 14 secured to piercing member 16 and its other end secured to coupling 28 with glue, for example. The filament may provide kink resistance and pull strength (to minimize or eliminate stretch), and is especially advantageous when using very thin material for tube 15. Tube 15 may, for example, comprise polymeric materials such as polyurethane or polyester. It is noted that at least the portions of the tube adjacent to needle 16 and coupling 28 have the same diameter as the portions of the coupling and needle adjacent thereto. This eliminates the need for the tapered portions 2 and 3 shown in FIG. 1 or other transition sections to minimize or eliminate the step between the flexible member and needle and/or the flexible member and the coupling. Of course, the diameter of the entire flexible member may be the same as that of the coupling and the portion of the needle adjacent to the flexible member as indicated in FIG. 2A. It also should be apparent from the foregoing that the construction of flexible member 18' may be substituted for flexible member 19.

Referring to FIG. 2B, another hollow flexible member construction is shown. Flexible member 18" comprises tube or sleeve 15, which may be in the form of a hollow suture. Tube 15 is secured to piercing member or needle 16 and coupling 28 through posts or anchors 4, which in turn, are secured to piercing member or needle 16 and coupling 28. The relative dimensions of tube 15 as compared to needle 16 and coupling 28 may be the same as those describe in connection with FIG. 2A for the same reasons. Further, flexible member 18" may be substituted for flexible member 19 as well.

Referring to FIGS. 3-6, fasteners, which were shown in copending U.S. patent application Ser. Nos. 09/089,884 and 09/090,305 and which may be used in the present invention, first will be described. Referring to FIGS. 3A-C, one embodiment of a fastener (e.g., fastener 20) comprises a deformable wire 34 made of a shape memory alloy. A nickel titanium (nitinol) based alloy may be used, for example. The nitinol may include additional elements that affect the yield strength of the material or the temperature at which particular pseudoelastic or shape transformation characteristics occur. The transformation temperature may be defined as the temperature at which a shape memory alloy finishes transforming from martensite to austenite upon heating (i.e., $A_f$ temperature). The shape memory alloy preferably exhibits pseudoelastic (e.g., superelastic) behavior when deformed at a temperature slightly above its transformation temperature. At least a portion of the shape memory alloy is converted from its austenitic phase to its martensitic phase when the wire is in its deformed configuration. As the stress is removed, the material undergoes a martensitic to austenitic conversion and springs back to its original undeformed configuration. When the wire is positioned within the tissue in its undeformed configuration, a residual stress is present to maintain the tissue tightly together (see e.g., FIG. 16F). In order for the pseudoelastic wire 34 to retain sufficient compression force in its undeformed configuration, the wire should not be stressed past its yield point in its deformed configuration to allow complete recovery of the wire to its undeformed configuration. The shape memory alloy is preferably selected with a transformation temperature suitable for use with a stopped heart condition where cold cardioplegia has been injected for temporary paralysis of the heart tissue (e.g., temperatures as low as 8-10 degrees Celsius).

It is to be understood that the shape memory alloy may also be heat activated, or a combination of heat activation and pseudoelastic properties may be used, as is well known by those skilled in the art.

The cross-sectional diameter of wire 34 and length of the wire will vary depending on the specific application. The diameter "d" of wire 34 may be, for example, between 0.001 and 0.015 inch. For coronary bypass applications, the diameter is preferably between 0.001 and 0.008 inch with a diameter "D" of the loop (FIG. 3A) being between 0.0125 and 0.0875 inch. As shown in FIGS. 3A and 3B, wire 34 may have a circular cross-sectional shape and a generally ring or loop shaped configuration when in a closed position. The diameter "D" of the loop of the fastener 20 (with coil 26, which may be platinum) in its closed position is preferably sized to prevent movement between adjacent tissues. It is to be understood, however, that the wire may have other cross-sectional shapes such as rectangular, or may be formed from multiple strands without departing from the scope of the invention.

One end of wire 34, which may be referred to as the proximal end of wire 34, may include an enlarged portion 36 having a cross-sectional area greater than the cross-sectional area of the wire to resist the coil from passing thereover. The enlarged portion 36 also may be provided to cooperate with a release mechanism as will be discussed in more detail below. Enlarged portion 36 may be formed by attaching a member to the end of wire 34 by welding, gluing or other suitable attachment means or may be formed integrally with the wire by deforming the end of the wire. The other end of wire 34, which may be referred to as the distal end of wire 34, also may include an enlarged portion 38 for engagement with a restraining device, such as restraining device 24 (see. e.g., FIG. 1), or a locking device or release mechanism, such as release mechanism 28 (see e.g., FIG. 1), as further described below. The enlarged portion 38 may be formed by deforming the end of the wire 34 by swaging or arc welding, or attaching an enlarged portion to the end of the wire by welding, swaging, or other suitable means. Although enlarged portions 36 and 38 are shown with spherical and cylindrical configurations, other configurations or configuration combinations can be used. For example, both enlarged portions may be spherical or cylindrical, or portion 36 may be cylindrical and portion 38 spherical.

Referring to FIGS. 3A-C, fastener 20 is shown in open and closed configurations. When wire 34 is in an undeformed or closed configuration, the fastener is closed (as shown in FIGS. 3A and 3B) for keeping or connecting tissue together, and when wire 34 is in a deformed or open configuration, the fastener is open (as shown in FIG. 3C) for insertion of the wire into tissue. As discussed above, wire 34 is in its closed configuration when in a relaxed state. Wire 34 is preferably not deformed past its yield point in its open position. Accordingly, it may have a U-shaped configuration in its open position to facilitate insertion of the wire through the tissue. It is to be understood that U-shaped configuration may be alternatively substituted by an equivalent structure such as C-shaped, V-shaped, J-shaped, and other similarly shaped configurations. Wire 34 is moved from its closed position to its open position by a restraining device, as further described below. When in its closed position, wire 34 forms a loop with the ends of the wire in a generally side-by-side or overlapping orientation (FIG. 3B).

Wire 34 may be formed in the above-described shape by first wrapping the wire onto a mandrel and heat-treating the wire at approximately 400-500 degrees Celsius for approximately 5 to 30 minutes. Wire 34 is then air quenched at room temperature. The mandrel may have a constant diameter or may be conical in shape.

Referring to FIG. 4, an alternate configuration of fastener 20 in its closed position is shown, and generally indicated with reference numeral 40. Fastener 40 forms a spiral configuration in its closed position for trapping the tissue within a loop formed by the spiral. In its open position, the fastener 40 is configured to form less than a full 360 degree turn, and may be made to have an open position as shown in FIG. 3C, for example.

Referring to FIGS. 5A and 5B, another configuration of fastener 20 is shown in its closed position, and is generally designated with reference numeral 41. Fastener 41 is formed in a spiral about a central longitudinal axis A. As shown in FIG. 5B, fastener 41 has a generally conical shape along the longitudinal axis A, with a decreasing diameter as the radius of curvature of fastener 41 decreases. Fastener 41 has an inner end portion 45 and an outer end portion 47, with the enlarged portion 38 of the wire being disposed at the outer end portion for engagement with the restraining device 24 as shown, for example, in FIG. 3C.

Referring to FIG. 6, a modification of fastener 41 is shown, and generally indicated with reference numeral 43. Fastener 43 is similar to fastener 41 described above, except that enlarged portion 38, which is adapted for engaging a restraining device or releasable locking mechanism, is positioned at the inner end portion 45 of the fastener. Placement of restraining device 24 at the inner end portion 45 of fastener 43 increases the compression force of the wire in its undeformed position on the tissue and decreases the surface area of the fastener exposed to blood flow.

It is to be understood that the fasteners may have undeformed or deformed configurations different than those shown herein without departing from the scope of the invention. In addition, a locking clip (not shown) may also be attached to connect the ends of the fastener (such as fastener 20, 40, 41, 43) when the fastener is in its closed position to prevent possible opening of the fastener over time. The locking clip may also be integrally formed with one end of the fastener.

As shown in FIG. 3C, wire 34 is surrounded by spring or coil 26 that, along with the locking device 28, restrains the wire in its deformed configuration. Coil 26 comprises a helical wire forming a plurality of loops that define a longitudinal opening 44 for receiving the shape memory alloy wire 34. Coil 26 may be formed from a platinum alloy wire having a cross-sectional diameter of approximately 0.0005-0.005 inch, for example. The helical wire may have other cross-sectional shapes and be formed of different materials. Coil 26 is preferably sized so that when in its free (uncompressed state) it extends the length of wire 34 with one end adjacent the enlarged portion 36 at the proximal end of the wire and the other end adjacent enlarged portion 38 at the distal end of the wire. It is to be understood that the coil may not extend the full length of the wire. For example, a flange or similar device may be provided on an intermediate portion of wire 34 to limit movement of the coil along the length of the wire.

When coil 26 is in its free state (with the wire in its undeformed configuration), loops of the coil are generally spaced from one another and do not exert any significant force on the wire 34 (FIGS. 3A and 3B). When the coil 26 is compressed (with the wire 34 in its deformed configuration), loops of the coil on the inner portion 46 of the coil are squeezed together with a tight pitch so that the loops are contiguous with one another while loops on the outer portion 48 of the coil are spaced from one another (FIG. 3C). This is due to the compressed inner arc length of coil 26 and the expanded outer arc length of the coil. The compression of the loops on the inner portion 46 of coil 26 exerts a force on the inner side of wire 34 which forces the wire to spread open (i.e., tends to straighten the wire from its closed configuration to its open configuration). The end of coil 26 adjacent enlarged portion 36 is held in a fixed position relative to wire 34. The opposite end of coil 26 is free to move along wire 34 and is held in place when the coil is in its compressed position by locking device 28. It should be understood, however, that a coil (not shown) having sufficient stiffness, for example, might be used where adjacent loops do not contact one another when the coil is compressed to force wire 34 into an open position.

Referring to FIGS. 7A-7C, one embodiment of a releasable locking device or release mechanism, which is disclosed in U.S. patent application Ser. Nos. 09/089,884 and 09/090,305, is shown. Releasable locking device 28a is adapted for releasably coupling a fastener (such as any of the fasteners shown in FIGS. 3-6) to a flexible member (such as flexible member 18, 18' or 18") is shown and generally designated with reference numeral 28a. Release mechanism 28a comprises a flexible tubular member 50 having a distal end portion 52 and is shown with tapered section or sleeve 2, which in turn is coupled to the flexible member. Tapered section or sleeve 2, which provides a transition between the flexible member and fastener for insertion of the fastener through tissue, may be a separate member coupled to tubular member 50 or be formed integrally therewith. Tubular member 50 further includes a proximal end portion 54 releasably attached to wire 34. In this manner, release mechanism 28a releasably couples the flexible member and needle to the surgical fastener such as fastener 20. In addition to releasably coupling the flexible member and needle to the fastener, the locking device or release mechanism compresses coil 26 to bias the fastener or surgical clip 20 in its open configuration, facilitating insertion of the locking device 28 through tissue. Although a straight tapered section is shown, it may be curved as well. Tapered portion 2 may be formed from a metal alloy such as stainless steel or a suitable polymeric material and may be solid or in the form of a sleeve as noted above. Generally, tapered section 2 gradually diminishes in diameter to provide a smooth, non-stepped transition between the relatively small diameter of the flexible member to the larger diameter of locking device such as locking device 28a. The flexible member such as flexible member 18 may be swaged into the tapered section, or a heat shrink plastic covering may hold the flexible member in place. The locking device may also be curved.

Tubular member 50 is movable between a locked position (FIGS. 7A and 7B) for holding coil 26 in its compressed position and wire 34 in its deformed position, and an unlocked position (FIG. 7C) for inserting or releasing the wire and coil. Referring to FIGS. 7B and 7C, three slots 58 are shown formed in tubular member 50 extending from the proximal end 54 of the member and along at least a portion of the member. Slots 58 are provided to allow the proximal end 54 of tubular member 50 to open for insertion and removal of the wire 34. It is to be understood that the number of slots 58 and configuration of the slots may vary, or tubular member 50 may be formed to allow expansion of proximal end 54 without the use of slots.

Proximal end 54 of tubular member 50 includes a bore 62 having a diameter slightly greater than the outer diameter "d" of wire 34, but smaller than the diameter of enlarged portion 38 at the distal end of the wire and the outer diameter of the coil 26. Bore 62 extends into a cavity 64 sized for receiving the enlarged portion 38 of wire 34. Tubular member 50 may be described as having an annular flange 61 for releasably securing enlarged portion 38. As shown in FIG. 7C, upon application of an inwardly directed radial squeezing force on the tubular member 50 proximal end 54 of the tubular member is opened to allow for insertion or removal of wire 34. When the force is released, the tubular member 50 moves back to its locked position and securely holds wire 34 in place and compresses the coil 26 as shown in FIG. 7A. A disc 51 may be inserted into tubular member 50 to act as a fulcrum and cause the proximal end 54 of the tubular member to open. Alternatively, disc 51 may be integrally formed with tubular member 50. As shown in FIG. 7A, the length l of the bore 62 or flange 61 determines the amount of compression of the coil, which in turn determines the amount of deformation of wire 34. The greater the length l of bore 62, the greater the compression of coil 26 and the more straightening of wire 34 will undergo. The compression of coil 26 is preferably limited so that wire 34 is not stressed beyond its yield point. This allows wire 34 to revert back to its original undeformed configuration and apply sufficient pressure to hold the connected tissue together.

FIGS. 8A, 8B and 8C illustrate another release mechanism which is generally designated with reference numeral 28b. FIGS. 8A and 8B show the release mechanism in a locked position, and FIG. 8C shows the release mechanism in an unlocked position. Release mechanism 28b comprises a tubular member 80, which has proximal and distal ends 88 and 89, respectively. Tubular member 80 further includes bore 82 formed therein and a cavity or recess 84 extending radially outward from bore 82 into the tubular member. Recess 84 is configured to receive enlarged portion 38 or wire 34 as best illustrated in FIG. 8A. Recess 84 and bore 82 form an annular flange 86, which has an inner diameter less than that of enlarged portion 38 and, thus, resists removal of the enlarged portion. In the embodiment shown in FIGS. 8A-C, three slots 87 are formed in tubular member 80 as in the embodiment shown in FIGS. 7A-C. The slots extend longitudinally from the proximal end 88 of tubular member 80 and form fingers 81, which radially expand and release wire 34 upon radial compression of the tubular member as shown in FIG. 8C and as described above in connection with release mechanism 28a. In this embodiment, however, enlarged portion 38 forms a fulcrum. Although three equiangularly spaced slots, which extend parallel to the longitudinal axis are shown as in release mechanism 28a, the number and configuration of the slots may vary, or the tubular member may be formed to allow expansion of the proximal end portion without the use of slots. A tapered section 2 also may be provided as described above in connection with release mechanism 28a.

FIGS. 9A-9E illustrate yet another release mechanism which is disclosed in U.S. patent application Ser. No. 09/259,705, filed on Mar. 1, 1999 and entitled Tissue Connector Apparatus With Cable Release. The release mechanism is generally indicated with reference numeral 28c in FIGS. 9A-9E where FIGS. 9A-C show the mechanism coupled with a fastener, and FIGS. 9D and 9E show the release mechanism depressed for release of the fastener. Locking device or release mechanism 28c comprises a plurality of substantially rigid strands, preferably wires 106, arranged substantially parallel to one another and circularly about a longitudinal axis of the aligned strands, to form a tube-like configuration, as can be seen in the cross-sectional view of FIG. 9C and the perspective view in FIG. 9A. Alternatively, strands 106 may be cables or some other substantially rigid strand elements arranged in the same manner as the wires shown in FIG. 9C. Upon arrangement into the circular configuration, the hidden end portions 106a of the strands are coupled to tapered section 2, which is coupled to a piercing member or needle through a flexible member such as flexible member 18.

Preferably, a rod 162 extends from tapered section 2 to facilitate fixation of the strands thereto. The coupling of the strands to tapered section 2 is preferably accomplished by gluing or soldering to rod 162, although other equivalent or similar known joining techniques may be employed (e.g. welding, threadably attaching, etc). Similarly, rod 162 is preferably glued, soldered or threaded into the needle or transition element. In an alternate arrangement, the flexible member may extend through tapered section 2 and form a substitute structure for rod 162. This may be preferred when the flexible member is a metal wire.

The end portions 106b of the strands in the vicinity of the fastener strands include notches 109 which are formed into the strands to a depth equal to approximately half the diameter of the strand 106. When the strands are arranged in the circular configuration described above, the notches 109 form a chamber 108 configured for receiving and holding enlarged portion 38. Although enlarged portion 38 is shown as having a spherical shape, it may have other shapes including a barrel shape, or other shape that may be easily grasped and easily released. The notches are preferably placed about 0.015" from the free ends of the strands, but this distance, of course, can be modified, depending upon the amount of compression of spring 26 that is desired when ball 38 is inserted into and held by notches 109.

After placement of ball 38 within chamber 108 formed by notches 109, a shrink wrap layer, preferably a shrink tubing 110 may be provided over at least free end portions 106b of wires or strands 106, and the tubing heated to compress against strands 106 and hold them in place against ball 38, preferably symmetrically against ball 38. Together, tubing 110 and strands 106 effectively hold ball 38 captive within notches 109. Alternatively, other plastic or elastic restraining members may be mounted around the distal portions of the wires or strands to aid in maintaining them in place, preferably symmetrically against ball 38. Still further, strand members may be designed with an elastic spring force sufficient to maintain notches 109 in place with sufficient force to maintain the ball 38 captive therein under the tensile forces normally experienced during a suturing procedure. Although a seven-strand embodiment is shown, it should be understood that fewer or more than seven strands may be used. The number of strands may vary depending on, for example, the size of the clip or the size of the strands. Typically, the number of strands may range from two to ten. In a coronary anastomosis, the number of strands preferably will range from five to seven although other numbers may be used.

In assembling, enlarged portion 38 of wire 34 is placed in chamber 108. Tubing 110 is wrapped around at least a portion of the strands (as shown in the drawings) and heated to maintain enlarged portion 38 captive within the cavity formed by the strands. Compression coil or spring 26 is slid over wire 34 and compressed against portions 106b such that the fastener is in its open configuration. Enlarged portion 36 may then be formed or attached to wire 34 to maintain the fastener in its open configuration.

Release mechanism 28c is movable between a locked position (FIGS. 9A-9c) and an unlocked position (FIGS. 9E and 9F). In the locked position the ball 38 is held within notches 109 and consequently, coil 26 is held in its compressed position, thereby maintaining fastener wire 34 in its deformed or open position. In the unlocked position, ball 38 is released from the notches, thereby allowing the coil 26 to expand, which causes the fastener wire 34 to close. The closure conformation of the wire may be characterized by any of those described above with reference to FIGS. 3-6, for example.

Movement of the release mechanism to the open position is accomplished by applying a compressive force to the shrink tube 110 and bundle of strands 106, as shown in FIGS. 9D and 9E. Advantageously, the compressive force may be applied at any opposing locations around the circumference of the shrink tube as long as the implement applying the force is oriented at an angle to the strands, preferably substantially perpendicular thereto, to allow the implement to traverse the strands so as to deform the positions thereof when the force is applied. For example, needle holder 111 could be rotated 90° (or virtually any other angle) with respect to the strands 106 as shown in the plane of the drawing, while retaining the capability of deforming the strands to an open position upon application of a compressive force. The compressive force is preferably applied using a standard needle holder 111 or forceps, although other tools could be used, preferably those with applicators narrower than the length of the shrink tube 110. As shown, the strands or wires 106 get distorted from their circular configuration under the compression. This change in shape stretches the shrink tube 110 from a circular configuration to a somewhat elliptical configuration, and removes some of the notches 109 from contact with ball 38, thereby permitting removal of ball 38 from within the chamber previously formed by notches 109 in the closed position.

Referring to FIG. 9F, release mechanism 23c also may be used to releasably couple the other end of the fastener to another flexible member such as flexible member 19, which in turn, is coupled to a needle such as needle 17 as shown in FIG. 1. In this arrangement, a member or stopper 115, which may be annular, is secured to the other end of the fastener or wire 34 to prevent enlarged portion 36 from passing through the compression spring upon release from release mechanism 23c. Other release mechanisms, which provide synchronized release of both needles illustrated in FIG. 1, also can be used.

Figure 10B:
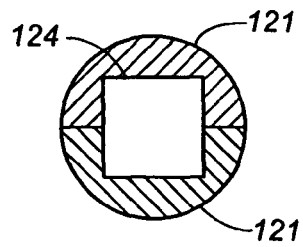
Figure 10C:
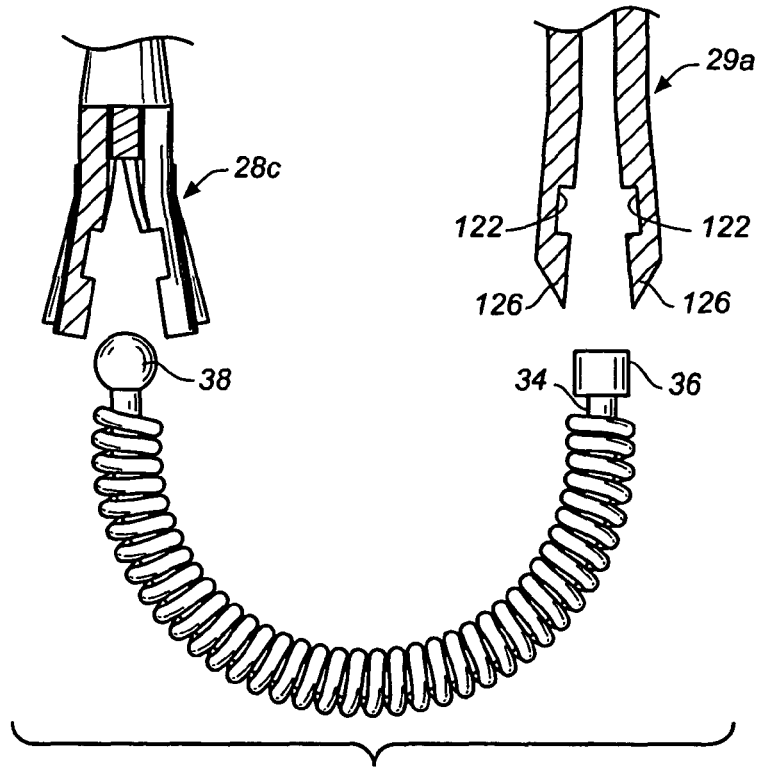

FIGS. 10A-10F illustrate synchronized fastener release systems. Referring to FIGS. 10A-10C, a first synchronized release system is shown in a coupled and decoupled state, respectfully. Although one release mechanism is shown as corresponding to release mechanism 28c, release mechanisms 28a or 28b or any release mechanism which releasably couples the flexible member or needle to the surgical fastener and effects compression of coil 26 also may be used. At the other end of the fastener or wire 34, a release mechanism that responds to the compressive state of coil 26 and releases the fastener or wire 34 upon release of compressive forces on the coil is shown and generally designated with reference numeral 29a. Release mechanism 29a comprises two members 121 each having a recess 122 formed therein and arranged to form chamber 124 when members 121 are aligned as shown in FIG. 10A. Recesses 122 are configured to retain enlarged portion 36, which is shown with a cylindrical configuration, but may have a spherical or other suitable shape for operatively associating with a suitably configured chamber. Further, members 121 may have semicircular transverse cross sections or some other combination of transverse shapes that can collectively provide the desired chamber to retain enlarged portion 36. The number of members 121 also may vary as would be apparent to one of ordinary skill.

Release mechanism members 121 have tapered ends 126, which are configured for positioning between coil 26 and fastener wire 34 as shown in FIG. 10A. When tapered ends 126 are so positioned and coil 26 is in a compressed state, coil 26 holds tapered ends 126, which are normally biased away from each other as shown in FIG. 10C, sufficiently together to retain enlarged portion 36 within chamber 124. When release mechanism 28c is actuated (e.g., radially compressed) to release enlarged portion 38 of fastener wire 34, coil 26 assumes its relaxed state, thereby releasing tapered ends 126 of release mechanism 29a from the coil and allowing the tapered ends to radially expand and release enlarged portion 36 of fastener wire 34 as shown in FIG. 10C. Accordingly, both needles and flexible members may be decoupled from the fastener when release mechanism 28c is actuated.

FIGS. 10D-10F show another synchronized fastener system that is the same as the system shown in FIGS. 10A-10C with the exception of release mechanism 29b and the cooperating portion of the fastener or wire 34 being substituted for release mechanism 29a. In this embodiment, an annular member or stopper 115, which may be annular, is slidably coupled to fastener wire 34. Member 115 is configured to resist passage of coil 26 thereover. Accordingly, member 115 may have an outer diameter slightly greater than at least the portion of the coil adjacent thereto. A tapered or frustoconical member 3' is secured to an end of fastener wire 34, which need not include an enlarged portion. Member 3' is the same as member 3 with the exception that member 3' has a channel 134 for receiving flexible member or suture 19. Channel 134 extends radially outward from bore 132, which is formed through member 3', for receiving the fastener or wire 34.

Flexible member 19 is threaded through channel 134 and between tapered member 3' and annular member 115. When coil 26 is in a compressed state as shown in FIG. 10D, the coil urges member 115 toward tapered member 3' and compresses flexible member 19 therebetween. In this manner, flexible member 19 is secured to the fastener or wire 34. When release mechanism 28c is actuated (e.g., radially compressed) to release enlarged portion 38 of the fastener or wire 34, coil 26 assumes its relaxed state so that annular member 155 may slide away from tapered member 3' and release flexible member 19. Accordingly, both needles and flexible members may be removed from the fastener when release mechanism 28c is actuated. Although a metal flexible member may be used, a polymeric flexible member may be preferred.

FIGS. 11A and 11B show another release mechanism generally indicated with reference numeral 29c. Release mechanism 29c includes a sleeve 142, which is slidably mounted over flexible member 19 so that it can be positioned over the flexible member and the fastener or wire to releasably hold the flexible member and the fastener together. The end portion of the flexible member opposite the needle and the end portion of the fastener or wire to be engaged therewith may be configured to provide interlocking engagement therebetween. In the embodiment shown in FIGS. 11A and 11B, the flexible member, which preferably is metal in this example, and the fastener or wire end portions have mating flange and groove configurations. Flexible member 19 includes groove 144a and flange 146a, which mate with or interlockingly engage groove 144b and flange 146b, which are formed in wire 34. When sleeve 142 is moved away from the fastener or wire, the coupling becomes unrestrained and the flexible member and the fastener or wire can be readily separated by removing flanges 146a and 146b from grooves 144a and 144b as shown in FIG. 11B. Member 115 may be secured to fastener wire 34 to prevent the end of coil 26 adjacent to groove 144b and flange 146b from sliding thereover. Member 115 also may be described as a stopper for spring 26.

FIGS. 12A and 12B show another release mechanism, which is generally designated with reference numeral 29d. In this embodiment, tapered member 3 is provided with a bore for receiving both flexible member 19 and the fastener or wire 34. Member or collar 115 may be fixedly secured to the fastener or wire 34 to resist coil movement over the wire and toward the flexible member. The fastener or wire also may be fixedly secured to the inner wall of tapered member 3 by, for example, gluing or welding. One end of the flexible member is tied into a knot such as knot 150. The knot is packed into the bore 152 and the tapered member is swaged or crimped as shown in FIGS. 12A and 12B to secure the knot in the bore. The flexible member is cut as shown in FIG. 12B to decouple the flexible member from the fastener.

FIGS. 13A and 13B illustrate a further release mechanism, which is generally designated with reference numeral 29e. Release mechanism 29e generally comprises a release member having a cavity formed therein to receive the fastener or wire 34 and a portion configured for severing the fastener wire. This advantageously eliminates the need for a separate cutting tool to separate the suture or needle from the fastener. One example of such a release member is shown as release member 160. Release member 160 has one end that is fixedly secured to tapered member 3 to which flexible member 19 is secured. Alternatively, members 3 and 160 may be integrally formed. Release member 160 is configured to form a cavity 162 therein and may be in the form of a sleeve. Member 160 includes annular flange 164 through which fastener wire 34 is received. Annular flange 164 includes an annular lip 166, which forms a cutting surface or annular blade. Release member 160 also may include an opening for receiving flexible member 19 therethrough as shown in FIGS. 13A and 13B. In this example, release member 160 can be fixedly secured to flexible member 19, which, in turn, can be fixedly secured to tapered member 3. Of course, it should be understood that members 160 and 3 can be directly secured to one another or integrally formed as a single piece. When release member 160 is radially compressed as shown in FIG. 13B, annular lip severs fastener wire 34 and decouples flexible member therefrom. Fastener wire 34 may be provided with annular groove 168 to enhance wire fracture. Release member 160 or annular lip 166 may be 400 series stainless steel or tool steel to facilitate hardening. Other materials that tend to provide an effective cutting tool also may be used. Release member 160, however, should comprise material that provides the desired flexibility. Further, it should be understood that although release member 160 is shown with a generally cylindrical configuration, other configurations may be used. In assembly, member 115, which may be annular, may be swaged, glued or welded to wire 34 to compress coil 34 after the other end of wire has been secured to a locking device or coupling so that the fastener opens as may be done in the embodiments of FIGS. 11A and B and 12A and B. Wire 34 may be preformed with groove 168 or the groove formed prior to sliding member 160 over wire 34 so as to engage blade 166 with the groove.

It is to be understood that locking devices other than those described above may be used without departing from the scope of the invention. For example, a locking device (not shown) may comprise a tubular member having an opening formed in a sidewall thereof for receiving an end portion of the wire. The end of the wire may be bent so that it is biased to fit within the opening in the sidewall of the tubular member.

An instrument, such as a needle holder may then be used to push the wire away from the opening in the tubular member and release the wire from the tubular member. Various other types of locking devices including a spring detent or bayonet type of device may also be used. Further, the fastener or wire end portions may be configured differently than that shown. For example, one or both of the fastener or wire end portions may be provided with grooves instead of enlarged portions and the release mechanisms or locking device arms, such as, for example, fingers 81 or strands 106, may be provided with projections to releasably engage with the grooves.

FIG. 14A is a front view of another embodiment of a tissue connector assembly of the present invention which is generally designated with reference numeral 211. Tissue connector assembly 211 is the same as tissue connector assembly 11 with the exception that locking device or release mechanism 28 is directly connected to needle 16. Although any of the release mechanisms 28*a-c* may be used to couple the fastener to needle 16, release mechanism 28*c* is shown in FIG. 14B for purposes of illustrating a connection between a locking device and needle 16.

Referring to FIG. 14B, rod 162 extends from needle 16. Rod 162 and needle 16 may be integrally formed or be separate elements secured which are fixed to one another. The coupling of strands 106 to the needle is preferably accomplished by gluing or soldering to the rod 162, although other equivalent or similar known joining techniques may be employed (e.g. welding, threadably attaching, etc). Similarly, when the rod and needle are discrete elements, the rod is preferably glued, soldered or threaded into the needle. Alternately, rod 162 may extend from or be affixed to a transition element that in turn is affixed to needle 16.

FIG. 15 is a front view of a lateral tissue connector which is generally designated with reference numeral 300 and which can be used in conjunction with any of the assemblies described above as will be described in detail below. Tissue connector assembly 300 generally includes needle 16, a locking device or release mechanism, and a fastener, which may be fastener 20, 40, 41, or 43, for example. In this embodiment, needle 16 is attached directly to a locking device, such as locking device 28*c*, a connection for which is described above with reference to FIG. 14A. FIG. 14A shows tissue connector assembly 211 with the fastener in its open (deformed) configuration.

FIG. 17 is a front view of a bridge clip embodiment of a tissue connector assembly of the present invention, generally designated with reference numeral 1701. Tissue connector assembly 1701 includes a bridge clip 1707 having a pair of clips or fasteners 1703 and a connecting bridge 1705. Each of the pair of clip and components corresponding to each of the pair of clips is denoted with a prime or double-prime. Thus, for example, the pair of clips 1703 includes a first clip 1703' and a second clip 1703". In one embodiment, the materials and configuration of assembly 1701 are essentially symmetric, and corresponding primed and double-primed components are mirror images of one another. In another embodiment, tissue connector assembly is not symmetric, and thus a primed component and the corresponding double-primed component may be of different materials or geometry, or may be constructed differently but be functionally equivalent.

Each one of clips 1703 includes wire 34 surrounded by a corresponding coil 26, that can provide a bias force to keep each clip in an open configuration. Clips 1703 may be fastener 20, 40, 41, 43, or other similar fasteners. The end portion of each coil 26 near bridge 1705 is restrained by a corresponding stopper 115 attached to wire 34, while the opposite end of the coil can be restrained by a corresponding release mechanism 28. As with the embodiment of FIG. 1, the free ends of fasteners 1703 are releasably coupled through the release mechanisms 28 to flexible members 18, and to piercing members 16, respectively. The two clips 1703 are thus seen to act as two clips similar to fastener 20 of FIG. 1, joined together near their respective stoppers 115. In the preferred embodiment, wires 34' and 34" are two sections of a single wire 34 that is made of a shape memory alloy that has be heat treated to form the double-loop configuration described herein. The bridge clip 1707 can be assembled by heat treating wire 34 to the closed configuration, as describe previously, threading stoppers 115 followed by coils 36 over wires 34, mounting the release mechanisms 28, moving stoppers 115' and 115" apart to produce the required biasing force on the wire, and then crimp, swage or weld the stoppers to the wire. An assembly 1701 thus assembled will maintain the configuration of FIG. 17 until the biasing force of one of coils 26 is released.

For a symmetric tissue connector assembly 1701 embodiment noted in the previous embodiment, each of clips 1703 are constructed of the same materials, with clip 1703' and clip 1703" being mirror images. Examples of tissue connector assembly 1701 that is not symmetric, include, but are not limited to having clips 1703' and 1703" of different sizes or shapes, having coils 26' and 26" produce different biasing forces, or having flexible members 18 of different lengths, sizes or materials.

FIG. 18 shows the configuration of the bridge clip 1707 of FIG. 17 after actuation of release mechanisms 28. Upon release of release mechanisms 28, coils 26 move towards enlarged portions 36, reducing the biasing force and allowing clips 1703 to move towards the closed configuration, as shown. Thus in addition to causing the release of bridge clip 1707 from flexible members 18, actuation of release mechanisms 28 also triggers a self-closing action causing the clip to transition from the open configuration of FIG. 17 towards the closed configuration of FIG. 18. The separation and orientation of clips 1703' and 1703" are fixed by the heat-treated configuration of the wire. Thus in one use, bridge clip 1707 can be used to secure tissue at two positions (through the loops of clips 1703' and 1703") that are accurately determined by the separation provided by bridge 1705.

As an alternative embodiment, coils 26' and 26" can be replaced with one coil (not shown) that is coupled to both release mechanisms 28, and which supplies a biasing force to keep both of clips 1703 biased in an open position. Release of either of either of release mechanisms 28' or 28" partially releases the biasing force, causing both clips 1703 to return to a partially closed position. Release of the other of release mechanism 28 decreases the biasing force to allow both of clips 1703 to return to a fully closed position. There are many alternative embodiments for the various components of tissue connector assembly 1701. Thus for example, flexible members 18 can be constructed as shown in one of FIG. 2A or 2B or other structures as described previously. Additionally, the discussion of release mechanisms described in reference to FIGS. 7 through 11 can also be applied, separately or in combination to the two release mechanisms 28 of tissue connector assembly 1701.

The shape of bridge clip 1707 when released from flexible members 18 is shown in FIG. 18. With release mechanisms 28 of FIG. 17 released, both self-closing fasteners 1703 become unbiased and assume the closed configurations of FIG. 18. In the closed configuration the bridge 1705 is clearly seen to be a nearly straight portion that is formed between the two closed clips 1703. In a specific embodiment, fasteners 1703 are formed of a memory shape alloy. By forming the clip material in the shape shown in FIG. 18, the two fasteners 1703 are connected by a fairly rigid bridge portion 1705. One particularly useful embodiment orients loop of clips 1703 at right angles to bridge 1705. It can be seen in the figure, and by subsequent descriptions, that the closed fastener of FIG. 18 can be used to hold tissue at two positions (one at by each clip loop) separated by the distance of the bridge 1705. The bridge clip 1707 thus can be used to secure tissue at two locations with the loops of fasteners 1703, with the locations supported by the bridge 1705. Bridge clip 1707 can thus be used to hold tissues together at two separate locations, or by application of pressure by bridge 1705 onto fasteners 1703, pressure may be applied along the length of the bridge clip. Specific uses of bridge clip 1707 include, but are not limited to, providing anchoring of the fastener against the tissue, and as such are useful in many of the attachment procedures described previously, and attaching tissues as for example, as a type of horizontal mattress suture.

As noted above, tissue connector assemblies described above have many uses. They may be especially useful for minimally invasive surgical procedures including creating an anastomosis between a vascular graft 12 and an artery 14. The anastomosis may be used to replace or bypass a diseased, occluded or injured artery. A coronary bypass graft procedure requires that a source of arterial blood flow be prepared for subsequent bypass connection to a diseased artery. An arterial graft may be used to provide a source of blood flow, or a free graft may be used and connected at the proximal end to a source of blood flow. Preferably, the source of blood flow is one of any number of existing arteries that may be dissected in preparation for the bypass graft procedure. In many instances it is preferred to use the left internal mammary artery (LIMA) or the right internal mammary artery (RIMA), for example. Other vessels which may be used include the saphenous vein, gastroepiploic artery in the abdomen, radial artery, and other arteries harvested from the patient's body as well as synthetic graft materials, such as DACRON® (polyester fibers) or GORETEX® (expanded polytetrafluoroethylene). If a free graft vessel is used, the upstream end of the dissected vessel, which is the arterial blood source, will be secured to the aorta to provide the desired bypass blood flow, as is well known by those skilled in the art. The downstream end of the graft vessel is trimmed for attachment to an artery, such as the left anterior descending coronary (LAD). It is to be understood that the anastomosis may be formed in other vessels or tissue.

FIGS. 16A-16D diagrammatically illustrate a method of aligning and connecting graft and target vessels, such as connecting a graft vessel 12 to an artery 14 (target vessel) using tissue connector assemblies 11 and 300. In this example, two tissue connector assemblies 11 are used to make connections at generally opposite sides of the graft vessel and tissue connector assemblies 300 are used to make connections between those made with assemblies 11. The procedure may be accomplished with a beating heart procedure with the use of a heart stabilizer to keep the heart stable, for example. The procedure may also be performed endoscopically. It also should be understood that tissue connector assemblies 211 may be substituted for assemblies 11.

The patient is first prepped for standard cardiac surgery. After exposure and control of artery 14, occlusion and reperfusion may be performed as required, an arteriotomy is performed on artery 14 to provide an opening 120 for receiving a graft vessel. After the snared graft vessel 12 has been prepared as would be apparent to one of ordinary skill in the art, a tissue connector assembly 11 is attached to the free end of the graft vessel along an edge margin of the vessel. In order to attach the connector assembly 11, the surgeon grasps needle 16 with a needle holder (e.g., surgical pliers, forceps, or any other suitable instrument) and inserts needle 16 into the tissue of graft vessel 12 in a direction from the interior of the vessel to the exterior of the vessel. The surgeon then releases the needle 16 and grasps a forward end of the needle which is now located outside graft vessel 12 and pulls the needle and a portion of suture 18 through the vessel. Needle 17 is passed through opening 120 formed in the sidewall of the artery 14 and inserted into the tissue of the artery in a direction from the interior of the artery to the exterior of the artery. The surgeon then grasps needle 17 located outside the artery 14 and pulls the needle and a portion of suture 19 through the arterial wall. A second tissue connector assembly 11 may be inserted as described above at a location generally 180 degrees from the location of the first tissue connector in a conventional "heel and toe" arrangement.

Once the tissue connector assemblies 11 are inserted, graft vessel 12 is positioned above and aligned with opening 120 in the sidewall of the artery 14 (FIG. 16A). A section of each assembly is located between graft vessel 12 and artery 14. The needles 16 and 17 are pulled generally away from the artery 14 to reduce the length of the sutures 18 and 19 (eliminate slack of the sutures) between vessel 12 and artery and "parachute" the vessel onto the artery (FIG. 16B). The needles 17 are then pulled away from the artery 14 until each fastener 20 is positioned within the target vessel 14 as shown in FIG. 16B. Needles 16 are then pulled away from graft 12 until the fasteners are positioned with one end of each fastener 20 extending from the vessel and the opposite end of each fastener extending from the artery (FIG. 16C). The edges of the graft vessel 12 and artery 14 are positioned adjacent one another to form a continuous interior and exterior surface along the mating portions of the vessel and artery. As shown in FIG. 16F, the tissue is compressed within the fastener 20.

A surgical instrument (e.g., needle holder) is used to radially squeeze each locking device 28 to release the locking device from the fastener 20. Upon removal of each locking device 28, each coil 26 moves to its free uncompressed state which allows fastener wire 34 to return to its original undeformed closed position (FIG. 16D). As the wires 34 move to their closed position the adjacent tissues of the graft vessel 12 and artery 14 which were previously pulled together during the parachuting of the graft vessel onto the artery, are squeezed together to securely engage the graft vessel and artery (FIGS. 16E and 16F). It should be noted that as each locking device 28 is squeezed at least two steps are accomplished. The fastener 20 is released from locking device 28, thus allowing coil 26 to uncompress and the wire 34 to move to its closed configuration, and the needle 16 is released from the fastener. Thus, any of the locking devices 28 described above provides for simultaneous actuating closure of the fastener 20 and release of the needle 16 from the fastener. Further, radially compression of release mechanisms 29 releases needles 17 and sutures 19 from the fasteners. However, if one of the synchronous release systems described with reference to FIGS. 10A-10F is used, radial compression of a locking device 28 device will effect essentially simultaneous closure actuation of a respective fastener and release of needles 16 and 17 and sutures 18 and 19.

The tissue connector assemblies 300 are subsequently inserted at circumferentially spaced locations around the periphery of the graft vessel to sealingly fasten graft vessel 12 to artery 14. Needle 16 of fastener 300 is inserted into graft vessel 12 from the exterior surface of the graft vessel and pushed through the graft vessel and artery 14 tissue. The needle holder is then used to pull the needle 16 through the arterial wall. An instrument (same needle holder or other suitable instrument) is used to apply a squeezing force to the locking device 28 to release fastener 20 from needle 16. This allows coil 26 to move to its uncompressed configuration and the wire to move to its closed position. It should be noted that the tissue connector assemblies 11 may remain with their fasteners in their open position while tissue connector assemblies 300 are inserted into the tissue and moved to their closed position. The locking devices 28 of the tissue connector assemblies 11 may subsequently be removed from the fasteners 20 to allow the fasteners to move to their closed position. The number and combination of tissue connector assemblies 11 and 300 required to sealingly secure the connecting tissues together may vary. For example, only tissue connector assemblies 11 may be used to complete the entire anastomosis.

Although coils 26 are shown remaining on the fastener or wire (FIG. 16D), it is to be understood that coils 26 may also be removed from wires 34, leaving only the wires in the connected tissue.

As an alternative to inserting tissue connector assemblies 11 at "heel and toe" locations described above, a number of tissue connector assemblies 11 may be inserted generally around the location of the heel. The graft vessel may then be pulled towards the artery to determine whether the opening formed in the sidewall of the artery is large enough before completing the anastomosis. It also should be understood that tissue connector assemblies 211 may be used instead of or in conjunction with assemblies 11.

FIGS. 19A-19D diagrammatically illustrate an alternative method of aligning and connecting graft and target vessels, such as connecting a graft vessel 1901 to an artery 1903 (target vessel) using tissue connector assemblies 1701 and 1907. The bridge clip of tissue connector assembly 1701 can be used to secure the anastomosis at the heal or at the toe, while tissue connector assembly 1907 can be a tissue connector assembly attached to one piercing member, as disclosed in the copending U.S. Patent application having Ser. No. 09/259,705. Alternatively tissue connector 300 could be used in place of tissue connector 1907. In this example, one tissue connector assembly 1701 is used to make a connection where a toe 1905 of graft vessel 1901 attaches to target vessel 1903, and other tissue connectors 1907 are used at the other attachment locations.

FIG. 19A shows tissue connector 1905 after threading each of piercing members 16' and 16" through the outer surface of toe 1905 and through the inner surface of target vessel 1903. Piercing toe 1905 at two points having the approximate spacing of the length of bridge 1705 allows the bridge to be brought against the outer surface of the graft vessel 1901. This positioning, in which one vessel is brought down or "parachuted" onto another, is advantageous for performing an anastomosis, as it allows the graft vessel to be pulled down onto the target vessel 1903. Because the bridge is rigid, the force on target vessel 1903 is distributed across the bridge 1705. In contrast, the use of a flexible suture for this procedure would pull the tissue between the two piercings together producing a "purse string" effect that is not desired when suturing, and could also possibly tear the tissue.

The piercings on target vessel 1903 are spaced similarly to those on toe 1905. With tissue connector 1701 positioned as in FIG. 19A, the piercing members 16' and 16" can be gently pulled, allowing for precise and careful placement of toe 1905 on target vessel 1903. Once the vessels 1901 and 1903 are aligned and the release members 28 and 29 are pulled through the top side of target vessel 1903, bridge clip 1707 can be released from the flexible members 18 and piercing members 16. FIG. 19B shows bridge clip 1707 in the closed configuration as it appears after joining vessels 1901 and 1903. Each fastener 1703' and 1703" is positioned, prior to closing, from the outer to inner surface of 1901 and through the inner to outer surface of target vessel 1903. Upon closing, each fastener completes the loop, holding the two vessels at two positions separated by the distance of the bridge 1705. The fastening of the vessels at two locations that are held together by the bridge portion provides added support to the anastomosis at the point where the forces which tend to pull the vessels apart is greatest. Once the graft-target attachment is secured at toe 1905, the remainder of the attachment can be performed using tissue connectors 1907 as shown in FIGS. 19B-C.

Although the suturing procedure has been described for an end-to-side anastomosis, it should be appreciated that the procedure is applicable to an end-to-end and side-to-side anastomosis, connecting various tissue structures including single and multiple tissue structures, and puncture sites, and connecting tissue to a prosthetic graft or valve, for example.

Bridge clip 1705 can also be used to perform an attachment similar to a horizontal mattress suture, as is illustrated in FIG. 20. FIGS. 20A and 20B show a top and a side view, respectively, of bridge clip 1705 used to perform a horizontal mattress suture. A procedure that may be used to clip the tissue as in FIG. 20 is to aligning tissue edges 2007 and 2009 of tissues 2001 and 2003, pierce tissue 2001 and 2003 with piercing members 16 to create piercings 2005, and then releasing clips 1703. When this is done, the bridge portion 1705 sits on an outer surface to tissue 2001 while the clips 1703 go through the piercings 2005 and wrap around the edges 2007 and 2009 to towards tissue 2001.

It will be observed from the foregoing that the tissue connector assemblies of the present invention have numerous advantages. Importantly, the assemblies are easier and faster to apply than conventional sutures that require tying multiple knots. The assemblies also may be used in minimally invasive procedures including endoscopic procedures.

All references cited above are incorporated herein by reference.

The above is a detailed description of particular embodiments of the invention. It is recognized that departures from the disclosed embodiments may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. A tissue connector assembly comprising a surgical fastener comprising two clips, each sized and shaped to attach tissues and hold the tissues together therein;

wherein at least one of said two clips is a self-closing clip adapted to self-transition from a first shape to a second shape, the first and second shapes being different, and a bridge portion connecting said two clips and spacing said clips from one another;

wherein said bridge portion is substantially straight;

wherein each of said two clips has an open configuration and a closed configuration independent of an other of said two clips; and wherein each clip has a proximal end point and a distal end point and wherein the proximal end point is separated from the distal end point when said clip is in said open configuration and wherein the distance between said proximal end point and said distal end point is reduced when said clip is in said closed configuration.

2. The tissue connector assembly of claim 1, wherein said self-closing clip comprises shape memory material.

3. The tissue connector assembly of claim 1, further comprising a coil surrounding a substantial length of said self-closing clip.

4. The tissue connector of claim 1, wherein said closed configuration is an unbiased configuration.

5. The tissue connector assembly of claim 1, wherein said closed configuration is a loop.

6. The tissue connector assembly of claim 1, wherein said open configuration is a biased configuration, and further comprising a release mechanism having a first position to bias said self-closing clip in said open configuration.

7. The tissue connector assembly of claim 1, wherein said closed configuration is an unbiased configuration, and wherein said release mechanism has a second position to unbias said self-closing clip into said closed configuration.

8. The tissue connector assembly of claim 7, further comprising a coil surrounding a substantial length of said self-closing clip, where said coil is coupled at one point on said self-closing clip and releasably coupled via said release mechanism at a second point on said self-closing clip.

9. The surgical fastener of claim 8, wherein said first position provides for compressing said coil between said first point and second point to form said biased configuration.

10. The tissue connector assembly of claim 9, wherein said second position provides for releasably uncoupling said coil from said second point to form said unbiased configuration.

11. The tissue connector assembly of claim 1, wherein said surgical fastener has two ends including a first end and a second end, and further comprising two tissue piercing members including a first tissue piercing member releasably coupled to the first end and a second tissue piercing member releasably coupled to said second end.

12. The tissue connector assembly of claim 11, further comprising a release mechanism, and wherein said release mechanism activates said release of said two piercing members from said respective two ends.

13. The tissue connector assembly of claim 12, wherein said release mechanism activates the closing of said self-closing clip.

14. The tissue connector assembly of claim 11, further comprising two sutures, wherein said coupling of said first tissue piercing member to said first end includes one of said sutures, and wherein said coupling of said second tissue piercing member to said second end includes the other of said sutures.

15. The tissue connector assembly of claim 14, wherein said suture of said first coupling and said suture of said second coupling are between about 10 mm and about 300 mm in length.

16. A tissue connector assembly comprising:
a surgical fastener comprising two clips sized and shaped to attach tissues and hold the tissues therein including at least one self-closing clip having an open configuration and a closed configuration, where said closed configuration is an unbiased configuration having a loop shape and said open configuration is a biased configuration having a shape differing from a shape of said closed configuration, and a bridge portion having a substantially straight portion connecting said two clips; and
a release mechanism having a first position to bias said self-closing clip in said open configuration and a second position to unbias said self-closing clip into said closed configuration;
further comprising a coil surrounding a substantial length of said self-closing clip, where said coil is coupled at one point on said self-closing clip and releasably coupled via said release mechanism at a second point on said self-closing clip.

17. The surgical fastener of claim 16, wherein said first position provides for compressing said coil between said first point and second point to form said biased configuration.

18. The tissue connector assembly of claim 17, wherein said second position provides for releasably uncoupling said coil from said second point to form said unbiased configuration.

19. Tissue connector apparatus comprising a surgical clip sized and shaped to attach tissues, first and second tissue piercing members each having first and second end portions, first and second couplings, and first and second flexible members, said surgical clip having first and second end portions, said first coupling being coupled to said first end portion of said surgical clip and said second coupling being coupled to said second end portion of said surgical clip, said first flexible member having a first end portion coupled to said first coupling and a second end portion secured to said second end portion of said first tissue piercing member, said second flexible member having a first end portion coupled to said second coupling and a second end portion secured to said second end portion of said second tissue piercing member, said surgical clip comprising an elongated member, a pair of coils surrounding at least a portion of said elongated member, said pair of coils being serially arranged and spaced from one another along said elongated member, said elongated member being shape memory material and having an unbiased shape, which includes a plurality of loops, and a biased shape, said elongated member tending to move toward said unbiased shape from said biased shape.

20. The tissue connector apparatus of claim 19 wherein said first coupling releasably couples said first end portion of said surgical clip to said first needle.

21. The tissue connector apparatus of claim 20 wherein said second coupling releasably couples said second end portion of said surgical clip to said second needle.

22. Tissue connector apparatus comprising an elongated member having a first loop shaped portion adapted to hold tissue therein, a second loop shaped portion adapted to hold tissue therein, and a bridge portion bridging said first and second loop shaped portions, each loop shaped portion having a free end and being deformable into a second deformed shape and self-tending to return from the second deformed shape towards the loop shape;
further including a pair of coils, one of said coils surrounding at least a portion of one of said first loop shaped portion and the other of said coils surrounding at least a portion of said second loop shaped portion.

23. The tissue connector apparatus of claim 22 wherein each coil has an outer end and an inner end, and said elongated member has two enlarged end portions, further including a restraint coupled to said elongated member adjacent to each of said inner ends.

24. Tissue connector apparatus comprising an elongated member having a first loop shaped portion, a second loop shaped portion and a bridge portion bridging said first and second loop shaped portions, each loop shaped portion having a piercing element at one end and a portion that merges into said bridge shaped portion, each loop shaped portion being deformable into a second deformed shape and having the property of tending to return towards its loop shape by moving upon itself;
further including a pair of coils, one of said coils surrounding at least a portion of one of said first loop shaped portion and the other of said coils surrounding at least a portion of said second loop shaped portion.

25. The tissue connector apparatus of claim 24 wherein each coil has an outer end and an inner end, and said elongated member has two enlarged end portions, further including a restraint coupled to said elongated member adjacent to each of said inner ends.

\* \* \* \* \*